(12) United States Patent
Wu et al.

(10) Patent No.: US 11,441,171 B2
(45) Date of Patent: Sep. 13, 2022

(54) METHOD FOR PROCESSING POLYNUCLEOTIDE-CONTAINING SAMPLES

(71) Applicant: HANDYLAB, INC., Franklin Lakes, NJ (US)

(72) Inventors: Betty Wu, Canton, MI (US); John S. Althaus, Saline, MI (US); Nikhil Phadke, Ann Arbor, MI (US); Sundaresh N. Brahmasandra, Ann Arbor, MI (US); Kalyan Handique, Ann Arbor, MI (US); Aaron Kehrer, Ypsilanti, MI (US); Gene Parunak, Saline, MI (US); Cecelia Haley, Canton, MI (US); Ted Springer, Ann Arbor, MI (US)

(73) Assignee: HANDYLAB, INC., Franklin Lakes, NJ (US)

( * ) Notice: Subject to any disclaimer, the term of this patent is extended or adjusted under 35 U.S.C. 154(b) by 0 days.

(21) Appl. No.: 16/832,997

(22) Filed: Mar. 27, 2020

(65) Prior Publication Data
US 2021/0047676 A1 Feb. 18, 2021

Related U.S. Application Data

(63) Continuation of application No. 16/556,067, filed on Aug. 29, 2019, now Pat. No. 10,604,788, which is a
(Continued)

(51) Int. Cl.
*C12Q 1/6806* (2018.01)
*B01L 3/00* (2006.01)
(Continued)

(52) U.S. Cl.
CPC .......... *C12Q 1/6806* (2013.01); *B01F 25/433* (2022.01); *B01F 25/4331* (2022.01);
(Continued)

(58) Field of Classification Search
CPC .................. C12Q 1/6806; C12Q 1/686; C12Q 2565/629; B01F 25/433; B01F 25/4331;
(Continued)

(56) References Cited

U.S. PATENT DOCUMENTS

| D189,404 S | 12/1960 | Nicolle |
| 3,050,239 A | 8/1962 | Williams |

(Continued)

FOREIGN PATENT DOCUMENTS

| AU | 1357102 | 3/2002 |
| AU | 3557502 | 7/2002 |

(Continued)

OTHER PUBLICATIONS

Handique et al, On-Chip Thermopneumatic Pressure for Discrete Drop Pumping, 2001, Analytical Chemistry, 73, 1831-1838 (Year: 2001).*

(Continued)

*Primary Examiner* — Narayan K Bhat
(74) *Attorney, Agent, or Firm* — Knobbe Martens Olson & Bear LLP

(57) ABSTRACT

Methods and systems for processing polynucleotides (e.g., DNA) are disclosed. A processing region includes one or more surfaces (e.g., particle surfaces) modified with ligands that retain polynucleotides under a first set of conditions (e.g., temperature and pH) and release the polynucleotides under a second set of conditions (e.g., higher temperature and/or more basic pH). The processing region can be used to, for example, concentrate polynucleotides of a sample and/or separate inhibitors of amplification reactions from the polynucleotides. Microfluidic devices with a processing region are disclosed.

20 Claims, 25 Drawing Sheets

Related U.S. Application Data continuation of application No. 16/518,735, filed on Jul. 22, 2019, now Pat. No. 10,443,088, which is a continuation of application No. 14/506,471, filed on Oct. 3, 2014, now Pat. No. 10,364,456, which is a continuation of application No. 11/281,247, filed on Nov. 16, 2005, now Pat. No. 8,852,862, which is a continuation-in-part of application No. PCT/US2005/015345, filed on May 3, 2005.

(60) Provisional application No. 60/567,174, filed on May 3, 2004, provisional application No. 60/645,784, filed on Jan. 21, 2005.

(51) Int. Cl.
  *F16K 99/00* (2006.01)
  *C12N 15/10* (2006.01)
  *C12Q 1/686* (2018.01)
  *B01F 25/433* (2022.01)
  *B01F 33/30* (2022.01)
  *B01L 7/00* (2006.01)

(52) U.S. Cl.
  CPC .......... *B01F 33/30* (2022.01); *B01L 3/50273* (2013.01); *B01L 3/502707* (2013.01); *B01L 3/502738* (2013.01); *B01L 3/502753* (2013.01); *B01L 3/523* (2013.01); *C12N 15/101* (2013.01); *C12N 15/1006* (2013.01); *C12Q 1/686* (2013.01); *F16K 99/0001* (2013.01); *F16K 99/0019* (2013.01); *F16K 99/0032* (2013.01); *F16K 99/0036* (2013.01); *F16K 99/0044* (2013.01); *B01L 3/5082* (2013.01); *B01L 3/502715* (2013.01); *B01L 3/502723* (2013.01); *B01L 3/565* (2013.01); *B01L 7/52* (2013.01); *B01L 2200/10* (2013.01); *B01L 2200/16* (2013.01); *B01L 2300/0672* (2013.01); *B01L 2300/087* (2013.01); *B01L 2300/0816* (2013.01); *B01L 2300/0867* (2013.01); *B01L 2300/0887* (2013.01); *B01L 2400/0442* (2013.01); *B01L 2400/0481* (2013.01); *B01L 2400/0487* (2013.01); *B01L 2400/0633* (2013.01); *B01L 2400/0677* (2013.01); *B01L 2400/0683* (2013.01); *B01L 2400/0694* (2013.01); *F16K 99/0034* (2013.01); *F16K 2099/0084* (2013.01)

(58) Field of Classification Search
  CPC ............... B01F 33/30; B01L 3/502707; B01L 3/50273; B01L 3/502738; B01L 3/502753; B01L 3/523; B01L 3/502715; B01L 3/502723; B01L 3/5082; B01L 3/565; B01L 7/52; B01L 2200/10; B01L 2200/16; B01L 2300/0672; B01L 2300/0816; B01L 2300/0867; B01L 2300/087; B01L 2300/0887; B01L 2400/0442; B01L 2400/0481; B01L 2400/0487; B01L 2400/0633; B01L 2400/0677; B01L 2400/0683; B01L 2400/0694; C12N 15/1006; C12N 15/101; F16K 99/0001; F16K 99/0019; F16K 99/0032; F16K 99/0036; F16K 99/0044; F16K 99/0034; F16K 2099/0084; C12P 19/34
  See application file for complete search history.

(56) References Cited

U.S. PATENT DOCUMENTS

| | | |
|---|---|---|
| 3,905,772 A | 9/1975 | Hartnett et al. |
| 3,985,649 A | 10/1976 | Eddelman |
| 4,018,089 A | 4/1977 | Dzula et al. |
| 4,018,652 A | 4/1977 | Lanham et al. |
| 4,038,192 A | 7/1977 | Serur |
| 4,055,395 A | 10/1977 | Honkawa et al. |
| D249,706 S | 9/1978 | Adamski |
| 4,139,005 A | 2/1979 | Dickey |
| D252,157 S | 6/1979 | Kronish et al. |
| D252,341 S | 7/1979 | Thomas |
| D254,687 S | 4/1980 | Fadler et al. |
| 4,212,744 A | 7/1980 | Oota |
| D261,033 S | 9/1981 | Armbruster |
| D261,173 S | 10/1981 | Armbruster |
| 4,301,412 A | 11/1981 | Hill et al. |
| 4,439,526 A | 3/1984 | Columbus |
| 4,457,329 A | 7/1984 | Werley et al. |
| 4,466,740 A | 8/1984 | Kano et al. |
| 4,472,357 A | 9/1984 | Levy et al. |
| 4,504,582 A | 3/1985 | Swann |
| 4,522,786 A | 6/1985 | Ebersole |
| D279,817 S | 7/1985 | Chen et al. |
| D282,208 S | 1/1986 | Lowry |
| 4,599,315 A | 7/1986 | Terasaki et al. |
| 4,612,873 A | 9/1986 | Eberle |
| 4,612,959 A | 9/1986 | Costello |
| D288,478 S | 2/1987 | Carlson et al. |
| 4,647,432 A | 3/1987 | Wakatake |
| 4,654,127 A | 3/1987 | Baker et al. |
| 4,673,657 A | 6/1987 | Christian |
| 4,678,752 A | 7/1987 | Thorne et al. |
| 4,683,195 A | 7/1987 | Mullis et al. |
| 4,683,202 A | 7/1987 | Mullis |
| 4,698,302 A | 10/1987 | Whitehead et al. |
| D292,735 S | 11/1987 | Lovborg |
| 4,720,374 A | 1/1988 | Ramachandran |
| 4,724,207 A | 2/1988 | Hou et al. |
| 4,795,698 A | 1/1989 | Owen et al. |
| 4,798,693 A | 1/1989 | Mase et al. |
| 4,800,022 A | 1/1989 | Leonard |
| 4,827,944 A | 5/1989 | Nugent |
| 4,841,786 A | 6/1989 | Schulz |
| D302,294 S | 7/1989 | Hillman |
| 4,855,110 A | 8/1989 | Marker et al. |
| 4,871,779 A | 10/1989 | Killat et al. |
| 4,889,818 A | 12/1989 | Gelfand et al. |
| 4,895,650 A | 1/1990 | Wang |
| 4,902,624 A | 2/1990 | Columbus et al. |
| 4,914,710 A | 4/1990 | Ward et al. |
| 4,919,829 A | 4/1990 | Gates et al. |
| 4,921,809 A | 5/1990 | Schiff et al. |
| 4,935,342 A | 6/1990 | Seligson et al. |
| 4,946,562 A | 8/1990 | Guruswamy |
| 4,948,561 A | 8/1990 | Hinckley et al. |
| 4,949,742 A | 8/1990 | Rando et al. |
| D310,413 S | 9/1990 | Bigler et al. |
| 4,963,498 A | 10/1990 | Hillman |
| 4,965,188 A | 10/1990 | Mullis et al. |
| 4,967,950 A | 11/1990 | Legg et al. |
| D312,692 S | 12/1990 | Bradley |
| 4,978,502 A | 12/1990 | Dole et al. |
| 4,978,622 A | 12/1990 | Mishell et al. |
| 4,989,626 A | 2/1991 | Takagi et al. |
| 4,994,373 A | 2/1991 | Stavrianopoulos et al. |
| 4,997,772 A | 3/1991 | Sutton et al. |
| 5,001,417 A | 3/1991 | Pumphrey et al. |
| 5,004,583 A | 4/1991 | Guruswamy et al. |
| 5,048,554 A | 9/1991 | Kremer |
| 5,053,199 A | 10/1991 | Keiser et al. |
| 5,060,823 A | 10/1991 | Perlman |
| 5,061,336 A | 10/1991 | Soane |
| 5,064,618 A | 11/1991 | Baker et al. |
| 5,071,531 A | 12/1991 | Soane |
| 5,089,233 A | 2/1992 | DeVaney, Jr. et al. |
| 5,091,328 A | 2/1992 | Miller |

(56) References Cited

U.S. PATENT DOCUMENTS

| | | |
|---|---|---|
| D324,426 S | 3/1992 | Fan et al. |
| 5,096,669 A | 3/1992 | Lauks et al. |
| D325,638 S | 4/1992 | Sloat et al. |
| 5,126,002 A | 6/1992 | Iwata et al. |
| 5,126,022 A | 6/1992 | Soane et al. |
| D328,135 S | 7/1992 | Fan et al. |
| D328,794 S | 8/1992 | Frenkel et al. |
| 5,135,627 A | 8/1992 | Soane |
| 5,135,872 A | 8/1992 | Pouletty et al. |
| 5,147,606 A | 9/1992 | Charlton et al. |
| 5,147,777 A | 9/1992 | Sutton et al. |
| 5,155,166 A | 10/1992 | Danielson et al. |
| 5,169,512 A | 12/1992 | Wiedenmann et al. |
| 5,173,269 A | 12/1992 | Mon et al. |
| D333,522 S | 2/1993 | Gianino |
| 5,186,339 A | 2/1993 | Heissler |
| 5,192,507 A | 3/1993 | Taylor et al. |
| 5,208,163 A | 5/1993 | Charlton et al. |
| 5,217,694 A | 6/1993 | Gibler et al. |
| 5,223,226 A | 6/1993 | Wittmer et al. |
| 5,229,297 A | 7/1993 | Schnipelsky et al. |
| 5,231,015 A | 7/1993 | Cummins et al. |
| D338,275 S | 8/1993 | Fischer et al. |
| 5,234,809 A | 8/1993 | Boom et al. |
| 5,250,263 A | 10/1993 | Manz |
| 5,252,743 A | 10/1993 | Barrett et al. |
| 5,256,376 A | 10/1993 | Callan et al. |
| 5,273,716 A | 12/1993 | Northrup et al. |
| 5,275,787 A | 1/1994 | Yuguchi et al. |
| 5,282,950 A | 2/1994 | Dietze et al. |
| 5,296,375 A | 3/1994 | Kricka et al. |
| 5,304,477 A | 4/1994 | Nagoh et al. |
| 5,304,487 A | 4/1994 | Wilding et al. |
| D347,478 S | 5/1994 | Pinkney |
| 5,311,896 A | 5/1994 | Kaartinen et al. |
| 5,311,996 A | 5/1994 | Duffy et al. |
| 5,316,727 A | 5/1994 | Suzuki et al. |
| 5,327,038 A | 7/1994 | Culp |
| 5,334,499 A | 8/1994 | Burdick et al. |
| 5,338,671 A | 8/1994 | Scalice et al. |
| 5,339,486 A | 8/1994 | Persic, Jr. |
| D351,475 S | 10/1994 | Gerber |
| D351,913 S | 10/1994 | Hieb et al. |
| 5,364,591 A | 11/1994 | Green et al. |
| 5,372,946 A | 12/1994 | Cusak et al. |
| 5,374,395 A | 12/1994 | Robinson |
| 5,384,499 A | 1/1995 | Pedersen et al. |
| 5,389,339 A | 2/1995 | Petschek et al. |
| D356,232 S | 3/1995 | Armstrong et al. |
| 5,397,709 A | 3/1995 | Berndt |
| 5,401,465 A | 3/1995 | Smethers et al. |
| 5,411,708 A | 5/1995 | Moscetta et al. |
| 5,414,245 A | 5/1995 | Hackleman |
| 5,415,839 A | 5/1995 | Zaun et al. |
| 5,416,000 A | 5/1995 | Allen et al. |
| 5,422,271 A | 6/1995 | Chen et al. |
| 5,422,284 A | 6/1995 | Lau |
| 5,427,946 A | 6/1995 | Kricka et al. |
| 5,443,791 A | 8/1995 | Cathcart et al. |
| 5,466,574 A | 11/1995 | Liberti et al. |
| 5,474,796 A | 12/1995 | Brennan |
| 5,475,487 A | 12/1995 | Mariella, Jr. et al. |
| D366,116 S | 1/1996 | Biskupski |
| 5,486,335 A | 1/1996 | Wilding et al. |
| 5,494,639 A | 2/1996 | Grzegorzewski |
| 5,498,392 A | 3/1996 | Wilding et al. |
| 5,503,803 A | 4/1996 | Brown |
| 5,516,410 A | 5/1996 | Schneider et al. |
| 5,519,635 A | 5/1996 | Miyake et al. |
| 5,529,677 A | 6/1996 | Schneider et al. |
| 5,559,432 A | 9/1996 | Logue |
| 5,565,171 A | 10/1996 | Dovichi et al. |
| 5,569,364 A | 10/1996 | Hooper et al. |
| 5,576,218 A | 11/1996 | Zurek et al. |
| 5,578,270 A | 11/1996 | Reichler et al. |
| 5,578,818 A | 11/1996 | Kain et al. |
| 5,579,928 A | 12/1996 | Anukwuem |
| 5,580,523 A | 12/1996 | Bard |
| 5,582,884 A | 12/1996 | Ball et al. |
| 5,582,988 A | 12/1996 | Backus et al. |
| 5,585,069 A | 12/1996 | Zanucchi et al. |
| 5,585,089 A | 12/1996 | Queen et al. |
| 5,585,242 A | 12/1996 | Bouma et al. |
| 5,587,128 A | 12/1996 | Wilding et al. |
| 5,589,136 A | 12/1996 | Northrup et al. |
| 5,593,838 A | 1/1997 | Zanzucchi et al. |
| 5,595,708 A | 1/1997 | Berndt |
| 5,599,432 A | 2/1997 | Manz et al. |
| 5,599,503 A | 2/1997 | Manz et al. |
| 5,599,667 A | 2/1997 | Arnold, Jr. et al. |
| 5,601,727 A | 2/1997 | Bormann et al. |
| 5,603,351 A | 2/1997 | Cherukuri et al. |
| 5,605,662 A | 2/1997 | Heller et al. |
| 5,609,910 A | 3/1997 | Hackleman |
| D378,782 S | 4/1997 | LaBarbera et al. |
| 5,628,890 A | 5/1997 | Carter et al. |
| 5,630,920 A | 5/1997 | Friese et al. |
| 5,631,337 A | 5/1997 | Sassi et al. |
| 5,632,876 A | 5/1997 | Zanzucchi et al. |
| 5,632,957 A | 5/1997 | Heller et al. |
| 5,635,358 A | 6/1997 | Wilding et al. |
| 5,637,469 A | 6/1997 | Wilding et al. |
| 5,639,423 A | 6/1997 | Northrup et al. |
| 5,639,428 A | 6/1997 | Cottingham |
| 5,643,738 A | 7/1997 | Zanzucchi et al. |
| 5,645,801 A | 7/1997 | Bouma et al. |
| 5,646,039 A | 7/1997 | Northrup et al. |
| 5,646,049 A | 7/1997 | Tayi |
| 5,647,994 A | 7/1997 | Tuunanen et al. |
| 5,651,839 A | 7/1997 | Rauf |
| 5,652,141 A | 7/1997 | Henco et al. |
| 5,652,149 A | 7/1997 | Mileaf et al. |
| D382,346 S | 8/1997 | Buhler et al. |
| D382,647 S | 8/1997 | Staples et al. |
| 5,654,141 A | 8/1997 | Mariani et al. |
| 5,658,515 A | 8/1997 | Lee et al. |
| 5,667,976 A | 9/1997 | Van Ness et al. |
| 5,671,303 A | 9/1997 | Shieh et al. |
| 5,674,394 A | 10/1997 | Whitmore |
| 5,674,742 A | 10/1997 | Northrup et al. |
| 5,681,484 A | 10/1997 | Zanzucchi et al. |
| 5,681,529 A | 10/1997 | Taguchi et al. |
| 5,683,657 A | 11/1997 | Mian |
| 5,683,659 A | 11/1997 | Hovatter |
| 5,699,157 A | 12/1997 | Parce et al. |
| 5,700,637 A | 12/1997 | Southern |
| 5,705,813 A | 1/1998 | Apffel et al. |
| 5,720,923 A * | 2/1998 | Haff ............... B01L 9/065 422/138 |
| 5,721,136 A | 2/1998 | Finney et al. |
| 5,725,831 A | 3/1998 | Reichler et al. |
| 5,726,026 A | 3/1998 | Wilding et al. |
| 5,726,404 A | 3/1998 | Brody |
| 5,726,944 A | 3/1998 | Pelley et al. |
| 5,731,212 A | 3/1998 | Gavin et al. |
| 5,744,366 A | 4/1998 | Kricka et al. |
| 5,746,978 A | 5/1998 | Bienhaus et al. |
| 5,747,666 A | 5/1998 | Willis |
| 5,750,015 A | 5/1998 | Soane et al. |
| 5,755,942 A | 5/1998 | Zanzucchi et al. |
| 5,762,874 A | 6/1998 | Seaton et al. |
| 5,763,262 A | 6/1998 | Wong et al. |
| 5,770,029 A | 6/1998 | Nelson et al. |
| 5,770,388 A | 6/1998 | Vorpahl |
| 5,772,966 A | 6/1998 | Maracas et al. |
| 5,779,868 A | 7/1998 | Parce et al. |
| 5,783,148 A | 7/1998 | Cottingham et al. |
| 5,787,032 A | 7/1998 | Heller et al. |
| 5,788,814 A | 8/1998 | Sun et al. |
| 5,800,600 A | 9/1998 | Lima-Marques et al. |
| 5,800,690 A | 9/1998 | Chow et al. |
| 5,804,436 A | 9/1998 | Okun et al. |
| D399,959 S | 10/1998 | Prokop et al. |
| 5,819,749 A | 10/1998 | Lee et al. |

(56) References Cited

U.S. PATENT DOCUMENTS

| | | |
|---|---|---|
| 5,827,481 A | 10/1998 | Bente et al. |
| 5,842,106 A | 11/1998 | Thaler et al. |
| 5,842,787 A | 12/1998 | Kopf-Sill et al. |
| 5,846,396 A | 12/1998 | Zanzucchi et al. |
| 5,846,493 A | 12/1998 | Bankier et al. |
| 5,849,208 A | 12/1998 | Hayes et al. |
| 5,849,486 A | 12/1998 | Heller et al. |
| 5,849,489 A | 12/1998 | Heller |
| 5,849,598 A | 12/1998 | Wilson et al. |
| 5,852,495 A | 12/1998 | Parce |
| 5,856,174 A | 1/1999 | Lipshutz et al. |
| 5,858,187 A | 1/1999 | Ramsey et al. |
| 5,858,188 A | 1/1999 | Soane et al. |
| 5,863,502 A | 1/1999 | Southgate et al. |
| 5,863,708 A | 1/1999 | Zanzucchi et al. |
| 5,863,801 A | 1/1999 | Southgate et al. |
| 5,866,345 A | 2/1999 | Wilding et al. |
| 5,869,004 A | 2/1999 | Parce et al. |
| 5,869,244 A | 2/1999 | Martin et al. |
| 5,872,010 A | 2/1999 | Karger et al. |
| 5,872,623 A | 2/1999 | Stabile et al. |
| 5,874,046 A | 2/1999 | Megerle |
| 5,876,675 A | 3/1999 | Kennedy |
| 5,880,071 A | 3/1999 | Parce et al. |
| 5,882,465 A | 3/1999 | McReynolds |
| 5,883,211 A | 3/1999 | Sassi et al. |
| 5,885,432 A | 3/1999 | Hooper et al. |
| 5,885,470 A | 3/1999 | Parce et al. |
| 5,895,762 A | 4/1999 | Greenfield et al. |
| 5,900,130 A | 5/1999 | Benvegnu et al. |
| 5,911,737 A | 6/1999 | Lee et al. |
| 5,912,124 A | 6/1999 | Kumar |
| 5,912,134 A | 6/1999 | Shartle |
| 5,914,229 A | 6/1999 | Loewy |
| 5,916,522 A | 6/1999 | Boyd et al. |
| 5,916,776 A | 6/1999 | Kumar |
| 5,919,646 A | 7/1999 | Okun et al. |
| 5,919,711 A | 7/1999 | Boyd et al. |
| 5,922,591 A | 7/1999 | Anderson et al. |
| 5,927,547 A | 7/1999 | Papen et al. |
| 5,928,161 A | 7/1999 | Krulevitch et al. |
| 5,928,880 A | 7/1999 | Wilding et al. |
| 5,929,208 A | 7/1999 | Heller et al. |
| D413,391 S | 8/1999 | Lapeus et al. |
| 5,932,799 A | 8/1999 | Moles |
| 5,935,401 A | 8/1999 | Amigo |
| 5,939,291 A | 8/1999 | Loewy et al. |
| 5,939,312 A | 8/1999 | Baier et al. |
| 5,942,443 A | 8/1999 | Parce et al. |
| 5,944,717 A | 8/1999 | Lee et al. |
| D413,677 S | 9/1999 | Dumitrescu et al. |
| D414,271 S | 9/1999 | Mendoza |
| 5,948,227 A | 9/1999 | Dubrow |
| 5,948,363 A | 9/1999 | Gaillard |
| 5,948,673 A | 9/1999 | Cottingham |
| 5,955,028 A | 9/1999 | Chow |
| 5,955,029 A | 9/1999 | Wilding et al. |
| 5,957,579 A | 9/1999 | Kopf-Sill et al. |
| 5,958,203 A | 9/1999 | Parce et al. |
| 5,958,349 A | 9/1999 | Petersen et al. |
| 5,958,694 A | 9/1999 | Nikiforov |
| 5,959,221 A | 9/1999 | Boyd et al. |
| 5,959,291 A | 9/1999 | Jensen |
| 5,935,522 A | 10/1999 | Swerdlow et al. |
| 5,964,995 A | 10/1999 | Nikiforov et al. |
| 5,964,997 A | 10/1999 | McBride |
| 5,965,001 A | 10/1999 | Chow et al. |
| 5,965,410 A | 10/1999 | Chow et al. |
| 5,965,886 A | 10/1999 | Sauer et al. |
| 5,968,745 A | 10/1999 | Thorp et al. |
| 5,972,187 A | 10/1999 | Parce et al. |
| 5,973,138 A | 10/1999 | Collis |
| D417,009 S | 11/1999 | Boyd |
| 5,976,336 A | 11/1999 | Dubrow et al. |
| 5,980,704 A | 11/1999 | Cherukuri et al. |
| 5,980,719 A | 11/1999 | Cherukuri et al. |
| 5,981,735 A | 11/1999 | Thatcher et al. |
| 5,985,651 A | 11/1999 | Hunicke-Smith |
| 5,989,402 A | 11/1999 | Chow et al. |
| 5,992,820 A | 11/1999 | Fare et al. |
| 5,993,611 A | 11/1999 | Moroney, III et al. |
| 5,993,750 A | 11/1999 | Ghosh et al. |
| 5,997,708 A | 12/1999 | Craig |
| 6,001,229 A | 12/1999 | Ramsey |
| 6,001,231 A | 12/1999 | Kopf-Sill |
| 6,001,307 A | 12/1999 | Naka et al. |
| 6,004,450 A | 12/1999 | Northrup et al. |
| 6,004,515 A | 12/1999 | Parce et al. |
| 6,007,690 A | 12/1999 | Nelson et al. |
| 6,010,607 A | 1/2000 | Ramsey |
| 6,010,608 A | 1/2000 | Ramsey |
| 6,010,627 A | 1/2000 | Hood, III |
| 6,012,902 A | 1/2000 | Parce |
| D420,747 S | 2/2000 | Dumitrescu et al. |
| D421,130 S | 2/2000 | Cohen et al. |
| 6,024,920 A | 2/2000 | Cunanan |
| D421,653 S | 3/2000 | Purcell |
| 6,033,546 A | 3/2000 | Ramsey |
| 6,033,880 A | 3/2000 | Haff et al. |
| 6,043,080 A | 3/2000 | Lipshutz et al. |
| 6,043,880 A | 3/2000 | Andrews et al. |
| 6,046,056 A | 4/2000 | Parce et al. |
| 6,048,734 A | 4/2000 | Burns et al. |
| 6,054,034 A | 4/2000 | Soane et al. |
| 6,054,277 A | 4/2000 | Furcht et al. |
| 6,056,860 A | 5/2000 | Amigo et al. |
| 6,057,149 A | 5/2000 | Burns et al. |
| 6,062,261 A | 5/2000 | Jacobson et al. |
| 6,063,341 A | 5/2000 | Fassbind et al. |
| 6,063,589 A | 5/2000 | Kellogg et al. |
| 6,068,751 A | 5/2000 | Neukermans |
| 6,068,752 A | 5/2000 | Dubrow et al. |
| 6,071,478 A | 6/2000 | Chow |
| 6,074,725 A | 6/2000 | Kennedy |
| 6,074,827 A | 6/2000 | Nelson et al. |
| D428,497 S | 7/2000 | Lapeus et al. |
| 6,086,740 A | 7/2000 | Kennedy |
| 6,096,509 A | 8/2000 | Okun et al. |
| 6,100,541 A | 8/2000 | Nagle et al. |
| 6,102,897 A | 8/2000 | Lang |
| 6,103,537 A | 8/2000 | Ullman et al. |
| 6,106,685 A | 8/2000 | McBride et al. |
| 6,110,343 A | 8/2000 | Ramsey et al. |
| 6,117,398 A | 9/2000 | Bienhaus et al. |
| 6,123,205 A | 9/2000 | Dumitrescu et al. |
| 6,123,798 A | 9/2000 | Gandhi et al. |
| 6,130,098 A * | 10/2000 | Handique ........... B01F 33/3021 436/52 |
| 6,132,580 A | 10/2000 | Mathies et al. |
| 6,132,684 A | 10/2000 | Marino |
| 6,133,436 A | 10/2000 | Koster et al. |
| D433,759 S | 11/2000 | Mathis et al. |
| 6,143,250 A | 11/2000 | Tajima |
| 6,143,547 A | 11/2000 | Hsu |
| 6,149,787 A | 11/2000 | Chow et al. |
| 6,149,872 A | 11/2000 | Mack et al. |
| 6,156,199 A | 12/2000 | Zuk, Jr. |
| 6,158,269 A | 12/2000 | Dorenkott et al. |
| 6,167,910 B1 | 1/2001 | Chow |
| 6,168,948 B1 | 1/2001 | Anderson et al. |
| 6,171,850 B1 | 1/2001 | Nagle et al. |
| 6,174,675 B1 | 1/2001 | Chow et al. |
| 6,180,950 B1 | 1/2001 | Olsen |
| D438,311 S | 2/2001 | Yamanishi et al. |
| 6,190,619 B1 | 2/2001 | Kilcoin et al. |
| 6,194,563 B1 | 2/2001 | Cruickshank |
| D438,632 S | 3/2001 | Miller |
| D438,633 S | 3/2001 | Miller |
| D439,673 S | 3/2001 | Brophy et al. |
| 6,197,595 B1 | 3/2001 | Anderson et al. |
| 6,203,759 B1 | 3/2001 | Pelc et al. |
| 6,211,989 B1 | 4/2001 | Wulf et al. |
| 6,213,151 B1 | 4/2001 | Jacobson et al. |
| 6,221,600 B1 | 4/2001 | MacLeod et al. |

(56) References Cited

U.S. PATENT DOCUMENTS

| | | |
|---|---|---|
| 6,228,635 B1 | 5/2001 | Armstrong et al. |
| 6,232,072 B1 | 5/2001 | Fisher |
| 6,235,175 B1 | 5/2001 | Dubrow et al. |
| 6,235,313 B1 | 5/2001 | Mathiowitz et al. |
| 6,235,471 B1 | 5/2001 | Knapp et al. |
| 6,236,456 B1 | 5/2001 | Giebeler et al. |
| 6,236,581 B1 | 5/2001 | Foss et al. |
| 6,238,626 B1 | 5/2001 | Higuchi et al. |
| 6,251,343 B1 | 6/2001 | Dubrow et al. |
| 6,254,826 B1 | 7/2001 | Acosta et al. |
| 6,259,635 B1 | 7/2001 | Khouri et al. |
| 6,261,431 B1 | 7/2001 | Mathies et al. |
| 6,267,858 B1 | 7/2001 | Parce et al. |
| D446,306 S | 8/2001 | Ochi et al. |
| 6,271,021 B1 | 8/2001 | Burns et al. |
| 6,274,089 B1 | 8/2001 | Chow et al. |
| 6,280,967 B1 | 8/2001 | Ransom et al. |
| 6,281,008 B1 | 8/2001 | Komai et al. |
| 6,284,113 B1 | 9/2001 | Bjornson et al. |
| 6,284,470 B1 | 9/2001 | Bitner et al. |
| 6,287,254 B1 | 9/2001 | Dodds |
| 6,287,774 B1 | 9/2001 | Nikiforov |
| 6,291,248 B1 | 9/2001 | Haj-Ahmad |
| 6,294,063 B1 | 9/2001 | Becker et al. |
| 6,300,124 B1 | 10/2001 | Blumenfeld et al. |
| 6,302,134 B1 | 10/2001 | Kellogg et al. |
| 6,302,304 B1 | 10/2001 | Spencer |
| 6,303,343 B1 | 10/2001 | Kopf-sill |
| 6,306,273 B1 | 10/2001 | Wainright et al. |
| 6,306,590 B1 | 10/2001 | Mehta et al. |
| 6,310,199 B1 | 10/2001 | Smith et al. |
| 6,316,774 B1 | 11/2001 | Giebeler et al. |
| 6,319,469 B1 | 11/2001 | Mian et al. |
| 6,319,474 B1 | 11/2001 | Krulevitch et al. |
| 6,322,683 B1 | 11/2001 | Wolk et al. |
| 6,326,083 B1 | 12/2001 | Yang et al. |
| 6,326,147 B1 | 12/2001 | Oldham et al. |
| 6,326,211 B1 | 12/2001 | Anderson et al. |
| 6,334,980 B1 | 1/2002 | Hayes et al. |
| 6,337,435 B1 | 1/2002 | Chu et al. |
| 6,353,475 B1 | 3/2002 | Jensen et al. |
| 6,358,387 B1 | 3/2002 | Kopf-sill et al. |
| 6,366,924 B1 | 4/2002 | Parce |
| 6,368,561 B1 | 4/2002 | Rutishauser et al. |
| 6,368,871 B1 | 4/2002 | Christel et al. |
| 6,370,206 B1 | 4/2002 | Schenk |
| 6,375,185 B1 | 4/2002 | Lin |
| 6,375,901 B1 | 4/2002 | Robotti et al. |
| 6,379,884 B2 | 4/2002 | Wada et al. |
| 6,379,929 B1 | 4/2002 | Burns et al. |
| 6,379,974 B1 | 4/2002 | Parce et al. |
| 6,382,254 B1 | 5/2002 | Yang et al. |
| 6,391,541 B1 | 5/2002 | Petersen et al. |
| 6,391,623 B1 | 5/2002 | Besemer et al. |
| 6,395,161 B1 | 5/2002 | Schneider et al. |
| 6,398,956 B1 | 6/2002 | Coville et al. |
| 6,399,025 B1 | 6/2002 | Chow |
| 6,399,389 B1 | 6/2002 | Parce et al. |
| 6,399,952 B1 | 6/2002 | Maher et al. |
| 6,401,552 B1 | 6/2002 | Elkins |
| 6,403,338 B1 | 6/2002 | Knapp et al. |
| 6,408,878 B2 | 6/2002 | Unger et al. |
| 6,413,401 B1 | 7/2002 | Chow et al. |
| 6,416,642 B1 | 7/2002 | Alajoki et al. |
| 6,420,143 B1 | 7/2002 | Kopf-sill |
| 6,425,972 B1 | 7/2002 | McReynolds |
| D461,906 S | 8/2002 | Pham |
| 6,428,987 B2 | 8/2002 | Franzen |
| 6,430,512 B1 | 8/2002 | Gallagher |
| 6,432,366 B2 | 8/2002 | Ruediger et al. |
| 6,440,725 B1 | 8/2002 | Pourahmadi et al. |
| D463,031 S | 9/2002 | Slomski et al. |
| 6,444,461 B1 | 9/2002 | Knapp et al. |
| 6,447,661 B1 | 9/2002 | Chow et al. |
| 6,447,727 B1 | 9/2002 | Parce et al. |
| 6,448,047 B2 | 9/2002 | Dattagupta et al. |
| 6,448,064 B1 | 9/2002 | Vo-Dinh et al. |
| 6,453,928 B1 | 9/2002 | Kaplan et al. |
| 6,458,259 B1 | 10/2002 | Parce et al. |
| 6,461,570 B2 | 10/2002 | Ishihara et al. |
| 6,465,257 B1 | 10/2002 | Parce et al. |
| 6,468,761 B2 | 10/2002 | Yang et al. |
| 6,472,141 B2 | 10/2002 | Nikiforov |
| D466,219 S | 11/2002 | Wynschenk et al. |
| 6,475,364 B1 | 11/2002 | Dubrow et al. |
| D467,348 S | 12/2002 | McMichael et al. |
| D467,349 S | 12/2002 | Niedbala et al. |
| 6,488,897 B2 | 12/2002 | Dubrow et al. |
| 6,495,104 B1 | 12/2002 | Unno et al. |
| 6,498,497 B1 | 12/2002 | Chow et al. |
| 6,500,323 B1 | 12/2002 | Chow et al. |
| 6,500,390 B1 | 12/2002 | Boulton et al. |
| D468,437 S | 1/2003 | McMenamy et al. |
| 6,506,609 B1 | 1/2003 | Wada et al. |
| 6,509,186 B1 | 1/2003 | Zou et al. |
| 6,509,193 B1 | 1/2003 | Tajima |
| 6,511,853 B1 | 1/2003 | Kopf-sill et al. |
| D470,595 S | 2/2003 | Crisanti et al. |
| 6,515,753 B2 | 2/2003 | Maher |
| 6,517,783 B2 | 2/2003 | Horner et al. |
| 6,520,197 B2 | 2/2003 | Deshmukh et al. |
| 6,521,181 B1 | 2/2003 | Northrup et al. |
| 6,521,188 B1 | 2/2003 | Webster |
| 6,524,456 B1 | 2/2003 | Ramsey et al. |
| 6,524,532 B1 | 2/2003 | Northrup |
| 6,524,790 B1 | 2/2003 | Kopf-sill et al. |
| D472,324 S | 3/2003 | Rumore et al. |
| 6,534,295 B2 | 3/2003 | Tai et al. |
| 6,537,432 B1 | 3/2003 | Schneider et al. |
| 6,537,771 B1 | 3/2003 | Farinas et al. |
| 6,540,896 B1 | 4/2003 | Manz et al. |
| 6,544,734 B1 | 4/2003 | Briscoe et al. |
| 6,547,942 B1 | 4/2003 | Parce et al. |
| 6,555,389 B1 | 4/2003 | Ullman et al. |
| 6,556,923 B2 | 4/2003 | Gallagher et al. |
| D474,279 S | 5/2003 | Mayer et al. |
| D474,280 S | 5/2003 | Niedbala et al. |
| 6,558,916 B2 | 5/2003 | Veerapandian et al. |
| 6,558,945 B1 | 5/2003 | Kao |
| 6,565,815 B1 | 5/2003 | Chang et al. |
| 6,569,607 B2 | 5/2003 | McReynolds |
| 6,572,830 B1 | 6/2003 | Burdon et al. |
| 6,575,188 B2 | 6/2003 | Parunak |
| 6,576,459 B2 | 6/2003 | Miles et al. |
| 6,579,453 B1 | 6/2003 | Bächler et al. |
| 6,589,729 B2 | 7/2003 | Chan et al. |
| 6,592,821 B1 | 7/2003 | Wada et al. |
| 6,597,450 B1 | 7/2003 | Andrews et al. |
| 6,602,474 B1 | 8/2003 | Tajima |
| 6,605,475 B1 * | 8/2003 | Taylor ............ G01N 27/44791 422/68.1 |
| 6,613,211 B1 | 9/2003 | Mccormick et al. |
| 6,613,512 B1 | 9/2003 | Kopf-sill et al. |
| 6,613,580 B1 | 9/2003 | Chow et al. |
| 6,613,581 B1 | 9/2003 | Wada et al. |
| 6,614,030 B2 | 9/2003 | Maher et al. |
| 6,620,625 B2 | 9/2003 | Wolk et al. |
| 6,623,860 B2 | 9/2003 | Hu et al. |
| 6,627,406 B1 | 9/2003 | Singh et al. |
| D480,814 S | 10/2003 | Lafferty et al. |
| 6,632,655 B1 | 10/2003 | Mehta et al. |
| 6,633,785 B1 | 10/2003 | Kasahara et al. |
| D482,796 S | 11/2003 | Oyama et al. |
| 6,640,981 B2 | 11/2003 | Lafond et al. |
| 6,649,358 B1 | 11/2003 | Parce et al. |
| 6,664,104 B2 | 12/2003 | Pourahmadi et al. |
| 6,669,831 B2 | 12/2003 | Chow et al. |
| 6,670,133 B2 | 12/2003 | Knapp et al. |
| 6,670,153 B2 | 12/2003 | Stern |
| D484,989 S | 1/2004 | Gebrian |
| 6,672,458 B2 | 1/2004 | Hansen et al. |
| 6,681,616 B2 | 1/2004 | Spaid et al. |
| 6,681,788 B2 | 1/2004 | Parce et al. |
| 6,685,813 B2 | 2/2004 | Williams et al. |

(56) References Cited

U.S. PATENT DOCUMENTS

| | | |
|---|---|---|
| 6,692,700 B2 | 2/2004 | Handique |
| 6,695,009 B2 | 2/2004 | Chien et al. |
| 6,699,713 B2 | 3/2004 | Benett et al. |
| 6,706,519 B1 | 3/2004 | Kellogg et al. |
| 6,720,148 B1 | 4/2004 | Nikiforov |
| 6,730,206 B2 | 5/2004 | Ricco et al. |
| 6,733,645 B1 | 5/2004 | Chow |
| 6,734,401 B2 | 5/2004 | Bedingham et al. |
| 6,737,026 B1 | 5/2004 | Bergh et al. |
| 6,740,518 B1 | 5/2004 | Duong et al. |
| D491,272 S | 6/2004 | Alden et al. |
| D491,273 S | 6/2004 | Biegler et al. |
| D491,276 S | 6/2004 | Langille |
| 6,750,661 B2 | 6/2004 | Brooks et al. |
| 6,752,966 B1 | 6/2004 | Chazan |
| 6,756,019 B1 | 6/2004 | Dubrow et al. |
| 6,762,049 B2 | 7/2004 | Zou et al. |
| 6,764,859 B1 | 7/2004 | Kreuwel et al. |
| 6,766,817 B2 | 7/2004 | Dias da Silva |
| 6,773,567 B1 | 8/2004 | Wolk |
| 6,777,184 B2 | 8/2004 | Nikiforov et al. |
| 6,783,962 B1 | 8/2004 | Olander et al. |
| D495,805 S | 9/2004 | Lea et al. |
| 6,787,015 B2 | 9/2004 | Lackritz et al. |
| 6,787,016 B2 | 9/2004 | Tan et al. |
| 6,787,111 B2 | 9/2004 | Roach et al. |
| 6,790,328 B2 | 9/2004 | Jacobson et al. |
| 6,790,330 B2 | 9/2004 | Gascoyne et al. |
| 6,811,668 B1 | 11/2004 | Berndt et al. |
| 6,818,113 B2 | 11/2004 | Williams et al. |
| 6,819,027 B2 | 11/2004 | Saraf |
| 6,824,663 B1 | 11/2004 | Boone |
| D499,813 S | 12/2004 | Wu |
| D500,142 S | 12/2004 | Crisanti et al. |
| D500,363 S | 12/2004 | Fanning et al. |
| 6,827,831 B1 | 12/2004 | Chow et al. |
| 6,827,906 B1 | 12/2004 | Björnson et al. |
| 6,838,156 B1 | 1/2005 | Neyer et al. |
| 6,838,680 B2 | 1/2005 | Maher et al. |
| 6,852,287 B2 | 2/2005 | Ganesan |
| 6,858,185 B1 | 2/2005 | Kopf-sill et al. |
| 6,859,698 B2 | 2/2005 | Schmeisser |
| 6,861,035 B2 | 3/2005 | Pham et al. |
| 6,878,540 B2 | 4/2005 | Pourahmadi et al. |
| 6,878,755 B2 | 4/2005 | Singh et al. |
| 6,884,628 B2 | 4/2005 | Hubbell et al. |
| 6,887,693 B2 | 5/2005 | McMillan et al. |
| 6,893,879 B2 | 5/2005 | Petersen et al. |
| 6,900,889 B2 | 5/2005 | Bjornson et al. |
| 6,905,583 B2 | 6/2005 | Wainright et al. |
| 6,905,612 B2 | 6/2005 | Dorian et al. |
| 6,906,797 B1 | 6/2005 | Kao et al. |
| 6,908,594 B1 | 6/2005 | Schaevitz et al. |
| 6,911,183 B1 | 6/2005 | Handique et al. |
| 6,914,137 B2 | 7/2005 | Baker |
| 6,915,679 B2 | 7/2005 | Chien et al. |
| 6,918,404 B2 | 7/2005 | Dias da Silva |
| D508,999 S | 8/2005 | Fanning et al. |
| 6,939,451 B2 | 9/2005 | Zhao et al. |
| 6,940,598 B2 | 9/2005 | Christel et al. |
| 6,942,771 B1 | 9/2005 | Kayyem |
| 6,951,632 B2 | 10/2005 | Unger et al. |
| 6,958,392 B2 | 10/2005 | Fomovskaia et al. |
| D512,155 S | 11/2005 | Matsumoto |
| 6,964,747 B2 | 11/2005 | Banerjee et al. |
| 6,977,163 B1 | 12/2005 | Mehta |
| 6,979,424 B2 | 12/2005 | Northrup et al. |
| 6,984,516 B2 | 1/2006 | Briscoe et al. |
| D515,707 S | 2/2006 | Sinohara et al. |
| D516,221 S | 2/2006 | Wohlstadter et al. |
| 7,001,853 B1 | 2/2006 | Brown et al. |
| 7,004,184 B2 | 2/2006 | Handique et al. |
| D517,554 S | 3/2006 | Yanagisawa et al. |
| 7,010,391 B2 | 3/2006 | Handique et al. |
| 7,023,007 B2 | 4/2006 | Gallagher |
| 7,024,281 B1 | 4/2006 | Unno |
| 7,036,667 B2 | 5/2006 | Greenstein et al. |
| 7,037,416 B2 | 5/2006 | Parce et al. |
| 7,038,472 B1 | 5/2006 | Chien |
| 7,039,527 B2 | 5/2006 | Tripathi et al. |
| 7,040,144 B2 | 5/2006 | Spaid et al. |
| 7,041,258 B2 | 5/2006 | Desmond et al. |
| 7,049,558 B2 | 5/2006 | Baer et al. |
| D523,153 S | 6/2006 | Akashi et al. |
| 7,055,695 B2 | 6/2006 | Greenstein et al. |
| 7,060,171 B1 | 6/2006 | Nikiforov et al. |
| 7,066,586 B2 | 6/2006 | Dias da Silva |
| 7,069,952 B1 | 7/2006 | McReynolds et al. |
| 7,072,036 B2 | 7/2006 | Jones et al. |
| 7,099,778 B2 | 8/2006 | Chien |
| D528,215 S | 9/2006 | Malmsater |
| 7,101,467 B2 | 9/2006 | Spaid |
| 7,105,304 B1 | 9/2006 | Nikiforov et al. |
| D531,321 S | 10/2006 | Godfrey et al. |
| 7,118,892 B2 | 10/2006 | Ammann et al. |
| 7,118,910 B2 | 10/2006 | Unger et al. |
| 7,122,799 B2 | 10/2006 | Hsieh et al. |
| 7,135,144 B2 | 11/2006 | Christel et al. |
| 7,138,032 B2 | 11/2006 | Gandhi et al. |
| D534,280 S | 12/2006 | Gomm et al. |
| 7,150,814 B1 | 12/2006 | Parce et al. |
| 7,150,999 B1 | 12/2006 | Shuck |
| D535,403 S | 1/2007 | Isozaki et al. |
| 7,160,423 B2 | 1/2007 | Chien et al. |
| 7,161,356 B1 | 1/2007 | Chien |
| 7,169,277 B2 | 1/2007 | Ausserer et al. |
| 7,169,601 B1 | 1/2007 | Northrup et al. |
| 7,169,618 B2 | 1/2007 | Skold |
| D537,951 S | 3/2007 | Okamoto et al. |
| D538,436 S | 3/2007 | Patadia et al. |
| 7,188,001 B2 | 3/2007 | Young et al. |
| 7,192,557 B2 | 3/2007 | Wu et al. |
| 7,195,986 B1 | 3/2007 | Bousse et al. |
| 7,205,154 B2 | 4/2007 | Corson |
| 7,208,125 B1 | 4/2007 | Dong |
| 7,235,406 B1 | 6/2007 | Woudenberg et al. |
| 7,247,274 B1 | 7/2007 | Chow |
| D548,841 S | 8/2007 | Brownell et al. |
| D549,827 S | 8/2007 | Maeno et al. |
| 7,252,928 B1 | 8/2007 | Hafeman et al. |
| 7,255,833 B2 | 8/2007 | Chang et al. |
| 7,270,786 B2 | 9/2007 | Parunak et al. |
| D554,069 S | 10/2007 | Bolotin et al. |
| D554,070 S | 10/2007 | Bolotin et al. |
| 7,276,208 B2 | 10/2007 | Sevigny et al. |
| 7,276,330 B2 | 10/2007 | Chow et al. |
| 7,288,228 B2 | 10/2007 | Lefebvre |
| 7,297,313 B1 | 11/2007 | Northrup et al. |
| D556,914 S | 12/2007 | Okamoto et al. |
| 7,303,727 B1 | 12/2007 | Dubrow et al. |
| D559,995 S | 1/2008 | Handique et al. |
| 7,315,376 B2 | 1/2008 | Bickmore et al. |
| 7,323,140 B2 | 1/2008 | Handique et al. |
| 7,332,130 B2 | 2/2008 | Handique |
| 7,338,760 B2 | 3/2008 | Gong et al. |
| D566,291 S | 4/2008 | Parunak et al. |
| 7,351,377 B2 | 4/2008 | Chazan et al. |
| D569,526 S | 5/2008 | Duffy et al. |
| 7,374,949 B2 | 5/2008 | Kuriger |
| 7,390,460 B2 | 6/2008 | Osawa et al. |
| 7,419,784 B2 | 9/2008 | Dubrow et al. |
| 7,422,669 B2 | 9/2008 | Jacobson et al. |
| 7,440,684 B2 | 10/2008 | Spaid et al. |
| 7,476,313 B2 | 1/2009 | Siddiqi |
| 7,480,042 B1 | 1/2009 | Phillips et al. |
| 7,494,577 B2 | 2/2009 | Williams et al. |
| 7,494,770 B2 | 2/2009 | Wilding et al. |
| 7,514,046 B2 | 4/2009 | Kechagia et al. |
| 7,518,726 B2 | 4/2009 | Rulison et al. |
| 7,521,186 B2 | 4/2009 | Burd Mehta |
| 7,527,769 B2 | 5/2009 | Bunch et al. |
| D595,423 S | 6/2009 | Johansson et al. |
| 7,553,671 B2 | 6/2009 | Sinclair et al. |
| D596,312 S | 7/2009 | Giraud et al. |

(56) References Cited

U.S. PATENT DOCUMENTS

| | | |
|---|---|---|
| D598,566 S | 8/2009 | Allaer |
| 7,578,976 B1 | 8/2009 | Northrup et al. |
| D599,234 S | 9/2009 | Ito |
| 7,595,197 B2 | 9/2009 | Brasseur |
| 7,604,938 B2 | 10/2009 | Takahashi et al. |
| 7,622,296 B2 | 11/2009 | Joseph et al. |
| 7,628,902 B2 | 12/2009 | Knowlton et al. |
| 7,633,606 B2 | 12/2009 | Northrup et al. |
| 7,635,588 B2 | 12/2009 | King et al. |
| 7,645,581 B2 | 1/2010 | Knapp et al. |
| 7,670,559 B2 | 3/2010 | Chien et al. |
| 7,674,431 B2 | 3/2010 | Ganesan |
| 7,689,022 B2 | 3/2010 | Weiner et al. |
| 7,704,735 B2 | 4/2010 | Facer et al. |
| 7,705,739 B2 | 4/2010 | Northrup et al. |
| 7,723,123 B1 | 5/2010 | Murphy et al. |
| D618,820 S | 6/2010 | Wilson et al. |
| 7,727,371 B2 | 6/2010 | Kennedy et al. |
| 7,727,477 B2 | 6/2010 | Boronkay et al. |
| 7,744,817 B2 | 6/2010 | Bui |
| D621,060 S | 8/2010 | Handique |
| 7,785,868 B2 | 8/2010 | Yuan et al. |
| D628,305 S | 11/2010 | Gorrec et al. |
| 7,829,025 B2 | 11/2010 | Ganesan et al. |
| 7,858,366 B2 | 12/2010 | Northrup et al. |
| 7,867,776 B2 | 1/2011 | Kennedy et al. |
| 7,892,819 B2 | 2/2011 | Wilding et al. |
| D637,737 S | 5/2011 | Wilson et al. |
| 7,955,864 B2 | 6/2011 | Cox et al. |
| 7,987,022 B2 | 7/2011 | Handique et al. |
| 7,998,708 B2 | 8/2011 | Handique et al. |
| 8,053,214 B2 | 11/2011 | Northrup |
| 8,071,056 B2 | 12/2011 | Burns et al. |
| 8,088,616 B2 | 1/2012 | Handique |
| 8,105,783 B2 | 1/2012 | Handique |
| 8,110,158 B2 | 2/2012 | Handique |
| 8,133,671 B2 | 3/2012 | Williams et al. |
| 8,182,763 B2 | 5/2012 | Duffy et al. |
| 8,246,919 B2 | 8/2012 | Herchenbach et al. |
| 8,273,308 B2 | 9/2012 | Handique et al. |
| D669,597 S | 10/2012 | Cavada et al. |
| 8,287,820 B2 | 10/2012 | Williams et al. |
| 8,323,584 B2 | 12/2012 | Ganesan |
| 8,323,900 B2 | 12/2012 | Handique et al. |
| 8,324,372 B2 | 12/2012 | Brahmasandra et al. |
| 8,415,103 B2 | 4/2013 | Handique |
| 8,420,015 B2 | 4/2013 | Ganesan et al. |
| 8,440,149 B2 | 5/2013 | Handique |
| 8,470,586 B2 | 6/2013 | Wu et al. |
| 8,473,104 B2 | 6/2013 | Handique et al. |
| D686,749 S | 7/2013 | Trump |
| D687,567 S | 8/2013 | Jungheim et al. |
| D692,162 S | 10/2013 | Lentz et al. |
| 8,592,157 B2 | 11/2013 | Petersen et al. |
| 8,679,831 B2 | 3/2014 | Handique et al. |
| D702,854 S | 4/2014 | Nakahana et al. |
| 8,685,341 B2 | 4/2014 | Ganesan |
| 8,703,069 B2 | 4/2014 | Handique et al. |
| 8,709,787 B2 | 4/2014 | Handique |
| 8,710,211 B2 | 4/2014 | Brahmasandra et al. |
| 8,734,733 B2 | 5/2014 | Handique |
| D710,024 S | 7/2014 | Guo |
| 8,765,076 B2 | 7/2014 | Handique et al. |
| 8,765,454 B2 | 7/2014 | Zhou et al. |
| 8,768,517 B2 | 7/2014 | Handique et al. |
| 8,852,862 B2 | 10/2014 | Wu et al. |
| 8,883,490 B2 | 11/2014 | Handique et al. |
| 8,894,947 B2 | 11/2014 | Ganesan et al. |
| 8,895,311 B1 | 11/2014 | Handique et al. |
| D729,404 S | 5/2015 | Teich et al. |
| 9,028,773 B2 | 5/2015 | Ganesan |
| 9,040,288 B2 | 5/2015 | Handique et al. |
| 9,051,604 B2 | 6/2015 | Handique |
| 9,080,207 B2 | 7/2015 | Handique et al. |
| D742,027 S | 10/2015 | Lentz et al. |
| 9,186,677 B2 | 11/2015 | Williams et al. |
| 9,217,143 B2 | 12/2015 | Brahmasandra et al. |
| 9,222,954 B2 | 12/2015 | Lentz et al. |
| 9,234,236 B2 | 1/2016 | Thomas et al. |
| 9,238,223 B2 | 1/2016 | Handique |
| 9,259,734 B2 | 2/2016 | Williams et al. |
| 9,259,735 B2 | 2/2016 | Handique et al. |
| 9,347,586 B2 | 5/2016 | Williams et al. |
| 9,480,983 B2 | 11/2016 | Lentz et al. |
| 9,528,142 B2 | 12/2016 | Handique |
| 9,618,139 B2 | 4/2017 | Handique |
| D787,087 S | 6/2017 | Duffy et al. |
| 9,670,528 B2 | 6/2017 | Handique et al. |
| 9,677,121 B2 | 6/2017 | Ganesan et al. |
| 9,701,957 B2 | 7/2017 | Wilson et al. |
| 9,745,623 B2 | 8/2017 | Steel |
| 9,765,389 B2 | 9/2017 | Gubatayao et al. |
| 9,789,481 B2 | 10/2017 | Petersen et al. |
| 9,802,199 B2 | 10/2017 | Handique et al. |
| 9,815,057 B2 | 11/2017 | Handique |
| 9,958,466 B2 | 5/2018 | Dalbert et al. |
| 10,065,185 B2 | 9/2018 | Handique |
| 10,071,376 B2 | 9/2018 | Williams et al. |
| 10,076,754 B2 | 9/2018 | Lentz et al. |
| 10,100,302 B2 | 10/2018 | Brahmasandra et al. |
| 10,139,012 B2 | 11/2018 | Handique |
| 10,179,910 B2 | 1/2019 | Duffy et al. |
| 10,234,474 B2 | 3/2019 | Williams et al. |
| 10,351,901 B2 | 7/2019 | Ganesan et al. |
| 10,364,456 B2 | 7/2019 | Wu et al. |
| 10,443,088 B1 | 10/2019 | Wu et al. |
| 10,494,663 B1 | 12/2019 | Wu et al. |
| 10,571,935 B2 | 2/2020 | Handique et al. |
| 10,590,410 B2 | 3/2020 | Brahmasandra et al. |
| 10,604,788 B2 | 3/2020 | Wu et al. |
| 10,619,191 B2 | 4/2020 | Ganesan et al. |
| 10,625,261 B2 | 4/2020 | Williams et al. |
| 10,625,262 B2 | 4/2020 | Williams et al. |
| 10,632,466 B1 | 4/2020 | Williams et al. |
| 10,695,764 B2 | 6/2020 | Handique et al. |
| 10,710,069 B2 | 7/2020 | Handique et al. |
| 10,717,085 B2 | 7/2020 | Williams et al. |
| 10,731,201 B2 | 8/2020 | Handique et al. |
| 10,781,482 B2 | 9/2020 | Gubatayao et al. |
| 10,799,862 B2 | 10/2020 | Handique et al. |
| 10,821,436 B2 | 11/2020 | Handique et al. |
| 10,821,446 B1 | 11/2020 | Handique et al. |
| 10,822,644 B2 | 11/2020 | Steel et al. |
| 10,843,188 B2 | 11/2020 | Handique et al. |
| 10,844,368 B2 | 11/2020 | Duffy et al. |
| 10,857,535 B2 | 12/2020 | Handique et al. |
| 10,865,437 B2 | 12/2020 | Handique et al. |
| 10,875,022 B2 | 12/2020 | Williams et al. |
| 10,900,066 B2 | 1/2021 | Handique et al. |
| 10,913,061 B2 | 2/2021 | Handique et al. |
| 11,060,082 B2 | 7/2021 | Brahmasandra et al. |
| 11,078,523 B2 | 8/2021 | Handique et al. |
| 11,085,069 B2 | 8/2021 | Handique et al. |
| 11,141,734 B2 | 10/2021 | Handique et al. |
| 11,142,785 B2 | 10/2021 | Handique et al. |
| 11,254,927 B2 | 2/2022 | Brahmasandra et al. |
| 11,266,987 B2 | 3/2022 | Handique |
| 2001/0005489 A1 | 6/2001 | Roach et al. |
| 2001/0012492 A1 | 8/2001 | Acosta et al. |
| 2001/0016358 A1 | 8/2001 | Osawa et al. |
| 2001/0018513 A1 | 8/2001 | Baker |
| 2001/0021355 A1 | 9/2001 | Baugh et al. |
| 2001/0023848 A1 | 9/2001 | Gjerde et al. |
| 2001/0038450 A1 | 11/2001 | McCaffrey et al. |
| 2001/0045358 A1 | 11/2001 | Kopf-Sill et al. |
| 2001/0046702 A1 | 11/2001 | Schembri |
| 2001/0048899 A1 | 12/2001 | Marouiss et al. |
| 2001/0051340 A1 | 12/2001 | Singh et al. |
| 2001/0055765 A1 | 12/2001 | O'Keefe et al. |
| 2002/0001848 A1 | 1/2002 | Bedingham et al. |
| 2002/0008053 A1 | 1/2002 | Hansen et al. |
| 2002/0009015 A1 | 1/2002 | Laugharn, Jr. et al. |
| 2002/0014443 A1 | 2/2002 | Hansen et al. |
| 2002/0015667 A1 | 2/2002 | Chow |

(56) References Cited

U.S. PATENT DOCUMENTS

| | | |
|---|---|---|
| 2002/0021983 A1 | 2/2002 | Comte et al. |
| 2002/0022261 A1 | 2/2002 | Anderson et al. |
| 2002/0037499 A1 | 3/2002 | Quake et al. |
| 2002/0039783 A1 | 4/2002 | McMillan et al. |
| 2002/0047003 A1 | 4/2002 | Bedingham et al. |
| 2002/0053399 A1 | 5/2002 | Soane et al. |
| 2002/0054835 A1 | 5/2002 | Robotti et al. |
| 2002/0055167 A1 | 5/2002 | Pourahmadi et al. |
| 2002/0058332 A1 | 5/2002 | Quake et al. |
| 2002/0060156 A1 | 5/2002 | Mathies et al. |
| 2002/0068357 A1 | 6/2002 | Mathies et al. |
| 2002/0068821 A1 | 6/2002 | Gundling |
| 2002/0086443 A1 | 7/2002 | Bamdad |
| 2002/0090320 A1 | 7/2002 | Burow et al. |
| 2002/0092767 A1 | 7/2002 | Bjornson et al. |
| 2002/0094303 A1 | 7/2002 | Yamamoto et al. |
| 2002/0131903 A1 | 9/2002 | Ingenhoven et al. |
| 2002/0141903 A1 | 10/2002 | Parunak et al. |
| 2002/0143297 A1 | 10/2002 | Francavilla et al. |
| 2002/0155010 A1 | 10/2002 | Karp et al. |
| 2002/0155477 A1 | 10/2002 | Ito |
| 2002/0169518 A1 | 11/2002 | Luoma et al. |
| 2002/0173032 A1 | 11/2002 | Zou et al. |
| 2002/0176804 A1 | 11/2002 | Strand et al. |
| 2002/0187557 A1 | 12/2002 | Hobbs et al. |
| 2002/0192808 A1 | 12/2002 | Gambini et al. |
| 2003/0008308 A1 | 1/2003 | Enzelberger et al. |
| 2003/0008320 A1 | 1/2003 | Baker |
| 2003/0019522 A1 | 1/2003 | Parunak |
| 2003/0022392 A1 | 1/2003 | Hudak |
| 2003/0036067 A1 | 2/2003 | Schwartz |
| 2003/0049833 A1 | 3/2003 | Chen et al. |
| 2003/0059823 A1 | 3/2003 | Matsunaga et al. |
| 2003/0064507 A1 | 4/2003 | Gallagher et al. |
| 2003/0072683 A1 | 4/2003 | Stewart et al. |
| 2003/0073106 A1 | 4/2003 | Johansen et al. |
| 2003/0073110 A1 | 4/2003 | Aritomi et al. |
| 2003/0083686 A1 | 5/2003 | Freeman et al. |
| 2003/0087300 A1 | 5/2003 | Knapp et al. |
| 2003/0088657 A1 | 5/2003 | Eggers |
| 2003/0096310 A1 | 5/2003 | Hansen et al. |
| 2003/0099954 A1 | 5/2003 | Miltenyi et al. |
| 2003/0124611 A1 | 7/2003 | Schwartz |
| 2003/0127327 A1 | 7/2003 | Kurnik |
| 2003/0134333 A1 | 7/2003 | Dehlinger et al. |
| 2003/0136679 A1 | 7/2003 | Bohn et al. |
| 2003/0156991 A1 | 8/2003 | Halas et al. |
| 2003/0180192 A1 | 9/2003 | Seippel |
| 2003/0186295 A1 | 10/2003 | Colin et al. |
| 2003/0190608 A1 | 10/2003 | Blackburn et al. |
| 2003/0199081 A1 | 10/2003 | Wilding et al. |
| 2003/0211517 A1 | 11/2003 | Carulli et al. |
| 2004/0014202 A1 | 1/2004 | King et al. |
| 2004/0014238 A1 | 1/2004 | Krug et al. |
| 2004/0018116 A1 | 1/2004 | Desmond et al. |
| 2004/0018119 A1 | 1/2004 | Massaro |
| 2004/0022689 A1 | 2/2004 | Wulf et al. |
| 2004/0029258 A1 | 2/2004 | Heaney et al. |
| 2004/0029260 A1 | 2/2004 | Hansen et al. |
| 2004/0037739 A1 | 2/2004 | McNeely et al. |
| 2004/0043479 A1 | 3/2004 | Briscoe et al. |
| 2004/0053290 A1 | 3/2004 | Terbrueggen et al. |
| 2004/0063217 A1 | 4/2004 | Webster et al. |
| 2004/0065655 A1 | 4/2004 | Brown |
| 2004/0072278 A1 | 4/2004 | Chou et al. |
| 2004/0072375 A1 | 4/2004 | Gjerde et al. |
| 2004/0076996 A1 | 4/2004 | Kondo et al. |
| 2004/0086427 A1 | 5/2004 | Childers et al. |
| 2004/0086956 A1 | 5/2004 | Bachur |
| 2004/0132059 A1 | 7/2004 | Scurati et al. |
| 2004/0141887 A1 | 7/2004 | Mainquist et al. |
| 2004/0151629 A1 | 8/2004 | Pease et al. |
| 2004/0157220 A1 | 8/2004 | Kurnool et al. |
| 2004/0161788 A1 | 8/2004 | Chen et al. |
| 2004/0171515 A1 | 9/2004 | Hamers et al. |
| 2004/0189311 A1 | 9/2004 | Glezer et al. |
| 2004/0197810 A1 | 10/2004 | Takenaka et al. |
| 2004/0200909 A1 | 10/2004 | McMillan et al. |
| 2004/0209331 A1 | 10/2004 | Ririe |
| 2004/0209354 A1 | 10/2004 | Mathies et al. |
| 2004/0224317 A1 | 11/2004 | Kordunsky et al. |
| 2004/0235154 A1 | 11/2004 | Oh et al. |
| 2004/0240097 A1 | 12/2004 | Evans |
| 2005/0009174 A1 | 1/2005 | Nikiforov et al. |
| 2005/0013737 A1 | 1/2005 | Chow et al. |
| 2005/0019902 A1 | 1/2005 | Mathies et al. |
| 2005/0037471 A1 | 2/2005 | Liu et al. |
| 2005/0041525 A1 | 2/2005 | Pugia et al. |
| 2005/0042639 A1 | 2/2005 | Knapp et al. |
| 2005/0048540 A1 | 3/2005 | Inami et al. |
| 2005/0058574 A1 | 3/2005 | Bysouth et al. |
| 2005/0058577 A1 | 3/2005 | Micklash et al. |
| 2005/0064535 A1 | 3/2005 | Favuzzi et al. |
| 2005/0069898 A1 | 3/2005 | Moon et al. |
| 2005/0084424 A1 | 4/2005 | Ganesan et al. |
| 2005/0106066 A1 | 5/2005 | Saltsman et al. |
| 2005/0112754 A1 | 5/2005 | Yoon et al. |
| 2005/0121324 A1 | 6/2005 | Park et al. |
| 2005/0129580 A1 | 6/2005 | Swinehart et al. |
| 2005/0130198 A1 | 6/2005 | Ammann et al. |
| 2005/0133370 A1 | 6/2005 | Park et al. |
| 2005/0135655 A1 | 6/2005 | Kopf-sill et al. |
| 2005/0142036 A1 | 6/2005 | Kim et al. |
| 2005/0158781 A1 | 7/2005 | Woudenberg et al. |
| 2005/0170362 A1 | 8/2005 | Wada et al. |
| 2005/0186585 A1 | 8/2005 | Juncosa et al. |
| 2005/0196321 A1 | 9/2005 | Huang |
| 2005/0202470 A1 | 9/2005 | Sundberg et al. |
| 2005/0202489 A1 | 9/2005 | Cho et al. |
| 2005/0202504 A1 | 9/2005 | Anderson et al. |
| 2005/0205788 A1 | 9/2005 | Itoh |
| 2005/0208676 A1 | 9/2005 | Kahatt |
| 2005/0214172 A1 | 9/2005 | Burgisser |
| 2005/0220675 A1 | 10/2005 | Reed et al. |
| 2005/0227269 A1 | 10/2005 | Lloyd et al. |
| 2005/0233370 A1 | 10/2005 | Ammann et al. |
| 2005/0238545 A1 | 10/2005 | Parce et al. |
| 2005/0239127 A1 | 10/2005 | Ammann et al. |
| 2005/0266489 A1 | 12/2005 | Ammann et al. |
| 2005/0276728 A1 | 12/2005 | Muller-Cohn et al. |
| 2006/0002817 A1 | 1/2006 | Bohm et al. |
| 2006/0003373 A1 | 1/2006 | Ammann et al. |
| 2006/0041058 A1 | 2/2006 | Yin et al. |
| 2006/0057039 A1 | 3/2006 | Morse et al. |
| 2006/0057629 A1 | 3/2006 | Kim |
| 2006/0058519 A1 | 3/2006 | Deggerdal et al. |
| 2006/0062696 A1 | 3/2006 | Chow et al. |
| 2006/0081539 A1 | 4/2006 | Safar et al. |
| 2006/0094004 A1 | 5/2006 | Nakajima et al. |
| 2006/0094108 A1 | 5/2006 | Yoder et al. |
| 2006/0113190 A1 | 6/2006 | Kurnik |
| 2006/0133965 A1 | 6/2006 | Tajima et al. |
| 2006/0134790 A1 | 6/2006 | Tanaka et al. |
| 2006/0148063 A1 | 7/2006 | Fauzzi et al. |
| 2006/0154341 A1 | 7/2006 | Chen |
| 2006/0165558 A1 | 7/2006 | Witty et al. |
| 2006/0165559 A1 | 7/2006 | Greenstein et al. |
| 2006/0177376 A1 | 8/2006 | Tomalia et al. |
| 2006/0177855 A1 | 8/2006 | Utermohlen et al. |
| 2006/0183216 A1 | 8/2006 | Handique |
| 2006/0201887 A1 | 9/2006 | Siddiqi |
| 2006/0205085 A1 | 9/2006 | Handique |
| 2006/0207944 A1 | 9/2006 | Siddiqi |
| 2006/0210435 A1 | 9/2006 | Alavie et al. |
| 2006/0223169 A1 | 10/2006 | Bedingham et al. |
| 2006/0228734 A1 | 10/2006 | Vann et al. |
| 2006/0246493 A1 | 11/2006 | Jensen et al. |
| 2006/0246533 A1 | 11/2006 | Fathollahi et al. |
| 2006/0269641 A1 | 11/2006 | Atwood et al. |
| 2006/0269961 A1 | 11/2006 | Fukushima et al. |
| 2007/0004028 A1 | 1/2007 | Lair et al. |
| 2007/0009386 A1 | 1/2007 | Padmanabhan et al. |
| 2007/0014695 A1 | 1/2007 | Yue et al. |
| 2007/0020699 A1 | 1/2007 | Carpenter et al. |

(56) References Cited

U.S. PATENT DOCUMENTS

| | | |
|---|---|---|
| 2007/0020764 A1 | 1/2007 | Miller |
| 2007/0026421 A1 | 2/2007 | Sundberg et al. |
| 2007/0042441 A1 | 2/2007 | Masters et al. |
| 2007/0048188 A1 | 3/2007 | Bigus |
| 2007/0054413 A1 | 3/2007 | Aviles et al. |
| 2007/0077643 A1 | 4/2007 | Nakamura et al. |
| 2007/0077648 A1 | 4/2007 | Okamoto et al. |
| 2007/0092901 A1 | 4/2007 | Ligler et al. |
| 2007/0098600 A1 | 5/2007 | Kayyem et al. |
| 2007/0099200 A1 | 5/2007 | Chow et al. |
| 2007/0104617 A1 | 5/2007 | Coulling et al. |
| 2007/0116613 A1 | 5/2007 | Elsener |
| 2007/0154895 A1 | 7/2007 | Spaid et al. |
| 2007/0177147 A1 | 8/2007 | Parce |
| 2007/0178607 A1 | 8/2007 | Prober et al. |
| 2007/0184463 A1 | 8/2007 | Molho et al. |
| 2007/0184547 A1 | 8/2007 | Handique et al. |
| 2007/0196237 A1 | 8/2007 | Neuzil et al. |
| 2007/0196238 A1 | 8/2007 | Kennedy et al. |
| 2007/0199821 A1 | 8/2007 | Chow |
| 2007/0215554 A1 | 9/2007 | Kreuwel et al. |
| 2007/0218459 A1 | 9/2007 | Miller et al. |
| 2007/0231213 A1 | 10/2007 | Prabhu et al. |
| 2007/0243626 A1 | 10/2007 | Windeyer et al. |
| 2007/0248958 A1 | 10/2007 | Jovanovich et al. |
| 2007/0261479 A1 | 11/2007 | Spaid et al. |
| 2007/0269861 A1 | 11/2007 | Williams et al. |
| 2007/0292941 A1 | 12/2007 | Handique et al. |
| 2008/0000774 A1 | 1/2008 | Park et al. |
| 2008/0003649 A1 | 1/2008 | Maltezos et al. |
| 2008/0017306 A1 | 1/2008 | Liu et al. |
| 2008/0056948 A1 | 3/2008 | Dale et al. |
| 2008/0069729 A1 | 3/2008 | McNeely |
| 2008/0090244 A1 | 4/2008 | Knapp et al. |
| 2008/0095673 A1 | 4/2008 | Xu |
| 2008/0118987 A1 | 5/2008 | Eastwood et al. |
| 2008/0124723 A1 | 5/2008 | Dale et al. |
| 2008/0176230 A1 | 7/2008 | Owen et al. |
| 2008/0192254 A1 | 8/2008 | Kim et al. |
| 2008/0226502 A1 | 9/2008 | Jonsmann et al. |
| 2008/0240898 A1 | 10/2008 | Manz et al. |
| 2008/0247914 A1 | 10/2008 | Edens et al. |
| 2008/0257882 A1 | 10/2008 | Turner |
| 2008/0280285 A1 | 11/2008 | Chen et al. |
| 2008/0308500 A1 | 12/2008 | Brassard |
| 2009/0047180 A1 | 2/2009 | Kawahara |
| 2009/0066339 A1 | 3/2009 | Glezer et al. |
| 2009/0136385 A1 | 5/2009 | Handique et al. |
| 2009/0148933 A1 | 6/2009 | Battrell et al. |
| 2009/0189089 A1 | 7/2009 | Bedingham et al. |
| 2009/0223925 A1 | 9/2009 | Morse et al. |
| 2009/0325164 A1 | 12/2009 | Vossenaar et al. |
| 2009/0325276 A1 | 12/2009 | Battrell et al. |
| 2010/0009343 A1 | 1/2010 | Fischer et al. |
| 2010/0009351 A1 | 1/2010 | Brahmasandra et al. |
| 2010/0120129 A1 | 5/2010 | Amshey et al. |
| 2010/0233763 A1 | 9/2010 | Shigeura et al. |
| 2010/0284864 A1 | 11/2010 | Holenstein et al. |
| 2011/0008825 A1 | 1/2011 | Ingber et al. |
| 2011/0027151 A1 | 2/2011 | Handique et al. |
| 2011/0060136 A1 | 3/2011 | Matsunaga et al. |
| 2011/0097493 A1 | 4/2011 | Kerr et al. |
| 2011/0127292 A1 | 6/2011 | Sarofim et al. |
| 2011/0158865 A1 | 6/2011 | Miller et al. |
| 2011/0287447 A1 | 11/2011 | Norderhaug |
| 2011/0300033 A1 | 12/2011 | Battisti |
| 2012/0122231 A1 | 5/2012 | Tajima |
| 2012/0160826 A1 | 6/2012 | Handique |
| 2012/0171678 A1 | 7/2012 | Maltezos et al. |
| 2012/0258463 A1 | 10/2012 | Duffy et al. |
| 2013/0183769 A1 | 7/2013 | Tajima |
| 2013/0210127 A1 | 8/2013 | Williams et al. |
| 2013/0315800 A1 | 11/2013 | Yin et al. |
| 2014/0030798 A1 | 1/2014 | Wu et al. |
| 2014/0120544 A1 | 5/2014 | Brahmasandra et al. |
| 2014/0227710 A1 | 8/2014 | Handique et al. |
| 2014/0329301 A1 | 11/2014 | Handique et al. |
| 2015/0045234 A1 | 2/2015 | Stone et al. |
| 2015/0174579 A1 | 6/2015 | Iten et al. |
| 2015/0315631 A1 | 11/2015 | Handique et al. |
| 2016/0038942 A1 | 2/2016 | Roberts |
| 2017/0275702 A1 | 9/2017 | Dahiya et al. |
| 2018/0333722 A1 | 11/2018 | Handique |
| 2019/0054467 A1 | 2/2019 | Handique |
| 2019/0054471 A1 | 2/2019 | Williams et al. |
| 2019/0144849 A1 | 5/2019 | Duffy et al. |
| 2019/0145546 A1 | 5/2019 | Handique |
| 2019/0151854 A1 | 5/2019 | Baum et al. |
| 2019/0154719 A1 | 5/2019 | LaChance et al. |
| 2019/0284606 A1 | 9/2019 | Wu et al. |
| 2019/0324050 A1 | 10/2019 | Williams et al. |
| 2020/0139363 A1 | 5/2020 | Handique et al. |
| 2020/0156060 A1 | 5/2020 | Handique et al. |
| 2020/0216831 A1 | 7/2020 | Brahmasandra et al. |
| 2020/0291388 A1 | 9/2020 | Brahmasandra et al. |
| 2020/0325523 A1 | 10/2020 | Brahmasandra et al. |
| 2020/0325524 A1 | 10/2020 | Handique et al. |
| 2021/0001334 A1 | 1/2021 | Handique et al. |
| 2021/0010059 A1 | 1/2021 | Handique et al. |
| 2021/0060565 A1 | 3/2021 | Handique et al. |
| 2021/0071234 A1 | 3/2021 | Gubatayao et al. |
| 2021/0087609 A1 | 3/2021 | Handique et al. |
| 2021/0121887 A1 | 4/2021 | Handique et al. |
| 2021/0123090 A1 | 4/2021 | Handique et al. |
| 2021/0147923 A1 | 5/2021 | Steel et al. |
| 2021/0276008 A1 | 9/2021 | Handique et al. |
| 2021/0299663 A1 | 9/2021 | Handique |
| 2021/0317437 A1 | 10/2021 | Duffy et al. |
| 2021/0362155 A1 | 11/2021 | Williams et al. |
| 2022/0010364 A1 | 1/2022 | Handique et al. |

FOREIGN PATENT DOCUMENTS

| | | |
|---|---|---|
| AU | 4437602 | 7/2002 |
| AU | 4437702 | 7/2002 |
| AU | 764319 B2 | 8/2003 |
| CA | 2574107 | 9/1998 |
| CA | 2294819 | 1/1999 |
| CN | 1934451 | 3/2007 |
| CN | 1312287 C | 4/2007 |
| CN | 1942590 A | 4/2007 |
| CN | 1968754 A | 5/2007 |
| CN | 101466848 | 6/2009 |
| CN | 101522909 | 9/2009 |
| CN | 103540518 | 1/2014 |
| DE | 19755479 A1 | 6/1999 |
| DE | 19929734 | 12/1999 |
| DE | 19833293 C1 | 1/2000 |
| EP | 0136126 A2 | 4/1985 |
| EP | 0365828 A2 | 5/1990 |
| EP | 0483620 A2 | 5/1992 |
| EP | 0402994 B1 | 11/1994 |
| EP | 0393744 B1 | 1/1995 |
| EP | 0688602 A2 | 12/1995 |
| EP | 0707077 A2 | 4/1996 |
| EP | 0698046 B1 | 3/1997 |
| EP | 0766256 | 4/1997 |
| EP | 0772494 B1 | 5/1997 |
| EP | 0810030 A1 | 12/1997 |
| EP | 1059458 A2 | 12/2000 |
| EP | 1064090 A1 | 1/2001 |
| EP | 1077086 A2 | 2/2001 |
| EP | 1346772 A2 | 9/2003 |
| EP | 1541237 A2 | 6/2005 |
| EP | 1574586 A2 | 9/2005 |
| EP | 1621890 A1 | 2/2006 |
| EP | 1745153 | 1/2007 |
| EP | 1780290 A2 | 5/2007 |
| EP | 1792656 A1 | 6/2007 |
| EP | 2372367 A1 | 10/2011 |
| FR | 2672301 | 8/1992 |
| FR | 2795426 | 12/2000 |
| GB | 2453432 A | 4/2009 |
| JP | S50-100881 | 8/1975 |

(56) References Cited

FOREIGN PATENT DOCUMENTS

| | | |
|---|---|---|
| JP | 58212921 A | 12/1983 |
| JP | S62-119460 | 5/1987 |
| JP | H01-502319 | 8/1989 |
| JP | H03181853 | 8/1991 |
| JP | 04-053555 U | 5/1992 |
| JP | 06-064156 U | 9/1994 |
| JP | 07-020010 | 1/1995 |
| JP | H07-290706 | 11/1995 |
| JP | H08-122336 | 5/1996 |
| JP | H08-173194 | 7/1996 |
| JP | H08-211071 | 8/1996 |
| JP | H08-285859 | 11/1996 |
| JP | H08-337116 | 12/1996 |
| JP | H09-304385 | 11/1997 |
| JP | H09-325151 | 12/1997 |
| JP | 2001-502790 | 1/1998 |
| JP | H01-219669 | 9/1998 |
| JP | H10-327515 | 12/1998 |
| JP | H11-009258 | 1/1999 |
| JP | H11-501504 | 2/1999 |
| JP | H11-503315 | 3/1999 |
| JP | 2000-514928 | 4/1999 |
| JP | H11-156231 | 6/1999 |
| JP | H11-316226 | 11/1999 |
| JP | H11-515106 | 12/1999 |
| JP | 2000-180455 | 6/2000 |
| JP | 2000-266760 | 9/2000 |
| JP | 2000-275255 | 10/2000 |
| JP | 2001-502319 | 2/2001 |
| JP | 2001-204462 | 7/2001 |
| JP | 2001-509437 | 7/2001 |
| JP | 3191150 B2 | 7/2001 |
| JP | 2001-515216 | 9/2001 |
| JP | 2001-523812 | 11/2001 |
| JP | 2001-527220 | 12/2001 |
| JP | 2002-503331 | 1/2002 |
| JP | 2002-085961 | 3/2002 |
| JP | 2002-517735 | 6/2002 |
| JP | 2002-215241 | 7/2002 |
| JP | 2002-540382 | 11/2002 |
| JP | 2002-544476 | 12/2002 |
| JP | 2003-500674 | 1/2003 |
| JP | 2003-047839 A | 2/2003 |
| JP | 2003-047840 A | 2/2003 |
| JP | 2003-516125 | 5/2003 |
| JP | 2003-164279 | 6/2003 |
| JP | 2003-185584 | 7/2003 |
| JP | 2003-299485 | 10/2003 |
| JP | 2003-329693 | 11/2003 |
| JP | 2003-329696 | 11/2003 |
| JP | 2003-532382 A | 11/2003 |
| JP | 2004-003989 | 1/2004 |
| JP | 2004-506179 A | 2/2004 |
| JP | 2004-150797 A | 5/2004 |
| JP | 2004-283728 A | 10/2004 |
| JP | 2004-531360 A | 10/2004 |
| JP | 2004-533838 | 11/2004 |
| JP | 2004-534157 | 11/2004 |
| JP | 2004-361421 | 12/2004 |
| JP | 2004-536291 | 12/2004 |
| JP | 2004-536689 A | 12/2004 |
| JP | 2005-009870 | 1/2005 |
| JP | 2005-010179 | 1/2005 |
| JP | 2005-511264 | 4/2005 |
| JP | 2005-514718 | 5/2005 |
| JP | 2005-518825 | 6/2005 |
| JP | 2005-176613 A | 7/2005 |
| JP | 2005-192439 | 7/2005 |
| JP | 2005-192554 | 7/2005 |
| JP | 2005-519751 | 7/2005 |
| JP | 2005-204661 | 8/2005 |
| JP | 2005-525816 | 9/2005 |
| JP | 2005-291954 A | 10/2005 |
| JP | 2005-532043 | 10/2005 |
| JP | 2005-323519 | 11/2005 |
| JP | 2005-533652 | 11/2005 |
| JP | 2005-535904 | 11/2005 |
| JP | 2006-021156 A | 1/2006 |
| JP | 2006-055837 A | 3/2006 |
| JP | 2006-094866 A | 4/2006 |
| JP | 2006-145458 | 6/2006 |
| JP | 2006-167569 | 6/2006 |
| JP | 2006-284409 | 10/2006 |
| JP | 2007-024742 A | 2/2007 |
| JP | 2007-074960 | 3/2007 |
| JP | 2007-097477 | 4/2007 |
| JP | 2007-101364 | 4/2007 |
| JP | 2007-510518 | 4/2007 |
| JP | 2007-514405 A | 6/2007 |
| JP | 2007-178328 | 7/2007 |
| JP | 2007-535933 | 12/2007 |
| JP | 2009-515140 | 4/2009 |
| JP | 2009-542207 | 12/2009 |
| JP | 3193848 U | 10/2014 |
| KR | 1020060044489 A | 5/2006 |
| RU | 2418633 C2 | 5/2011 |
| WO | WO 1988/006633 | 9/1988 |
| WO | WO 1990/012350 | 10/1990 |
| WO | WO 1992/005443 | 4/1992 |
| WO | WO 1994/005414 | 3/1994 |
| WO | WO 1994/011103 | 5/1994 |
| WO | WO 1995/033846 | 12/1995 |
| WO | WO 1996/000228 | 1/1996 |
| WO | WO 1996/004547 | 2/1996 |
| WO | WO 1996/018731 | 6/1996 |
| WO | WO 1996/039547 | 12/1996 |
| WO | WO 1997/005492 | 2/1997 |
| WO | WO 1997/016835 | 5/1997 |
| WO | WO 1997/021090 | 6/1997 |
| WO | WO 1997/022825 | 6/1997 |
| WO | WO 1997/027324 | 7/1997 |
| WO | WO 1998/000231 | 1/1998 |
| WO | WO 1998/007019 | 2/1998 |
| WO | WO 1998/022625 | 5/1998 |
| WO | WO 1998/035013 | 8/1998 |
| WO | WO 1998/038487 | 9/1998 |
| WO | WO 1998/049548 | 11/1998 |
| WO | WO 1998/050147 | 11/1998 |
| WO | WO 1998/053311 | 11/1998 |
| WO | WO 1999/001688 | 1/1999 |
| WO | WO 1999/009042 | 2/1999 |
| WO | WO 1999/012016 | 3/1999 |
| WO | WO 1999/017093 | 4/1999 |
| WO | WO 1999/029703 | 6/1999 |
| WO | WO 1999/033559 | 7/1999 |
| WO | WO 1999/060397 | 11/1999 |
| WO | WO 2000/022436 | 4/2000 |
| WO | WO 2000/066783 | 11/2000 |
| WO | WO 2000/073412 | 12/2000 |
| WO | WO 2000/075623 | 12/2000 |
| WO | WO 2000/078455 | 12/2000 |
| WO | WO 2001/005510 | 1/2001 |
| WO | WO 2001/014931 | 3/2001 |
| WO | WO 2001/027614 | 4/2001 |
| WO | WO 2001/028684 | 4/2001 |
| WO | WO 2001/030995 | 5/2001 |
| WO | WO 2001/041931 | 6/2001 |
| WO | WO 2001/046474 | 6/2001 |
| WO | WO 2001/054813 | 8/2001 |
| WO | WO 2001/089681 | 11/2001 |
| WO | WO 2001/089705 | 11/2001 |
| WO | WO 2001/092569 | 12/2001 |
| WO | WO 2002/043864 | 6/2002 |
| WO | WO 2002/048164 | 6/2002 |
| WO | WO 2002/052002 | 7/2002 |
| WO | WO 2002/072264 | 9/2002 |
| WO | WO 2002/078845 | 10/2002 |
| WO | WO 2002/086454 | 10/2002 |
| WO | WO 2002/094185 | 11/2002 |
| WO | WO 2003/007677 | 1/2003 |
| WO | WO 2003/012325 | 2/2003 |
| WO | WO 2003/012406 | 2/2003 |
| WO | WO 2003/048295 | 6/2003 |
| WO | WO 2003/055605 | 7/2003 |

(56) References Cited

FOREIGN PATENT DOCUMENTS

| | | |
|---|---|---|
| WO | WO 2003/076661 | 9/2003 |
| WO | WO 2003/078065 | 9/2003 |
| WO | WO 2003/080868 | 10/2003 |
| WO | WO 2003/087410 | 10/2003 |
| WO | WO 2004/007081 | 1/2004 |
| WO | WO 2004/010760 | 2/2004 |
| WO | WO 2004/048545 | 6/2004 |
| WO | WO 2004/055522 | 7/2004 |
| WO | WO 2004/056485 | 7/2004 |
| WO | WO 2004/074848 | 9/2004 |
| WO | WO 2004/094986 | 11/2004 |
| WO | WO 2005/008255 | 1/2005 |
| WO | WO 2005/011867 | 2/2005 |
| WO | WO 2005/030984 | 4/2005 |
| WO | WO 2005/072353 | 8/2005 |
| WO | WO 2005/094981 | 10/2005 |
| WO | WO 2005/107947 | 11/2005 |
| WO | WO 2005/108571 | 11/2005 |
| WO | WO 2005/108620 | 11/2005 |
| WO | WO 2005/116202 | 12/2005 |
| WO | WO 2005/118867 | 12/2005 |
| WO | WO 2005/120710 | 12/2005 |
| WO | WO 2006/010584 | 2/2006 |
| WO | WO 2006/032044 | 3/2006 |
| WO | WO 2006/035800 | 4/2006 |
| WO | WO 2006/043642 | 4/2006 |
| WO | WO 2006/066001 | 6/2006 |
| WO | WO 2006/079082 | 7/2006 |
| WO | WO 2006/081995 | 8/2006 |
| WO | WO 2006/113198 | 10/2006 |
| WO | WO 2006/118420 | 11/2006 |
| WO | WO 2006/119280 | 11/2006 |
| WO | WO 2007/044917 | 4/2007 |
| WO | WO 2007/050327 | 5/2007 |
| WO | WO 2007/064117 | 6/2007 |
| WO | WO 2007/075919 | 7/2007 |
| WO | WO 2007/091530 | 8/2007 |
| WO | WO 2007/112114 | 10/2007 |
| WO | WO 2007/120240 | 10/2007 |
| WO | WO 2007/120241 | 10/2007 |
| WO | WO 2008/005321 | 1/2008 |
| WO | WO 2008/030914 | 3/2008 |
| WO | WO 2008/060604 | 5/2008 |
| WO | WO 2008/134470 | 11/2008 |
| WO | WO 2008/149282 | 12/2008 |
| WO | WO 2009/012185 | 1/2009 |
| WO | WO 2009/054870 | 4/2009 |
| WO | WO 2010/118541 | 10/2010 |
| WO | WO 2010/130310 | 11/2010 |
| WO | WO 2010/140680 | 12/2010 |
| WO | WO 2011/009073 | 1/2011 |
| WO | WO 2011/101467 | 8/2011 |

OTHER PUBLICATIONS

Oh et al, World-to-chip microfluidic interface with built-in valves for multichamber chip-based PCR assays, 2005, Lab Chip, 845-850 (Year: 2005).*

Benters et al., "Dendrimer-Activated Solid Supports for Nucleic Acid and Protein Microarrays", ChemBioChem (2001) 2(9): 686-694.

Devarakonda et al., "The effect of PAMAM dendrimer generation size and surface functional group on the aqueous solubility of nifedipine", Int J Pharma. 284(1-2): 133-140.

Brief for Appellee HandyLab, Inc. in Appeals from the USPTO, PTAB, in Nos. IPR2019-00488, IPR2019-00490, IPR2019-01493 and IPR2019-01494 filed May 24, 2021 in U.S. Court of Appeals for the Federal Circuit Case Nos. 20-2249, 20-2250, 20-2273 and 20-2276 (74 pages).

Reply Brief of Appellants Qiagen North American Holdings, Inc. and NeuMoDx Molecular, Inc. in Appeals from the USPTO, PTAB, in Nos. IPR2019-00488, IPR2019-00490, IPR2019-01493 and IPR2019-01494 filed Jun. 21, 2021 in U.S. Court of Appeals for the Federal Circuit Case Nos. 20-2249, 20-2250, 20-2273 and 20-2276 (44 pages).

Decision Denying Institution of Inter Partes Review of U.S. Pat. No. 10,625,262 (Paper 7 in IPR2021-00250) dated Jul. 15, 2021 (15 pages).

Decision Denying Institution of Inter Partes Review of U.S. Pat. No. 10,632,466 (Paper 7 in IPR2021-00253) dated Jul. 15, 2021 (22 pages).

Decision Denying Institution of Inter Partes Review of U.S. Pat. No. 10,625,261 (Paper 7 in IPR2021-00251) dated Jul. 15, 2021 (24 pages).

Patent Owner's Response in Inter Partes Review of U.S. Pat. No. 8,709,787 and Exhibit List (Paper 29 in IPR 2020-01132) dated Jul. 15, 2021 (87 pages).

Decision Granting Institution of Inter Partes Review of U.S. Pat. No. 8,415,103 on Rehearing (Paper 23 in IPR2020-01133) dated Aug. 6, 2021 (20 pages).

Decision of U.S. Court of Appeal for the Federal Circuit Affirming Inter Partes Review Final Written Decisions Determining No Challenged Claims of U.S. Pat. Nos. 7,998,708 and 8,323,900 are Unpatentable (IPR2019-00488, IPR2019-00490, IPR2019-01493, and IPR2019-01494) dated Oct. 29, 2021 (12 pages).

Joint Motion to Terminate Inter Partes Review of U.S. Pat. No. 8,709,787 (Paper 37 in IPR 2020-01132) dated Nov. 15, 2021 (8 pages).

Joint Motion to Terminate Inter Partes Review of U.S. Pat. No. 8,415,103 (Paper 35 in IPR 2020-01133) dated Nov. 15, 2021 (8 pages).

Stipulation of Dismissal filed by Plaintiffs Becton, Dickinson and Company, Geneohm Sciences Canada, Inc. and HandyLab, Inc. and Defendants NeuMoDx Molecular, Inc., Qiagen GmbH, and Qiagen North American Holdings, Inc. on Nov. 12, 2021 in U.S. District Court, Delaware, Case # 1:19-cv-01226-LPS (3 pages).

Auroux et al., "Miniaturised nucleic acid analysis", Lab Chip. (2004) 4(6):534-546.

Baechi et al., "High-density microvalve arrays for sample processing in PCR chips", Biomed Microdevices. (2001) 3(3):183-190.

Baker M., "Clever PCR: more genotyping, smaller volumes." Nature Methods (May 2010) 70(5):351-356.

Becker H. "Fabrication of Polymer Microfluidic Devices", in Biochip Technology (2001), Chapter 4, pp. 63-96.

Becker H., "Microfluidic Devices Fabricated by Polymer Hot Embossing," in Integrated Microfabricated Biodevices: Advanced Technologies for Genomics, Drug Discovery, Bioanalysis, and Clinical Diagnostics (2002), Chapter 13, 32 pages.

Belgrader et al., "Rapid PCR for Identity Testing Using a Battery-Powered Miniature Thermal Cycler", J Forensic Sci. (1998) 43(2):315-319.

Belgrader et al., "A minisonicator to rapidly disrupt bacterial spores for DNA analysis.", Anal Chem. (1999) 71(19):4232-4236.

Belgrader et al., "Real-time PCR Analysis on Nucleic Acids Purified from Plasma Using a Silicon Chip", Micro Total Analysis Systems 2000 (pp. 525-528). Springer, Dordrecht.

Belgrader et al., "A microfluidic cartridge to prepare spores for PCR analysis", Biosens Bioelectron. (2000) 14(10-11):849-852.

Belgrader et al., "A Battery-Powered Notebook Thermal Cycler for Rapid Multiplex Real-Time PCR Analysis", Anal Chem. (2001) 73(2):286-289.

Belgrader et al., "Rapid and Automated Cartridge-based Extraction of Leukocytes from Whole Blood for Microsatellite DNA Analysis by Capillary Electrophoresis", Clin Chem. (2001) 47(10):1917-1933.

Belgrader et al., "A Rapid, Flow-through, DNA Extraction Module for Integration into Microfluidic Systems", Micro Total Analysis Systems (2002) pp. 697-699). Springer, Dordrecht.

Belgrader et al., "Development of a Battery-Powered Portable Instrumentation for Rapid PCR Analysis", in Integrated Microfabricated Devices, (2002) Ch. 8, pp. 183-206, CRC Press.

Bell M., "Integrated Microsystems in Clinical Chemistry", in Integrated Microfabricated Devices, (2002) Ch. 16, pp. 415-435, CRC Press.

(56) References Cited

OTHER PUBLICATIONS

Biomerieux Press Release: "bioMérieux—2018 Financial Results," dated Feb. 27, 2019, accessed at www.biomerieux.com, pp. 13.
Bollet, C. et al., "A simple method for the isolation of chromosomal DNA from Gram positive or acid-fast bacteria", Nucleic Acids Research, vol. 19, No. 8 (1991), p. 1955.
Brahmasandra et al., On-chip DNA detection in microfabricated separation systems, SPIE Conference on Microfluidic Devices and Systems, 1998, vol. 3515, pp. 242-251, Santa Clara, CA.
Brahmasandra et al., "Microfabricated Devices for Integrated DNA Analysis", in Biochip Technology by Cheng et al., [Eds.] (2001) pp. 229-250.
Breadmore, M.C. et al., "Microchip-Based Purification of DNA from Biological Samples", Anal. Chem., vol. 75 (2003), pp. 1880-1886.
Brody, et al., Diffusion-Based Extraction in a Microfabricated Device, Sensors and Actuators Elsevier, 1997, vol. A58, No. 1, pp. 13-18.
Broyles et al., "Sample Filtration, Concentration, and Separation Integrated on Microfluidic Devices" Analytical Chemistry (American Chemical Society), (2003) 75(11): 2761-2767.
Bu et al., "Design and theoretical evaluation of a novel microfluidic device to be used for PCR", J Micromech Microengin. (2003) 13(4):S125-S130.
Burns et al., "An Integrated Nanoliter DNA Analysis Device", Science 282:484-487 (1998).
Cady et al., "Real-time PCR detection of Listeria monocytogenes using an integrated microfluidics platform", Sensors Actuat B. (2005) 107:332-341.
Carlen et al., "Paraffin Actuated Surface Micromachined Valve," in IEEE MEMS 2000 Conference, Miyazaki, Japan, (Jan. 2000) pp. 381-385.
Cheng et al., "Biochip-Based Portable Laboratory", Biochip Tech. (2001):269-289.
Chong et al., "Disposable Polydimethylsiloxane Package for 'Bio-Microfluidic System'", IEEE Proceedings Electronic Components and Technology (2005); 5 pages.
Chou et al., "A miniaturized cyclic PCR device—modeling and experiments", Microelec Eng. (2002) 61-62:921-925.
Christel et al., "Nucleic Acid Concentration and PCR for Diagnostic Applications", in Micro Total Analysis Systems. (1998) D.J. Harrison et al. [Eds.] pp. 277-280.
Christel et al., "Rapid, Automated Nucleic Acid Probe Assays Using Silicon Microstructures for Nucleic Acid Concentration", J Biomech Eng. (1999) 121(1):22-27.
Chung, Y. et al., "Microfluidic chip for high efficiency DNA extraction", Miniaturisation for Chemistry, Biology & Bioengineering, vol. 4, No. 2 (Apr. 2004), pp. 141-147.
Cooley et al., "Applications of Ink-Jet Printing Technology to BioMEMS and Microfluidic Systems", Proceedings, SPIE Conference on Microfluids and BioMEMS, (Oct. 2001), 12 pages.
Danaher Press Release: "Danaher to Acquire Cepheid for $53.00 per share, or approximately $4 Billion," dated Sep. 6, 2016, accessed at www.danaher.com, pp. 3.
Edwards, "Silicon (Si)," in "Handbook of Optical Constants of Solids" (Ghosh & Palik eds., 1997) in 24 pages.
Edwards et al., "Micro Scale Purification Systems for Biological Sample Preparation", Biomed Microdevices (2001) 3(3):211-218.
Edwards et al., "A microfabricated thermal field-flow fractionation system", Anal Chem. (2002) 74(6):1211-1216.
El-Ali et al., "Simulation and experimental validation of a SU-8 based PCR thermocycler chip with integrated heaters and temperature sensor", Sens Actuators A: Physical (2004) 110(1-3):3-10.
Erickson et al., "Integrated Microfluidic Devices", Analytica Chim Acta. (2004) 507:11-26.
Erill et al., "Development of a CMOS-compatible PCR chip: comparison of design and system strategies", J Micromech Microengin. (2004) 14(11):1-11.
Fiorini et al., "Disposable microfluidic devices: fabrication, function, and application", Biotechniques (2005) 38(3):429-446.

Giordano et al., "Toward an Integrated Electrophoretic Microdevice for Clinical Diagnostics", in Integrated Microfabricated Biodevices: Advanced Technologies for Genomics, Drug Discovery, Bioanalysis, and Clinical Diagnostics (2002) Chapter 1; pp. 1-34.
Goldmeyer et al., "Identification of *Staphylococcus aureus* and Determination of Methicillin Resistance Directly from Positive Blood Cultures by Isothermal Amplification and a Disposable Detection Device", J Clin Microbiol. (Apr. 2008) 46(4): 1534-1536.
Grunenwald H., "Optimization of Polymerase Chain Reactions," in Methods in Molecular Biology, PCR Protocols., Second Edition by Bartlett et al. [Eds.] Humana Press (2003) vol. 226, pp. 89-99.
Hale et al., "Optical constants of Water in the 200-nm to 200-μm Wavelength Region", Applied Optics, 12(3): 555-563 (1973).
Handique et al., "Microfluidic flow control using selective hydrophobic patterning", SPIE, (1997) 3224:185-194.
Handique et al., "On-Chip Thermopneumatic Pressure for Discrete Drop Pumping", Anal. Chem., (2001) 73(8):1831-1838.
Handique et al., "Nanoliter-volume discrete drop injection and pumping in microfabricated chemical analysis systems", Solid-State Sensor and Actuator Workshop (Hilton Head, South Carolina, Jun. 8-11, 1998) pp. 346-349.
Handique et al., "Mathematical Modeling of Drop Mixing in a Slit-Type Microchannel", J. Micromech. Microeng., 11:548-554 (2001).
Handique et al., "Nanoliter Liquid Metering in Microchannels Using Hydrophobic Patterns", Anal. Chem., 72(17):4100-4109 (2000).
Harding et al., "DNA isolation using Methidium-Spermine-Sepharose", Meth Enzymol. (1992) 216:29-39.
Harding et al., "Rapid isolation of DNA from complex biological samples using a novel capture reagent—methidium-spermine-sepharose", Nucl Acids Res. (1989) 17(17): 6947-6958.
He et al., Microfabricated Filters for Microfluidic Analytical Systems, Analytical Chemistry, American Chemical Society, 1999, vol. 71, No. 7, pp. 1464-1468.
Henry C.S. [Ed], "Microchip Capillary electrophoresis", Methods in Molecular Biology, Humana Press 339 (2006) Parts I-IV in 250 pages.
Hong et al., "Integrated nanoliter systems", Nat Biotechnol. (2003) 21(10):1179-1183.
Ibrahim, et al., Real-Time Microchip PCR for Detecting Single-Base Differences in Viral and Human DNA, Analytical Chemistry, American Chemical Society, 1998, 70(9): 2013-2017.
International Search Report and Written Opinion dated Jan. 31, 2006 for PCT/US2005/015345, filed May 3, 2005.
Kelly et al., "Microfluidic Systems for Integrated, High-Throughput DNA Analysis," Analytical Chemistry, (2005), 97A-102A, Mar. 1, 2005, in 7 pages.
Khandurina et al., Microfabricated Porous Membrane Structure for Sample Concentration and Electrophoretic Analysis, Analytical Chemistry American Chemical Society, 1999, 71(9): 1815-1819.
Khandurina et al., "Bioanalysis in microfluidic devices," J Chromatography A, (2002) 943:159-183.
Kim et al., "Electrohydrodynamic Generation and Delivery of Monodisperse Picoliter Droplets Using a Poly(dimethylsiloxane) Microchip", Anal Chem. (2006) 78: 8011-8019.
Kopf-Sill et al., "Creating a Lab-on-a-Chip with Microfluidic Technologies", in Integrated Microfabricated Biodevices: Advanced Technologies for Genomics, Drug Discovery, Bioanalysis, and Clinical Diagnostics (2002) Chapter 2; pp. 35-54.
Kopp et al., Chemical Amplification: Continuous-Flow PCR on a Chip, www.sciencemag.org, 1998, vol. 280, pp. 1046-1048.
Kuo et al., "Remnant cationic dendrimers block RNA migration in electrophoresis after monophasic lysis", J Biotech. (2007) 129: 383-390.
Kutter et al., Solid Phase Extraction on Microfluidic Devices, J. Microcolumn Separations, John Wiley & Sons, Inc., 2000, 12(2): 93-97.
LABCHEM; Sodium Hydroxide, 0,5N (0.5M); Safety Data Sheet, 2015; 8 pages.
Lagally et al., Single-Molecule DNA Amplification and Analysis in an Integrated Microfluidic Device, Analytical Chemistry, American Chemical Society, 2001, 73(3): 565-570.

(56) References Cited

OTHER PUBLICATIONS

Lagally et al., "Genetic Analysis Using Portable PCR-CE Microsystem", Proceedings 7th International Conference on Miniaturized Chemical and Biochemical Analysis Systems (2003) pp. 1283-1286.
Lagally et al., "Integrated portable genetic analysis microsystem for pathogen/infectious disease detection", Anal Chem. (2004) 76(11):3152-3170.
Lawyer et al., "High-level Expression, Purification, and Enzymatic Characterization of Full-length Thermus aquaticus DNA Polymerase and a Truncated Form Deficient in 5'to 3'Exonuclease Activity." Genome research (1993) 2(4):275-287.
Li Pch., "Applications to Nucleic Acids Analysis" in Microfluidic Lab-on-a-Chip for Chemical and Biological Analysis and Discovery, CRC Press (2005), Chapter 9; pp. 293-325.
Livache et al., "Polypyrrole DNA chip on a Silicon Device: Example of Hepatitis C Virus Genotyping", Analytical Biochemistry, (1998) 255: 188-194.
Malitson, "Interspecimen Comparison of the Refractive Index of Fused Silica," J Optical Society of America, 55:1205-1209 (1965).
Mariella R.P. Jr., "Microtechnology", Thrust Area Report FY 96 UCRL-ID-125472; Lawrence Livermore National Lab., CA (Feb. 1997) Chapter 3 in 44 pages.
Mastrangelo et al., Microfabricated Devices for Genetic Diagnostics. Proceedings of the IEEE (1998) 86(8):1769-1787.
Mascini et al., "DNA electrochemical biosensors", Fresenius J. Anal. Chem., 369: 15-22, (2001).
McMillan et al., "Application of advanced microfluidics and rapid PCR to analysis of microbial targets", In Proceedings of the 8th international symposium on microbial ecology (1999), in 13 pages.
Meyers, R.A., Molecular Biology and Biotechnology: A Comprehensive Desk Reference; VCH Publishers, Inc. New York, NY; (1995) pp. 418-419.
Nakagawa et al., Fabrication of amino silane-coated microchip for DNA extraction from whole blood, J of Biotechnology, Mar. 2, 2005, 116: 105-111.
Northrup et al., A Miniature Analytical Instrument for Nucleic Acids Based on Micromachined Silicon Reaction Chambers, Analytical Chemistry, American Chemical Society, 1998, 70(5): 918-922.
Northrup et al., "A New Generation of PCR Instruments and Nucleic Acid Concentration Systems," in PCR Applications: Protocols for Functional Genomics, (1999), Chapter 8, pp. 105-125.
Northrup, "Microfluidics, A few good tricks," Nature materials (2004), 3:282-283.
Oh K.W. et al., "A Review of Microvalves", J Micromech Microeng. (2006) 16:R13-R39.
Oleschuk et al., Trapping of Bead-Based Reagents within Microfluidic Systems: On-Chip Solid-Phase Extraction and Electrochromatography, Analytical Chemistry, American Chemical Society, 2000, 72(3): 585-590.
Pal et al., "Phase Change Microvalve for Integrated Devices", Anal Chem. (2004) 76: 3740-3748.
Pal et al., "An integrated microfluidic for influenza and other genetic analyses," Lab Chip, (2005), 5:1024-1032.
Palina et al., "Laser Assisted Boron Doping of Silicon Wafer Solar Cells Using Nanosecond and Picosecond Laser Pulses," 2011 37th IEEE Photovoltaic Specialists Conference, pp. 002193-002197, IEEE (2011).
Paulson et al., "Optical dispersion control in surfactant-free DNA thin films by vitamin B2 doping," Nature, Scientific Reports 8:9358 (2018) published at www.nature.com/scientificreports, Jun. 19, 2018.
Petersen, Kurt E., "Silicon as a Mechanical Material." Proceedings of the IEEE, (May 1982) 70(5):420-457.
Picard et al., Laboratory Detection of Group B *Streptococcus* for Prevention of Perinatal Disease, Eur. J. Clin. Microbiol. Infect. Dis., Jul. 16, 2004, 23: 665-671.
Plambeck et al., "Electrochemical Studies of Antitumor Antibiotics", J. Electrochem Soc.: Electrochemical Science and Technology (1984), 131(11):2556-2563.
Pourahmadi et al., "Toward a Rapid, Integrated, and Fully Automated DNA Diagnostic Assay for Chlamydia trachomatis and Neisseria gonorrhea," Clinical Chemistry, (2000), 46(9):1511-1513.
Pourahmadi et al., "Versatile, Adaptable and Programmable Microfluidic Platforms for DNA Diagnostics and Drug Discovery Assays," Micro Total Analysis Systems, (2000), 243-248.
Raja et al., "Technology for Automated, Rapid, and Quantitative PCR or Reverse Transcription-PCR Clinical Testing," Clinical Chemistry, (2005), 51(5):882-890.
Roche et al. "Ectodermal commitment of insulin-producing cells derived from mouse embryonic stem cells" Faseb J (2005) 19: 1341-1343.
Ross et al., Analysis of DNA Fragments from Conventional and Microfabricated PCR Devices Using Delayed Extraction MALDI-TOF Mass Spectrometry, Analytical Chemistry, American Chemical Society, 1998, 70(10): 2067-2073.
Sanchez et al., "Linear-After-The-Exponential (LATE)-PCR: An advanced method of asymmetric PCR and its uses in quantitative real-time analysis", PNAS (2004) 101(7): 1933-1938.
Shoffner et al., Chip PCR.I. Surface Passivation of Microfabricated Silicon-Glass Chips for PCR, Nucleic Acids Research, Oxford University Press, (1996) 24(2): 375-379.
Smith, K. et al., "Comparison of Commercial DNA Extraction Kits for Extraction of Bacterial Genomic DNA from Whole-Blood Samples", Journal of Clinical Microbiology, vol. 41, No. 6 (Jun. 2003), pp. 2440-2443.
Supplementary European Search dated Jan. 10, 2008 for European Patent Application No. 05745564, filed May 3, 2005.
Tanaka et al., "Improved Method of DNA Extraction from Seeds Using Amine-Dendrimer Modified Magnetic Particles", Proceedings of the 74th Annual Meeting of the Electrochemical Society of Japan; Abstract #2E09 on p. 149, Mar. 29, 2007; Faculty of Engineering, Science University of Tokyo; 4 pages.
Taylor et al., Fully Automated Sample Preparation for Pathogen Detection Performed in a Microfluidic Cassette, in Micro Total Analysis Systems, Springer (2001), pp. 670-672.
Taylor et al., "Lysing Bacterial Spores by Sonication through a Flexible Interface in a Microfluidic System," Anal. Chem., (2001), 73(3):492-496.
Taylor et al., "Microfluidic Bioanalysis Cartridge with Interchangeable Microchannel Separation Components," (2001), The 11th International Conference on Solid-State Sensors and Actuators, Jun. 10-14, 2001, Munich, Germany; 1214-1247.
Taylor et al., "Disrupting Bacterial Spores and Cells using Ultrasound Applied through a Solid Interface," (2002), 2nd Annual International IEEE-EMBS Special Topic Conference on Microtechnologies in Medicine & Biology, May 2-4, 2002, Madison, Wisconsin; 551-555.
Thorsen et al., "Microfluidic Large-scale integration," Science, (2002), 298:580-584.
Vinet et al., "Microarrays and microfluidic devices: miniaturized systems for biological analysis," Microelectronic Engineering, (2002), 61-62:41-47.
Wang, "Survey and Summary, from DNA Biosensors to Gene Chips", Nucleic Acids Research, 28(16):3011-3016, (2000).
Wang et al., "From biochips to laboratory-on-a-chip system", in Genomic Signal Processing and Statistics by Dougherty et al. [Eds]; (2005) Chapter 5, pp. 163-200.
Waters et al., Microchip Device for Cell Lysis, Multiplex PCR Amplification, and Electrophoretic Sizing, Analytical Chemistry, American Chemical Society, 1998, 70(1): 158-162.
Weigl, et al., Microfluidic Diffusion-Based Separation and Detection, www.sciencemag.org, 1999, vol. 283, pp. 346-347.
Wu et al., "Polycationic dendrimers interact with RNA molecules: polyamine dendrimers inhibit the catalytic activity of Candida ribozymes", Chem Common. (2005) 3: 313-315.
Yang et al., "High sensitivity PCR assay in plastic micro reactors," Lab Chip, (2002), 2:179-187.
Yobas et al., Microfluidic Chips for Viral RNA Extraction & Detection, (2005), 2005 IEEE, 49-52.
Yoza et al., "Fully Automated DNA Extraction from Blood Using Magnetic Particles Modified with a Hyperbranched Polyamidoamine Dendrimer", J Biosci Bioeng, 2003, 95(1): 21-26.

(56) References Cited

OTHER PUBLICATIONS

Yoza et al., DNA extraction using bacterial magnetic particles modified with hyperbranched polyamidoamine dendrimer, J Biotechnol., Mar. 20, 2003, 101(3): 219-228.
Zhang et al., "PCR Microfluidic Devices for DNA Amplification," Biotechnology Advances, 24:243-284 (2006).
Zhou et al., "Cooperative binding and self-assembling behavior of cationic low molecular-weight dendrons with RNA molecules", Org Biomol Chem. (2006) 4(3): 581-585.
Zhou et al., "PAMAM dendrimers for efficient siRNA delivery and potent gene silencing", Chem Comm.(Camb.) (2006) 22: 2362-2364.
Zou et al., "A Micromachined Integratable Thermal Reactor," technical digest from International Electron Devices Meeting, IEEE, Washington, D.C., Dec. 2-5, 2001 (6 pages).
Petition for Inter Partes Review of U.S. Pat. No. 7,998,708 (Paper 1 in IPR2019-00488) dated Dec. 20, 2018 (94 pages).
Declaration of Bruce K. Gale, Ph.D. (Exhibit 1001 in IPR2019-00488 and IPR2019-00490) dated Dec. 20, 2018 (235 pages).
Patent Owner Preliminary Response to Petition for Inter Partes Review of U.S. Pat. No. 7,998,708 and Exhibit List (Papers 5 and 6 in IPR2019-00488) dated Apr. 18, 2019 (79 pages).
Decision instituting Inter Partes Review of U.S. Pat. No. 7,998,708 (Paper 8 in IPR2019-00488) dated Jul. 16, 2019 (20 pages).
Petition for Inter Partes Review of U.S. Pat. No. 8,323,900 (Paper 1 in IPR2019-00490) dated Dec. 20, 2018 (85 pages).
Declaration of Michael G. Mauk, Ph.D. in Support of Patent Owner Preliminary Responses in IPR2019-00488 and IPR2019-00490 dated Apr. 18, 2019 (43 pages).
Patent Owner Preliminary Response to Petition for Inter Partes Review of U.S. Pat. No. 8,323,900 and Exhibit List (Papers 5 and 6 in IPR2019-00490) dated Apr. 18, 2019 (73 pages).
Decision instituting Inter Partes Review of U.S. Pat. No. 8,323,900 (Paper 8 in IPR2019-00490) dated Jul. 16, 2019 (23 pages).
Patent Owner's Response in Inter Partes Review of U.S. Pat. No. 8,323,900 and Exhibit List (Paper 25 in IPR2019-00490) dated Oct. 16, 2019 (80 pages).
Patent Owner's Response in Inter Partes Review of U.S. Pat. No. 7,998,708 and Exhibit List (Paper 25 in IPR 2019-00488) dated Oct. 16, 2019 (93 pages).
Transcript of Deposition of Bruce K. Gale, Ph.D., in Support of Patent Owner's Responses (Exhibit 2012 in IPR2019-00488 and IPR2019-00490), taken Sep. 24, 2019 (124 pages).
Declaration of M. Allen Northrup, Ph.D. in Support of Patent Owner's Responses (Exhibit 2036 in IPR2019-00488 and IPR2019-00490) dated Oct. 16, 2019 (365 pages).
Petitioner's Reply to Patent Owner's Response to Petition in Inter Partes Review of U.S. Pat. No. 7,998,708 and Exhibit List (Paper 32 in IPR 2019-00488) dated Jan. 31, 2020 (34 pages).
Petitioner's Reply to Patent Owner's Response to Petition in Inter Partes Review of U.S. Pat. No. 8,323,900 and Exhibit List (Paper 32 in IPR 2019-00490) dated Jan. 31, 2020 (35 pages).
Second Declaration of Bruce K. Gale, Ph.D. (Exhibit 1026 in IPR2019-00488 and IPR2019-00490) dated Jan. 31, 2020 (91 pages).
Transcript of Deposition of M. Allen Northrup, Ph.D., (Exhibit 1027 in IPR2019-00488 and IPR2019-00490), taken Dec. 19, 2019 (109 pages).
Complaint filed by *Becton, Dickinson et al.*, v. *NeuModx Molecular, Inc.* on Jun. 18, 2019 in U.S. District Court, Delaware, Case #1:19-cv-01126-LPS, Infringement Action involving U.S. Patent Nos. 7,998,708; 8,273,308; 8,323,900; 8,415,103; 8,703,069; and 8,709,787 (29 pages).
Answer to Complaint filed by NeuModx Molecular, Inc. on Aug. 9, 2019 in U.S. District Court, Delaware, Case #1:19-cv-01126-LPS (24 pages).
Amended Answer to Complaint filed by NeuModx Molecular, Inc. on Oct. 4, 2019 in U.S. District Court, Delaware, Case #1:19-cv-01126-LPS (31 pages).

Anderson et al., "Microfluidic biochemical analysis system" Proc. 1997 IEEE Int. Conf. Solid-State Sens. Actuat. (1997) pp. 477-480.
Anderson et al., "Advances in Integrated Genetic Analysis" Micro Total Analysis Systems '98 Conference Proceedings, D. Kluwer Academic Publishers (1998) in 6 pages.
Anderson et al., "A Miniature Integrated Device for Automated Multistep Genetic Assays" Nucleic Acids Research (2000) 28(12), i-vi.
Harrison et al., "Capillary Electrophoresis and Sample Injection Systems Integrated on a Planar Glass Chip", Anal. Chem., (1992) 64: 1926-1932.
Hsueh et al., "A microfabricated, electrochemiluminescence cell for the detection of amplified DNA" Proc. 1995 IEEE Int. Conf. Solid-State Sens. Actuators (1995) pp. 768-771.
Hsueh et al., "DNA quantification with an electrochemiluminescence microcell" Proc. 1997 IEEE Int. Conf. Solid-State Sens. Actuators (1997) pp. 175-178.
Jiang et al., "Directing cell migration with asymmetric micropatterns" Proc. Natl. Acad. Sci. USA (2005) 102, 975-978.
Lagally et al., "Monolithic integrated microfluidic DNA amplification and capillary electrophoresis analysis system" Sensors and Actuators B (2000) 63:138-146.
Manz et al., "Design of an open-tubular column liquid chromatograph using silicon chip technology" Sensors and Actuators B (1990) 1:249-255.
Manz et al., "Planar chips technology for miniaturization and integration of separation techniques into monitoring systems: Capillary electrophoresis on a chip" Journal of Chromatography A (1992) 593:253-258.
Northrup et al., "A MEMS-based Miniature DNA Analysis System." Transducers '95—Eurosensors in Proc. 1995 (8th) IEEE Int. Conf. Solid-State Sens. Actuators, pp. 764-767.
Rhee et al., "Drop Mixing in a Microchannel for Lab-on-a-Chip Applications" Langmuir (2008) 24 (2): 590-601.
Sammarco et al., "Thermocapillary Pumping of Discrete Drops in Microfabricated Analysis Devices" AIChE Journal (1999) 45(2): 350-366.
U.S. Appl. No. 60/491,264, filed Jul. 31, 2003 (41 pages).
U.S. Appl. No. 60/491,269, filed Jul. 31, 2003 (52 pages).
U.S. Appl. No. 60/491,539, filed Aug. 1, 2003 (45 pages).
U.S. Appl. No. 60/553,553, filed Mar. 17, 2004 (49 pages).
U.S. Appl. No. 60/726,066, filed Oct. 11, 2005 (54 pages).
U.S. Appl. No. 60/786,007, filed Mar. 24, 2006 (223 pages).
U.S. Appl. No. 60/859,284, filed Nov. 14, 2006 (114 pages).
Zhang et al., "Parallel DNA amplification by convective polymerase chain reaction with various annealing temperatures on a thermal gradient device," Analytical Biochemistry, (2009) 387:102-112.
Patent Owner's Sur-Reply in Inter Partes Review of U.S. Pat. No. 8,323,900 (Paper 42 in IPR2019-00490) dated Mar. 12, 2020 (39 pages).
Patent Owner's Sur-Reply in Inter Partes Review of U.S. Pat. No. 7,998,708 (Paper 43 in IPR 2019-00488) dated Mar. 12, 2020 (41 pages).
Transcript of Second Deposition of Bruce K. Gale, Ph.D., (Exhibit 2068 in IPR2019-00488 and IPR2019-00490), taken Feb. 19, 2020 (352 pages).
Record of Oral Hearing in IPR2019-00488 and IPR2019-00490 held Apr. 21, 2020 in 80 pages; Petitioner's Demonstratives for Oral Hearing in IPR2019-00488 and IPR2019-00490 held Apr. 21, 2020 in 72 pages; Patent Owner's Demonstratives for Oral Hearing in IPR2019-00488 and IPR2019-00490 held Apr. 21, 2020 in 88 pages; Patent Owner's Objections to Petitioner's Oral Hearing Demonstratives in IPR2019-00488 and IPR2019-00490 dated Apr. 16, 2020 (4 pages).
Judgment/Final Written Decision Determining No Challenged Claims Unpatentable in Inter Partes Review of U.S. Pat. No. 7,998,708 (Paper No. 52 in IPR2019-00488) dated Jul. 14, 2020 (43 pages).
Judgment/Final Written Decision Determining No Challenged Claims Unpatentable in Inter Partes Review of U.S. Pat. No. 8,323,900 (Paper No. 51 in IPR2019-00490) dated Jul. 14, 2020 (43 pages).
Petitioner's Notice of Appeal in Inter Partes Review of U.S. Pat. No. 7,998,708 (Paper No. 54 in IPR2019-00488) dated Sep. 9, 2020 (48 pages).

(56) References Cited

OTHER PUBLICATIONS

Petitioner's Notice of Appeal in Inter Partes Review of U.S. Pat. No. 8,323,900 (Paper No. 53 in IPR2019-00490) dated Sep. 9, 2020 (48 pages).
Petition for Inter Partes Review of U.S. Pat. No. 8,273,308 (Paper 2 in IPR2020-01083) dated Jun. 12, 2020 (104 pages).
Petition for Inter Partes Review of U.S. Pat. No. 8,273,308 (Paper 2 in IPR2020-01091) dated Jun. 12, 2020 (105 pages).
Petition for Inter Partes Review of U.S. Pat. No. 8,803,069 (Paper 2 in IPR2020-01095) dated Jun. 12, 2020 (84 pages).
Petition for Inter Partes Review of U.S. Pat. No. 8,803,069 (Paper 3 in IPR2020-01100) dated Jun. 12, 2020 (83 pages).
Petition for Inter Partes Review of U.S. Pat. No. 8,709,787 (Paper 2 in IPR2020-01132) dated Jun. 18, 2020 (96 pages).
Petition for Inter Partes Review of U.S. Pat. No. 8,415,103 (Paper 2 in IPR2020-01133) dated Jun. 18, 2020 (96 pages).
Petition for Inter Partes Review of U.S. Pat. No. 8,709,787 (Paper 2 in IPR2020-01137) dated Jun. 19, 2020 (86 pages).
Petition for Inter Partes Review of U.S. Pat. No. 8,415,103 (Paper 2 in IPR2020-01136) dated Jun. 19, 2020 (85 pages).
Declaration of Mark A. Burns, Ph.D. (Exhibit N1001 in IPR2020-01083, IPR2020-01091, IPR2020-01095 and IPR2020-01100) dated Jun. 12, 2020 (378 pages).
Declaration of Mark A. Burns, Ph.D. (Exhibit N1101 in IPR2020-01132 and IPR2020-01133) dated Jun. 17, 2020 (253 pages).
Declaration of Mark A. Burns, Ph.D. (Exhibit N1201 in IPR2020-01136 and IPR2020-01137) dated Jun. 19, 2020 (205 pages).
Patent Owner's Preliminary Response to Petition for Inter Partes Review of U.S. Pat. No. 8,703,069 (Paper 13 in IPR2020 01095) dated Sep. 17, 2020 (77 pages).
Patent Owner's Preliminary Response to Petition for Inter Partes Review of U.S. Pat. No. 8,273,308 (Paper 13 in IPR2020 01091) dated Sep. 17, 2020 (70 pages).
Patent Owner's Preliminary Response to Petition for Inter Partes Review of U.S. Pat. No. 8,703,069 (Paper 14 in IPR2020 01100) dated Sep. 17, 2020 (59 pages).
Declaration of M. Allen Northrup, Ph.D. in Support of Patent Owner Preliminary Responses in IPR2020-01091, IPR2020-01095 and IPR2020-01100 (Exhibit H2003) dated Sep. 16, 2020 (137 pages).
Patent Owner's Preliminary Response to Petition for Inter Partes Review of U.S. Pat. No. 8,273,308 (Paper 13 in IPR2020-01083) dated Oct. 22, 2020 (88 pages).
Declaration of M. Allen Northrup, Ph.D. in support of Patent Owner Preliminary Responses in IPR2020-01083, IPR2020-01091, IPR2020-01095 and IPR2020-01100 (Exhibit H2003) dated Oct. 21, 2020 (171 pages).
Petition for Inter Partes Review of U.S. Pat. No. 10,625,262 (Paper 2 in IPR2021-00250) dated Nov. 25, 2020 (107 pages).
Petition for Inter Partes Review of U.S. Pat. No. 10,625,261 (Paper 2 in IPR2021-00251) dated Nov. 25, 2020 (117 pages).
Petition for Inter Partes Review of U.S. Pat. No. 10,632,466 (Paper 2 in IPR2021-00253) dated Nov. 25, 2020 (121 pages).
Declaration of Mark A. Burns, Ph.D. (Exhibit N1001 in IPR2021-00250, IPR2021-00251 and IPR2021-00253) dated Nov. 24, 2020 (311 pages).
Declaration of James L. Mullins, Ph.D. (Exhibit N1029 in IPR2021-00250, IPR2021-00251, and IPR2021-00253) dated Nov. 18, 2020 (54 pages).
Decision Denying Institution of Inter Partes Review of U.S. Pat. No. 8,273,308 (Paper 14 in IPR2020-01091) dated Dec. 4, 2020 (21 pages).
Decision Denying Institution of Inter Partes Review of U.S. Pat. No. 8,703,069 (Paper 14 in IPR2020-01095) dated Dec. 4, 2020 (22 pages).
Decision Denying Institution of Inter Partes Review of U.S. Pat. No. 8,703,069 (Paper 15 in IPR2020-01100) dated Dec. 4, 2020 (19 pages).
First Amended and Supplemental Complaint filed by Becton, Dickinson and Company et al. on Jun. 25, 2020 in U.S. District Court, Delaware, Case #1:19-cv-01126-LPS, Infringement Action involving U.S. Pat. Nos. 7,998,708; 8,273,308; 8,323,900; 8,415,103; 8,703,069; 8,709,787; 10,494,663; 10,364,456; 10,443,088; 10,604,788; 10,625,261; 10,625,262; and 10,632,466 (55 pages).
Answer to First Amended and Supplemental Complaint filed by NeuModx Molecular, Inc. on Jul. 16, 2020 in U.S. District Court, Delaware, Case #1:19-cv-01126-LPS (42 pages).
Defendant NeuModx's Initial Invalidity Contentions filed Sep. 30, 2020 in U.S. District Court, Delaware, Case #1:19-cv-01126-LPS (47 pages).
Defendant NeuModx's Joint Claim Construction Chart [Exhibit N1023] filed Oct. 21, 2020 in U.S. District Court, Delaware, Case #1:19-cv-01126-LPS (25 pages).
Defendant NeuModx's Initial Amended Answer, Affirmative Defenses, and Counterclaims to Plaintiffs' First Amended and Supplemental Complaint filed Nov. 23, 2020 in U.S. District Court, Delaware, Case #1:19-cv-01126-LPS (97 pages).
Altet et al., [Eds.] "Thermal Transfer and Thermal Coupling in IC's", Thermal Testing of Integrated Circuits; Chapter 2 (2002) Springer Science pp. 23-51.
BDProbeTec™ ET Neisseria gonorrhoeae Amplified DNA Assay Package Insert, Jul. 2010 (13 pages).
BDProbeTec™ ET System Brochure, Aug. 2010 (9 pages).
Burns et al., "Microfabricated Structures for Integrated DNA Analysis" Proc. Natl. Acad. Sci. USA (May 1996) 93: 5556-5561.
Ehrlich et al., "Microfluidic devices for DNA analysis", Trends Biotechnol. (1999) 17(8):315-319.
Gill et al., "Nucleic Acid Isothermal Amplification Technologies—A Review", Nucleosides Nucleotides Nucleic Acids, (2008) 27(3): 224-243.
Heid et al., "Genome Methods—Real Time Quantitative PCR", Genome Res. (1996) 6(10):986-994.
Raisi et al., "Microchip isoelectric focusing using a miniature scanning detection system," Electrophoresis, (2001), 22:2291-2295.
Reyes et al., "Micro Total Analysis Systems. 1. Introduction, Theory, and Technology", Anal Chem (2002) 74:2623-2636.
Rush et al., "Dispersion by Pressure-Driven Flow in Serpentine Microfluidic Channels", Ind Eng Chem Res., (2002) 41: 4652-4662.
Walker et al., "Strand displacement amplification—an isothermal, in vitro DNA amplification technique", Nucleic Acids Res. (1992) 20(7): 1691-1696.
Decision Denying Institution of Inter Partes Review of U.S. Pat. No. 8,273,308 (Paper 14 in IPR2020-01083) dated Jan. 7, 2021 (24 pages).
Patent Owner's Preliminary Response to Petition for Inter Partes Review of U.S. Pat. No. 8,415,103 (Paper 20 in IPR2020-01133) dated Jan. 20, 2021 (67 pages).
Patent Owner's Preliminary Response to Petition for Inter Partes Review of U.S. Pat. No. 8,709,787 (Paper 19 in IPR2020-01132) dated Jan. 20, 2021 (78 pages).
Declaration of M. Allen Northrup, Ph.D. in support of Patent Owner Preliminary Responses in IPR2020-01132 and IPR2020-01133 (Exhibit H2016) dated Jan. 20, 2021 (154 pages).
Patent Owner's Preliminary Response to Petition for Inter Partes Review of U.S. Pat. No. 8,415,103 (Paper 19 in IPR2020-01136) dated Jan. 20, 2021 (77 pages).
Patent Owner's Preliminary Response to Petition for Inter Partes Review of U.S. Pat. No. 8,709,787 (Paper 19 in IPR2020-01137) dated Jan. 20, 2021 (69 pages).
Declaration of M. Allen Northrup, Ph.D. in support of Patent Owner Preliminary Responses in IPR2020-01136 and IPR2020-01137 (Exhibit H2016) dated Jan. 20, 2021 (111 pages).
Opening Brief [Corrected] of Appellants Qiagen North American Holdings, Inc. and NeuMoDx Molecular Inc. in Appeals to IPR2019-00488, IPR2019-00490, IPR2019-01493 and IPR2019-01494 filed Jan. 22, 2021 in U.S. Court of Appeals for the Federal Circuit Case Nos. 20-2249, 20-2250, 20-2273 and 20-2276 (82 pages).
Decision Granting Institution of Inter Partes Review of U.S. Pat. No. 8,709,787 (Paper 20 in IPR2020-01132) dated Apr. 19, 2021 (33 pages).
Decision Denying Institution of Inter Partes Review of U.S. Pat. No. 8,415,103 (Paper 21 in IPR2020-01133) dated Apr. 19, 2021 (24 pages).

(56) References Cited

OTHER PUBLICATIONS

Decision Denying Institution of Inter Partes Review of U.S. Pat. No. 8,415,103 (Paper 20 in IPR2020-01136) dated Apr. 19, 2021 (19 pages).

Decision Denying Institution of Inter Partes Review of U.S. Pat. No. 8,709,787 (Paper 20 in IPR2020-01137) dated Apr. 19, 2021 (14 pages).

Patent Owner's Preliminary Response to Petition for Inter Partes Review of U.S. Pat. No. 10,625,262 (Paper 6 in IPR2021-00250) dated Apr. 19, 2021 (71 pages).

Patent Owner's Preliminary Response to Petition for Inter Partes Review of U.S. Pat. No. 10,625,261 (Paper 6 in IPR2021-00251) dated Apr. 19, 2021 (82 pages).

Patent Owner's Preliminary Response to Petition for Inter Partes Review of U.S. Pat. No. 10,632,466 (Paper 6 in IPR2021-00253) dated Apr. 19, 2021 (66 pages).

Declaration of James P. Landers, Ph.D. in support of Patent Owner Preliminary Responses in IPR2021-00250, IPR2021-00251, and IPR2021-00253 (Exhibit H2003) dated Apr. 19, 2021 (189 pages).

Second Amended and Supplemental Complaint filed by Becton, Dickinson and Company et al. on Feb. 25, 2021 in U.S. District Court, Delaware, Case #1:19-cv-01126-LPS (75 pages).

Defendant NeuMoDx's First Supplemental Invalidity Contentions filed Mar. 17, 2021 in U.S. District Court, Delaware, Case #1:19-cv-01126-LPS (55 pages).

Defendant NeuModx's Answer, Affirmative Defenses, and Counterclaims to Plaintiffs' Second and Supplemental Complaint filed Mar. 18, 2021 in U.S. District Court, Delaware, Case #1:19-cv-01126-LPS (67 pages).

Plaintiffs' Answer and/or Reply to Defendants' Counterclaims and Counterclaims-In-Reply filed Apr. 22, 2021 in U.S. District Court, Delaware, Case #1:19-cv-01126-LPS (127 pages).

Claim Construction (Markman) Order dated May 10, 2021 in in U.S. District Court, Delaware, Case #1:19-cv-01126-LPS (30 pages).

* cited by examiner

METHOD FOR PROCESSING POLYNUCLEOTIDE-CONTAINING SAMPLES

CROSS-REFERENCE TO RELATED APPLICATIONS

This application is a continuation of U.S. patent application Ser. No. 16/556,067, filed Aug. 29, 2019, which is a continuation of U.S. patent application Ser. No. 16/518,735, filed Jul. 22, 2019 and issued as U.S. Pat. No. 10,443,088 on Oct. 15, 2019, which is a continuation of U.S. patent application Ser. No. 14/506,471, filed Oct. 3, 2014 and issued as U.S. Pat. No. 10,364,456 on Jul. 30, 2019, which is a continuation of U.S. patent application Ser. No. 11/281,247, filed Nov. 16, 2005 and issued as U.S. Pat. No. 8,852,862 on Oct. 7, 2014, which is a continuation-in-part of International Application No. PCT/US2005/015345, filed May 3, 2005, which claims the benefit of priority of U.S. Provisional Application No. 60/567,174, filed May 3, 2004, and U.S. Provisional Application No. 60/645,784, filed Jan. 21, 2005. Each of these applications is incorporated herein by reference in its entirety.

FIELD OF THE INVENTION

The present invention relates to methods for processing polynucleotide-containing samples as well as to related systems.

BACKGROUND

The analysis of a biological sample often includes detecting one or more polynucleotides present in the sample. One example of detection is qualitative detection, which relates, for example, to the determination of the presence of the polynucleotide and/or the determination of information related to, for example, the type, size, presence or absence of mutations, and/or the sequence of the polynucleotide. Another example of detection is quantitative detection, which relates, for example, to the determination of the amount of polynucleotide present. Detection may include both qualitative and quantitative aspects.

Detecting polynucleotides often involves the use of an enzyme. For example, some detection methods include polynucleotide amplification by polymerase chain reaction (PCR) or a related amplification technique. Other detection methods that do not amplify the polynucleotide to be detected also make use of enzymes. However, the functioning of enzymes used in such techniques may be inhibited by the presence of inhibitors present along with the polynucleotide to be detected. The inhibitors may interfere with, for example, the efficiency and/or specificity of the enzymes.

SUMMARY OF THE INVENTION

One aspect of the present invention relates to a method and related systems for processing one or more polynucleotides (e.g., to concentrate the polynucleotide(s) and/or to separate the polynucleotide(s) from inhibitor compounds (e.g., hemoglobin, peptides, faecal compounds, humic acids, mucosal compounds, DNA binding proteins, or a saccharide) that might inhibit detection and/or amplification of the polynucleotides).

In some embodiments, the method includes contacting the polynucleotides and a relatively immobilized compound that preferentially associates with (e.g., retains) the polynucleotides as opposed to inhibitors. An exemplary compound is a poly-cationic polyamide (e.g., poly-L-lysine and/or poly-D-lysine), or polyethyleneimine (PEI), which may be bound to a surface (e.g., a surface of one or more particles). The compound retains the polynucleotides so that the polynucleotides and inhibitors may be separated, such as by washing the surface with the compound and associated polynucleotides. Upon separation, the association between the polynucleotide and compound may be disrupted to release (e.g., separate) the polynucleotides from the compound and surface.

In some embodiments, the surface (e.g., a surface of one or more particles) is modified with a poly-cationic substance such as a polyamide or PEI, which may be covalently bound to the surface. The poly-cationic polyamide may include at least one of poly-L-lysine and poly-D-lysine. In some embodiments, the poly-cationic polyamide (e.g., the at least one of the poly-L-lysine and the poly-D-lysine) have an average molecular weight of at least about 7500 Da. The poly-cationic polyamide (e.g., the at least one of the poly-L-lysine and the poly-D-lysine) may have an average molecular weight of less than about 35,000 Da (e.g., an average molecular weight of less than about 30000 Da (e.g., an average molecular weight of about 25,000 Da)). The poly-cationic polyamide (e.g., the at least one of the poly-L-lysine and the poly-D-lysine) may have a median molecular weight of at least about 15,000 Da. The poly-cationic polyamide (e.g., the at least one of the poly-L-lysine and the poly-D-lysine) may have a median molecular weight of less than about 25,000 Da (e.g., a median molecular weight of less than about 20,000 Da (e.g., a median molecular weight of about 20,000 Da). If the polycationic material is PEI, its molecular weight is preferably in the range 600-800 Daltons.

Another aspect of the invention relates to a sample preparation device including a surface including a poly-cationic polyamide or PEI bound thereto and a sample introduction passage in communication with the surface for contacting the surface with a fluidic sample.

In some embodiments, the device includes a heat source configured to heat an aqueous liquid in contact with the surface to at least about 65° C.

In some embodiments, the device includes a reservoir of liquid having a pH of at least about 10 (e.g., about 10.5 or more). The device is configured to contact the surface with the liquid (e.g., by actuating a pressure source to move the liquid).

In some embodiments, the surface comprises surfaces of a plurality of particles.

In some embodiments, the poly-cationic polyamide includes poly-L-lysine and/or poly-D-lysine.

Another aspect of the invention relates to a method for processing a sample including providing a mixture including a liquid and an amount of polynucleotide, contacting a retention member with the mixture. The retention member may be configured to preferentially retain polynucleotides as compared to polymerase chain reaction inhibitors. Substantially all of the liquid in the mixture is removed from the retention member. The polynucleotides are released from the retention member. The polynucleotide may have a size of less than about 7.5 Mbp.

The liquid may be a first liquid and removing substantially all of the liquid from the retention member may include contacting the retention member with a second liquid.

Contacting the retention member with a second liquid can include actuating a thermally actuated pressure source to apply a pressure to the second liquid. Contacting the retention member with a second liquid can include opening a thermally actuated valve to place the second liquid in fluid communication with the retention member.

The second liquid may have a volume of less than about 50 microliters.

The retention member may include a surface having a compound configured to bind polynucleotides preferentially to polymerase chain reaction inhibitors (e.g., hemoglobin, peptides, faecal compounds, humic acids, mucousol compounds, DNA binding proteins, or a saccharide).

The surface may include a poly-lysine (e.g., poly-L-lysine and/or poly-D-lysine) or PEI.

The second liquid may include a detergent (e.g., SDS).

Releasing may include heating the retention member to a temperature of at least about 50° C. (e.g., at about 65° C.). The temperature may be insufficient to boil the liquid in the presence of the retention member during heating. The temperature may be 100° C. or less (e.g., less than 100° C., about 97° C. or less). The temperature may be maintained for less than about 10 minutes (e.g., for less than about 5 minutes, for less than about 3 minutes).

The releasing may be performed without centrifugation of the retention member.

In certain embodiments, PCR inhibitors are rapidly removed from clinical samples to create a PCR-ready sample. The method may comprise the preparation of a polynucleotide-containing sample that is substantially free of inhibitors. The samples may be prepared from, e.g., crude lysates resulting from thermal, chemical, ultrasonic, mechanical, electrostatic, and other lysing techniques. The samples may be prepared without centrifugation. The samples may be prepared using microfluidic devices or on a larger scale.

Another aspect of the invention relates to a retention member, e.g., a plurality of particles such as beads, comprising bound PEI, or poly-lysine, e.g., poly-L-lysine, and related methods and systems. The retention member preferentially binds polynucleotides, e.g., DNA, as compared to inhibitors. The retention member may be used to prepare polynucleotides samples for further processing, such as amplification by polymerase chain reaction.

In certain embodiments, more than 90% of a polynucleotide present in a sample may be bound to the retention member, released, and recovered.

In certain embodiments, a polynucleotide may be bound to the retention member, released, and recovered, in less than about 10 minutes (e.g., less than about 7.5 minutes, less than about 5 minutes, or less than about 3 minutes).

A polynucleotide may be bound to a retention member, released, and recovered without subjecting the polynucleotide, retention member, and/or inhibitors to centrifugation.

Separating the polynucleotides and inhibitors generally excludes subjecting the polynucleotides, inhibitors, processing region, and/or retention member to sedimentation (e.g., centrifugation).

Another aspect of the invention relates to a microfluidic device including a channel, a first mass of a thermally responsive substance (TRS) disposed on a first side of the channel, a second mass of a TRS disposed on a second side of the channel opposite the first side of the channel, a gas pressure source associated with the first mass of the TRS. Actuation of the gas pressure source drives the first mass of the TRS into the second mass of the TRS and obstructs the channel.

The microfluidic device can include a second gas pressure source associated with the second mass of the TRS. Actuation of the second gas pressure source drives the second mass of TRS into the first mass of TRS.

At least one (e.g., both) of the first and second masses of TRS may be a wax.

Another aspect of the invention relates to a method for obstructing a channel of a microfluidic device. A mass of a TRS is heated and driven across the channel (e.g., by gas pressure) into a second mass of TRS. The second mass of TRS may also be driven (e.g., by gas pressure) toward the first mass of TRS.

Another aspect of the invention relates to an actuator for a microfluidic device. The actuator includes a channel, a chamber connected to the channel, at least one reservoir of encapsulated liquid disposed in the chamber, and a gas surrounding the reservoir within the chamber. Heating the chamber expands the reservoir of encapsulated liquid and pressurizes the gas. Typically the liquid has a boiling point of about 90° C. or less. The liquid may be a hydrocarbon having about 10 carbon atoms or fewer.

The liquid may be encapsulated by a polymer.

The actuator may include multiple reservoirs of encapsulated liquid disposed in the chamber.

The multiple reservoirs may be dispersed within a solid (e.g., a wax).

The multiple reservoirs may be disposed within a flexible enclosure (e.g., a flexible sack).

Another aspect of the invention relates to a method including pressurizing a gas within a chamber of a microfluidic to create a gas pressure sufficient to move a liquid within a channel of the microfluidic device. Pressurizing the gas typically expanding at least one reservoir of encapsulated liquid disposed within the chamber.

Expanding the at least one reservoir can include heating the chamber.

Pressurizing the gas can include expanding multiple reservoirs of encapsulated liquid.

Another aspect of the invention relates to a method for combining (e.g., mixing) first and second liquids and related devices. The device includes a mass of a temperature responsive substance (TRS) that separates first and second channels of the device. The device is configured to move a first liquid along the first channel so that a portion (e.g., a medial portion) of the first liquid is adjacent the TRS and to move a second liquid along the second channel so that a portion (e.g., a medial portion) of second liquid is adjacent the TRS. A heat source is actuated to move the TRS (e.g., by melting, dispersing, fragmenting). The medial portions of the first and second liquids typically combine without being separated by a gas interface. Typically, only a subset of the first liquid and a subset of the second liquid are combined. The liquids mix upon being moved along a mixing channel.

Another aspect of the invention relates to a lyophilized reagent particle and a method of making the particle.

In some embodiments, the lyophilized particles include multiple smaller particles each having a plurality of ligands that preferentially associate with polynucleotides as compared to PCR inhibitors. The lyophilized particles can also (or alternatively) include lysing reagents (e.g., enzymes) configured to lyse cells to release polynucleotides. The lyophilized particles can also (or alternatively) include enzymes (e.g., proteases) that degrade proteins.

Cells can be lysed by combining a solution of the cells with the lyophilized particles to reconstitute the particles. The reconstituted lysing reagents lyse the cells. The polynucleotides associate with ligands of the smaller particles. During lysis, the solution may be heated (e.g., radiatively using a lamp (e.g., a heat lamp)).

In some embodiments, lyophilized particles include reagents (e.g., primers, control plasmids, polymerase enzymes) for performing PCR.

A method for making lyophilized particles includes forming a solution of reagents of the particle and a cryoprotectant (e.g., a sugar or poly-alcohol). The solution is deposited dropwise on a chilled hydrophobic surface (e.g., a diamond film or polytetrafluoroethylene surface), without contacting a cooling agent such as liquid nitrogen. The particles freeze and are subjected to reduced pressure (typically while still frozen) for a time sufficient to remove (e.g., sublimate) the solvent. The lyophilized particles may have a diameter of about 5 mm or less (e.g., about 2.5 mm or less, about 1.75 mm or less).

Another aspect of the invention relates to a liquid reservoir capable of holding a liquid (e.g., a solvent, a buffer, a reagent, or combination thereof). In general, the reservoir can have one or more of the following features.

The reservoir can include a wall that can be manipulated (e.g., pressed or depressed) to decrease a volume within the reservoir. For example, the reservoir can include a piercing member (e.g., a needle-like or otherwise pointed or sharp member) that ruptures another portion of the reservoir (e.g., a portion of the wall) to release liquid. The piercing member can be internal to the reservoir such that the piercing member ruptures the wall from an inner surface of the reservoir (e.g., wall) outwards.

In general, the wall resists passage of liquid or vapor therethrough. In some embodiments, the wall lacks stretchiness. The wall may be flexible. The wall may be, e.g., a metallic layer, e.g., a foil layer, a polymer, or a laminate including a combination thereof.

The wall may be formed by vacuum formation (e.g., applying a vacuum and heat to a layer of material to draw the layer against a molding surface). The molding surface may be concave such that the wall is provided with a generally convex surface.

Exemplary liquids held by the reservoir include water and aqueous solutions including one or more salts (e.g., magnesium chloride, sodium chloride, Tris buffer, or combination thereof). The reservoir can retain the liquid (e.g., without substantial evaporation thereof) for a period of time (e.g., at least 6 months or at least a year). In some embodiments, less than 10% (e.g., less than about 5%) by weight of the liquid evaporates over a year.

The piercing member may be an integral part of a wall of the reservoir. For example, the reservoir can include a wall having an internal projection, which may be in contact with liquid in the reservoir. The reservoir also includes a second wall opposite the piercing member. During actuation, the piercing member is driven through the second wall (e.g., from the inside out) to release liquid.

In some embodiments, a maximum amount of liquid retained by a reservoir is less than about 1 ml. For example, a reservoir may hold about 500 microliters or less (e.g., 300 microliters or less). Generally, a reservoir holds at least about 25 microliters (e.g., at least about 50 microliters). The reservoir can introduce within about 10% of the intended amount of liquid (e.g., 50±5 µl).

The reservoir can deliver a predetermined amount of liquid that is substantially air-free (e.g., substantially gas-free). Upon introduction of the liquid, the substantially air and/or gas free liquid produces few or no bubbles large enough to obstruct movement of the liquid within the microfluidic device. Use of a piercing member internal to the reservoir can enhance an ability of the reservoir to deliver substantially air and/or gas free liquids.

In some embodiments, the reservoir can be actuated to release liquid by pressing (e.g., by one's finger or thumb or by mechanical pressure actuation). The pressure may be applied directly to a wall of the reservoir or to a plunger having a piercing member. In embodiments, minimal pressure is required to actuate the reservoir. An automated system can be used to actuate (e.g., press upon) a plurality of reservoirs simultaneously or in sequence.

In some embodiments, the reservoir does not include a piercing member. Instead, internal pressure generated within the reservoir ruptures a wall of the reservoir allowing liquid to enter the microfluidic device.

Upon actuating a reservoir to introduce liquid into the microfluidic device, liquid generally does not withdraw back into the reservoir. For example, upon actuation, the volume of the reservoir may decrease to some minimum but generally does not increase so as to withdraw liquid back into the reservoir. For example, the reservoir may stay collapsed upon actuation. In such embodiments, the flexible wall may be flexible but lack hysterisis or stretchiness. Alternatively or in combination, the reservoir may draw in air from a vent without withdrawing any of the liquid.

Actuation of the reservoir may include driving a piercing member through a wall of the reservoir.

The reservoir preserves the reactivity and composition of reagents therein (e.g., the chemicals within the reservoir may exhibit little or no change in reactivity over 6 months or a year).

The flexible wall of the reservoir can limit or prevent leaching of chemicals therethrough. The reservoir can be assembled independently of a microfluidic device and then secured to the microfluidic device.

DETAILED DESCRIPTION OF THE INVENTION

Analysis of biological samples often includes determining whether one or more polynucleotides (e.g., a DNA, RNA, mRNA, or rRNA) is present in the sample. For example, one may analyze a sample to determine whether a polynucleotide indicative of the presence of a particular pathogen is present. Typically, biological samples are complex mixtures. For example, a sample may be provided as a blood sample, a tissue sample (e.g., a swab of, for example, nasal, buccal, anal, or vaginal tissue), a biopsy aspirate, a lysate, as fungi, or as bacteria. Polynucleotides to be determined may be contained within particles (e.g., cells (e.g., white blood cells and/or red blood cells), tissue fragments, bacteria (e.g., gram positive bacteria and/or gram negative bacteria), fungi, spores). One or more liquids (e.g., water, a buffer, blood, blood plasma, saliva, urine, spinal fluid, or organic solvent) is typically part of the sample and/or is added to the sample during a processing step.

Methods for analyzing biological samples include providing a biological sample (e.g., a swab), releasing polynucleotides from particles (e.g., bacteria) of the sample, amplifying one or more of the released polynucleotides (e.g., by polymerase chain reaction (PCR)), and determining the presence (or absence) of the amplified polynucleotide(s) (e.g., by fluorescence detection). Biological samples, however, typically include inhibitors (e.g., mucosal compounds, hemoglobin, faecal compounds, and DNA binding proteins) that can inhibit determining the presence of polynucleotides in the sample. For example, such inhibitors can reduce the amplification efficiency of polynucleotides by PCR and other enzymatic techniques for determining the presence of polynucleotides. If the concentration of inhibitors is not reduced relative to the polynucleotides to be determined, the analysis can produce false negative results.

We describe methods and related systems for processing biological samples (e.g., samples having one or more polynucleotides to be determined). Typically, the methods and systems reduce the concentration of inhibitors relative to the concentration of polynucleotides to be determined.

Figure 1:
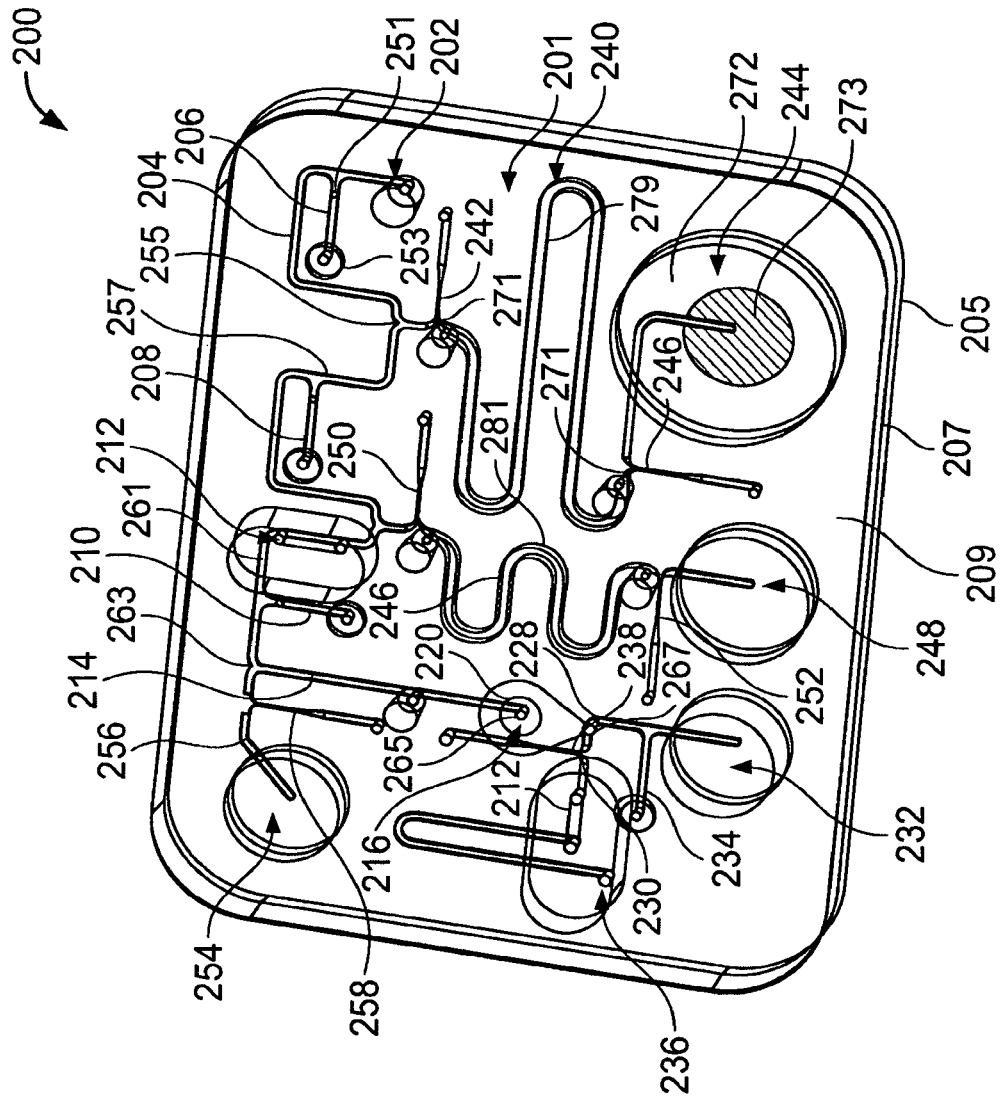
FIG. 1 is a perspective view of a microfluidic device.

Referring to FIG. 1, a microfluidic device 200 includes first, second, and third layers 205, 207, and 209 that define a microfluidic network 201 having various components configured to process a sample including one or more polynucleotides to be determined. Device 200 typically processes the sample by increasing the concentration of a polynucleotide to be determined and/or by reducing the concentration of inhibitors relative to the concentration of polynucleotide to be determined.

We now discuss the arrangement of components of network 201.

Network 201 includes an inlet 202 by which sample material can be introduced to the network and an output 236 by which a processed sample can be removed (e.g., expelled by or extracted from) network 201. A channel 204 extends between inlet 202 and a junction 255. A valve 206 is positioned along channel 204. A reservoir channel 240 extends between junction 255 and an actuator 244. Gates 242 and 246 are positioned along channel 240. A channel 257 extends between junction 255 and a junction 259. A valve 208 is positioned along channel 257. A reservoir channel 246 extends between junction 259 and an actuator 248. Gates 250 and 252 are positioned along channel 246. A channel 261 extends between junction 259 and a junction 263. A valve 210 and a hydrophobic vent 212 are positioned along channel 261. A channel 256 extends between junction 263 and an actuator 254. A gate 258 is positioned along channel 256.

A channel 214 extends between junction 263 and a processing chamber 220, which has an inlet 265 and an outlet 267. A channel 228 extends between processing chamber outlet 267 and a waste reservoir 232. A valve 234 is positioned along channel 228. A channel 230 extends between processing chamber outlet 267 and output 236.

We turn now to particular components of network 201.

Figure 2:
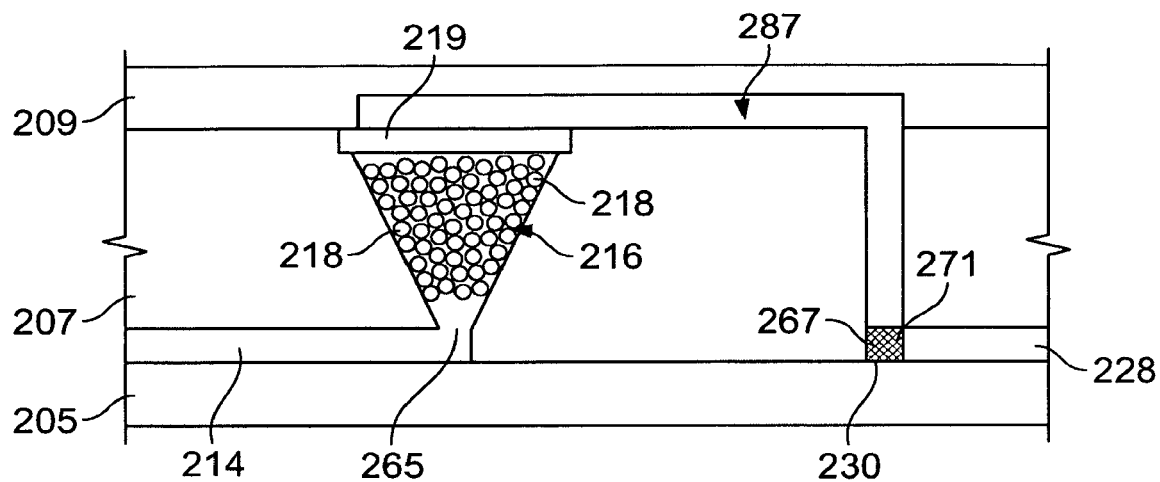
FIG. 2 is a cross-sectional view of a processing region for retaining polynucleotides and/or separating polynucleotides from inhibitors.

Referring also to FIG. 2, processing chamber 220 includes a plurality of particles (e.g., beads, microspheres) 218 configured to retain polynucleotides of the sample under a first set of conditions (e.g., a first temperature and/or first pH) and to release the polynucleotides under a second set of conditions (e.g., a second, higher temperature and/or a second, more basic pH). Typically, the polynucleotides are retained preferentially as compared to inhibitors that may be present in the sample. Particles 218 are configured as a retention member 216 (e.g., a column) through which sample material (e.g., polynucleotides) must pass when moving between the inlet 265 and outlet 267 of processing region 220.

A filter 219 prevents particles 218 from passing downstream of processing region 220. A channel 287 connects filter 219 with outlet 267. Filter 219 has a surface area within processing region 220 that is larger than the cross-sectional area of inlet 265. For example, in some embodiments, the ratio of the surface area of filter 219 within processing region 220 to the cross-sectional area of inlet 265 (which cross-sectional area is typically about the same as the cross-sectional area of channel 214) is at least about 5 (e.g., at least about 10, at least about 20, at least about 30). In some embodiments, the surface area of filter 219 within processing region 220 is at least about 1 mm$^2$ (e.g., at least about 2 mm$^2$, at least about 3 mm$^2$). In some embodiments, the cross-sectional area of inlet 265 and/or channel 214 is about 0.25 mm$^2$ or less (e.g., about 0.2 mm$^2$ or less, about 0.15 mm$^2$ or less, about 0.1 mm$^2$ or less). The larger surface area presented by filter 219 to material flowing through processing region 220 helps prevent clogging of the processing region while avoiding significant increases in the void volume (discussed below) of the processing region.

Particles 218 are modified with at least one ligand that retains polynucleotides (e.g., preferentially as compared to inhibitors). Typically, the ligands retain polynucleotides from liquids having a pH about 9.5 or less (e.g., about 9.0 or less, about 8.75 or less, about 8.5 or less). As a sample solution moves through processing region 220, polynucleotides are retained while the liquid and other solution components (e.g., inhibitors) are less retained (e.g., not retained) and exit the processing region. In general, the ligands release polynucleotides when the pH is about 10 or greater (e.g., about 10.5 or greater, about 11.0 or greater, about 11.4 or greater). Consequently, polynucleotides can be released from the ligand modified particles into the surrounding liquid.

Exemplary ligands include, for example, polyamides (e.g., poly-cationic polyamides such as poly-L-lysine, poly-D-lysine, poly-DL-ornithine) and PEI. Other ligands include, for example, intercalators, poly-intercalators, minor groove binders polyamines (e.g., spermidine), homopolymers and copolymers comprising a plurality of amino acids, and combinations thereof. In some embodiments, the ligands have an average molecular weight of at least about 5000 Da (e.g., at least about 7500 Da, of at least about 15000 Da). In some embodiments, the ligands have an average molecular weight of about 50000 Da or less (e.g., about 35000, or less, about 27500 Da or less). In some embodiments, the ligand is a poly-lysine ligand attached to the particle surface by an amide bond.

In certain embodiments, the ligands are resistant to enzymatic degradation, such as degradation by protease enzymes (e.g., mixtures of endo- and exo-proteases such as pronase) that cleave peptide bonds. Exemplary protease resistant ligands include, for example, poly-D-lysine and other ligands that are enantiomers of ligands susceptible to enzymatic attack.

Particles 218 are typically formed of a material to which the ligands can be associated. Exemplary materials from which particles 218 can be formed include polymeric materials that can be modified to attach a ligand. Typical polymeric materials provide or can be modified to provide carboxylic groups and/or amino groups available to attach ligands. Exemplary polymeric materials include, for example, polystyrene, latex polymers (e.g., polycarboxylate coated latex), polyacrylamide, polyethylene oxide, and derivatives thereof. Polymeric materials that can used to form particles 218 are described in U.S. Pat. No. 6,235,313 to Mathiowitz et al., which patent is incorporated herein by reference Other materials include glass, silica, agarose, and amino-propyl-tri-ethoxy-silane (APES) modified materials.

Exemplary particles that can be modified with suitable ligands include carboxylate particles (e.g., carboxylate modified magnetic beads (Sera-Mag Magnetic Carboxylate modified beads, Part #3008050250, Seradyn) and Polybead carboxylate modified microspheres available from Polyscience, catalog no. 09850). In some embodiments, the ligands include poly-D-lysine and the beads comprise a polymer (e.g., polycarboxylate coated latex). In other embodiments, the ligands include PEI.

In general, the ratio of mass of particles to the mass of polynucleotides retained by the particles is no more than about 25 or more (e.g., no more than about 20, no more than about 10). For example, in some embodiments, about 1 gram of particles retains about 100 milligrams of polynucleotides.

Typically, the total volume of processing region 220 (including particles 218) between inlet 265 and filter 219 is about 15 microliters or less (e.g., about 10 microliters or less, about 5 microliters or less, about 2.5 microliters or less, about 2 microliters or less). In an exemplary embodiment, the total volume of processing region 220 is about 2.3 microliters. In some embodiments, particles 218 occupy at least about 10 percent (e.g., at least about 15 percent) of the total volume of processing region 220. In some embodiments, particles 218 occupy about 75 percent or less (e.g., about 50 percent or less, about 35 percent or less) of the total volume of processing chamber 220.

In some embodiments, the volume of processing region 220 that is free to be occupied by liquid (e.g., the void volume of processing region 220 including interstices between particles 218) is about equal to the total volume minus the volume occupied by the particles. Typically, the void volume of processing region 220 is about 10 microliters or less (e.g., about 7.5 microliters or less, about 5 microliters or less, about 2.5 microliters or less, about 2 microliters or less). In some embodiments, the void volume is about 50 nanoliters or more (e.g., about 100 nanoliters or more, about 250 nanoliters or more). In an exemplary embodiment, the total volume of processing region 220 is about 2.3 microliters. For example, in an exemplary embodiment, the total volume of the processing region is about 2.3 microliters, the volume occupied by particles is about 0.3 microliters, and the volume free to be occupied by liquid (void volume) is about 2 microliters.

Particles 218 typically have an average diameter of about 20 microns or less (e.g., about 15 microns or less, about 10 microns or less). In some embodiments, particles 218 have an average diameter of at least about 4 microns (e.g., at least about 6 microns, at least about 8 microns).

In some embodiments, a volume of channel 287 between filter 219 and outlet 267 is substantially smaller than the void volume of processing region 220. For example, in some embodiments, the volume of channel 287 between filter 219 and outlet 267 is about 35% or less (e.g., about 25% or less, about 20% or less) of the void volume. In an exemplary embodiment, the volume of channel 287 between filter 219 and outlet 267 is about 500 nanoliters.

The particle density is typically at least about $10^8$ particles per milliliter (e.g., about $10^9$ particles per milliliter). For example, a processing region with a total volume of about 1 microliter may include about 103 beads.

Filter 219 typically has pores with a width smaller than the diameter of particles 218. In an exemplary embodiment, filter 219 has pores having an average width of about 8 microns and particles 218 have an average diameter of about 10 microns.

In some embodiments, at least some (e.g., all) of the particles are magnetic. In alternative embodiments, few (e.g., none) of the particles are magnetic.

In some embodiments, at least some (e.g., all) the particles are solid. In some embodiments, at least some (e.g., all) the particles are porous (e.g., the particles may have channels extending at least partially within them).

We continue discussing components of network 201.

Channels of microfluidic network 201 typically have at least one sub-millimeter cross-sectional dimension. For example, channels of network 201 may have a width and/or a depth of about 1 mm or less (e.g., about 750 microns or less, about 500 microns, or less, about 250 microns or less).

A valve is a component that has a normally open state allowing material to pass along a channel from a position on one side of the valve (e.g., upstream of the valve) to a position on the other side of the valve (e.g., downstream of the valve). Upon actuation, the valve transitions to a closed state that prevents material from passing along the channel from one side of the valve to the other. For example, valve 206 includes a mass 251 of a thermally responsive substance (TRS) that is relatively immobile at a first temperature and more mobile at a second temperature. A chamber 253 is in gaseous communication with mass 251. Upon heating gas (e.g., air) in chamber 253 and heating mass 251 of TRS to the second temperature, gas pressure within chamber 253 moves mass 251 into channel 204 obstructing material from passing therealong. Other valves of network 201 have the same structure and operate in the same fashion as valve 206.

A mass of TRS can be an essentially solid mass or an agglomeration of smaller particles that cooperate to obstruct the passage. Examples of TRS's include a eutectic alloy (e.g., a solder), wax (e.g., an olefin), polymers, plastics, and combinations thereof. The first and second temperatures are insufficiently high to damage materials, such as polymer layers of device 200. Generally, the second temperature is less than about 90° C. and the first temperature is less than the second temperature (e.g., about 70° C. or less).

A gate is a component that has a normally closed state that does not allow material to pass along a channel from a position on one side of the gate to another side of the gate. Upon actuation, the gate transitions to an open state in which material is permitted to pass from one side of the gate (e.g., upstream of the gate) to the other side of the gate (e.g., downstream of the gate). For example, gate 242 includes a mass 271 of TRS positioned to obstruct passage of material between junction 255 and channel 240. Upon heating mass 271 to the second temperature, the mass changes state (e.g., by melting, by dispersing, by fragmenting, and/or dissolving) to permit passage of material between junction 255 and channel 240.

The portion of channel 240 between gates 242 and 246 forms a fluid reservoir 279 configured to hold a liquid (e.g., water, an organic liquid, or combination thereof). During storage, gates 242 and 246 limit (e.g., prevent) evaporation of liquid within the fluid reservoir. During operation of device 200, the liquid of reservoir 279 is typically used as a wash liquid to remove inhibitors from processing region 220 while leaving polynucleotides associated with particles 218. Typically, the wash liquid is a solution having one or more additional components (e.g., a buffer, chelator, surfactant, a detergent, a base, an acid, or a combination thereof). Exemplary solutions include, for example, a solution of 10-50 mM Tris at pH 8.0, 0.5-2 mM EDTA, and 0.5%-2% SDS, a solution of 10-50 mM Tris at pH 8.0, 0.5 to 2 mM EDTA, and 0.5%-2% Triton X-100.

The portion of channel 246 between gates 250 and 252 form a fluid reservoir 281 configured like reservoir 279 to hold a liquid (e.g., a solution) with limited or no evaporation. During operation of device 200, the liquid of reservoir 281 is typically used as a release liquid into which polynucleotides that had been retained by particles 218 are released. An exemplary release liquid is an hydroxide solution (e.g., a NaOH solution) having a concentration of, for example, between about 2 mM hydroxide (e.g., about 2 mM NaOH) and about 500 mM hydroxide (e.g., about 500 mM NaOH). In some embodiments, liquid in reservoir 281 is an hydroxide solution having a concentration of about 25 mM or less (e.g., an hydroxide concentration of about 15 mM).

Reservoirs 279, 281 typically hold at least about 0.375 microliters of liquid (e.g., at least about 0.750 microliters, at least about 1.25 microliters, at least about 2.5 microliters). In some embodiments, reservoirs 279, 281 hold about 7.5 microliters or less of liquid (e.g., about 5 microliters or less, about 4 microliters or less, about 3 microliters or less).

Figure 3:
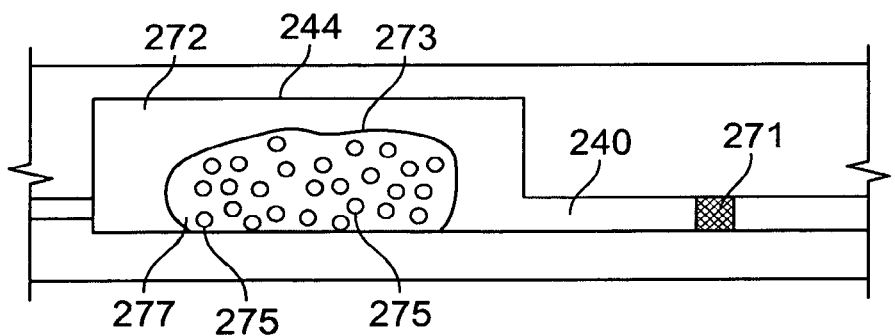
FIG. 3 is a cross-sectional view of an actuator.

An actuator is a component that provides a gas pressure that can move material (e.g., sample material and/or reagent material) between one location of network 201 and another location. For example, referring to FIG. 3, actuator 244 includes a chamber 272 having a mass 273 of thermally expansive material (TEM) therein. When heated, the TEM expands decreasing the free volume within chamber 272 and pressurizing the gas (e.g., air) surrounding mass 273 within chamber 272. Typically, gates 246 and 242 are actuated with actuator 244. Consequently, the pressurized gas drives liquid in fluid reservoir 279 towards junction 255. In some embodiments, actuator 244 can generate a pressure differential of more than about 3 psi (e.g., at least about 4 psi, at least about 5 psi) between the actuator and junction 255.

The TEM includes a plurality of sealed liquid reservoirs (e.g., spheres) 275 dispersed within a carrier 277. Typically, the liquid is a high vapor pressure liquid (e.g., isobutane and/or isopentane) sealed within a casing (e.g., a polymeric casing formed of monomers such as vinylidene chloride, acrylonitrile and methylmethacrylate). Carrier 277 has properties (e.g., flexibility and/or an ability to soften (e.g., melt) at higher temperatures) that permit expansion of the reservoirs 275 without allowing the reservoirs to pass along channel 240. In some embodiments, carrier 277 is a wax (e.g., an olefin) or a polymer with a suitable glass transition temperature. Typically, the reservoirs make up at least about 25 weight percent (e.g., at least about 35 weight percent, at least about 50 weight percent) of the TEM. In some embodiments, the reservoirs make up about 75 weight percent or less (e.g., about 65 weight percent or less, about 50 weight percent or less) of the TEM. Suitable sealed liquid reservoirs can be obtained from Expancel (Akzo Nobel).

When the TEM is heated (e.g., to a temperature of at least about 50° C. (e.g., to at least about 75° C., at least about 90° C.)), the liquid vaporizes and increases the volume of each sealed reservoir and of mass 273. Carrier 277 softens allowing mass 273 to expand. Typically, the TEM is heated to a temperature of less than about 150° C. (e.g., about 125° C. or less, about 110° C. or less, about 100° C. or less) during actuation. In some embodiments, the volume of the TEM expands by at least about 5 times (e.g., at least about 10 times, at least about 20 times, at least about 30 times).

A hydrophobic vent (e.g., vent 212) is a structure that permits gas to exit a channel while limiting (e.g., preventing) liquid from exiting the channel. Typically, hydrophobic vents include a layer of porous hydrophobic material (e.g., a porous filter such as a porous hydrophobic membrane from Osmonics) that defines a wall of the channel. As discussed below, hydrophobic vents can be used to position a microdroplet of sample at a desired location within network 201.

The hydrophobic vents of the present invention are preferably constructed so that the amount of air that escapes through them is maximized while minimizing the volume of the channel below the vent surface. Accordingly, it is preferable that the vent is constructed so as to have a hydrophobic membrane of large surface area and a shallow cross section of the microchannel below the vent surface.

Hydrophobic vents typically have a length of at least about 2.5 mm (e.g., at least about 5 mm, at least about 7.5 mm) along a channel. The length of the hydrophobic vent is typically at least about 5 times (e.g., at least about 10 times, at least about 20 times) larger than a depth of the channel within the hydrophobic vent. For example, in some embodiments, the channel depth within the hydrophobic vent is about 300 microns or less (e.g., about 250 microns or less, about 200 microns or less, about 150 microns or less).

The depth of the channel within the hydrophobic vent is typically about 75% or less (e.g., about 65% or less, about 60% or less) of than the depth of the channel upstream and downstream of the hydrophobic vent. For example, in some embodiments the channel depth within the hydrophobic vent is about 150 microns and the channel depth upstream and downstream of the hydrophobic vent is about 250 microns.

A width of the channel within the hydrophobic vent is typically at least about 25% wider (e.g., at least about 50% wider) than a width of the channel upstream from the vent and downstream from the vent. For example, in an exemplary embodiment, the width of the channel within the hydrophobic vent is about 400 microns and the width of the channel upstream and downstream from the vent is about 250 microns.

Microfluidic device 200 can be fabricated as desired. Typically, layers 205, 207, and 209 are formed of a polymeric material. Components of network 201 are typically formed by molding (e.g., by injection molding) layers 207, 209. Layer 205 is typically a flexible polymeric material (e.g., a laminate) that is secured (e.g., adhesively and/or thermally) to layer 207 to seal components of network 201. Layers 207 and 209 may be secured to one another using adhesive.

In use, device 200 is typically thermally associated with an array of heat sources configured to operate the components (e.g., valves, gates, actuators, and processing region 220) of the device. In some embodiments, the heat sources are operated by an operating system, which operates the device during use. The operating system includes a processor (e.g., a computer) configured to actuate the heat sources according to a desired protocol. Processors configured to operate microfluidic devices are described in U.S. application Ser. No. 09/819,105, filed Mar. 28, 2001, which application is incorporated herein by reference. In other embodiments, the heat sources are integral with the device itself.

Device 200 may be operated as follows. Valves of network 201 are configured in the open state. Gates of network 201 are configured in the closed state. A fluidic sample comprising polynucleotides is introduced to network 201 via inlet 202. For example, sample can be introduced with a syringe having a Luer fitting. The syringe provides pressure to initially move the sample within network 201. Sample passes along channels 204, 257, 261, and 214 to inlet 265 of processing region 220. The sample passes through processing region 220, exits via outlet 267, and passes along channel 228 to waste chamber 232. When the trailing edge (e.g., the upstream liquid-gas interface) of the sample reaches hydrophobic vent 212, pressure provided by the introduction device (e.g., the syringe) is released from network 201 stopping further motion of the sample.

Typically, the amount of sample introduced is about 500 microliters or less (e.g., about 250 microliters or less, about 100 microliters or less, about 50 microliters or less, about 25 microliters or less, about 10 microliters or less). In some embodiments, the amount of sample is about 2 microliters or less (e.g., of about 0.5 microliters or less).

Polynucleotides entering processing region 220 pass through interstices between the particles 218. Polynucleotides of the sample contact retention member 216 and are preferentially retained as compared to liquid of the sample and certain other sample components (e.g., inhibitors). Typically, retention member 220 retains at least about 50% of polynucleotides (at least about 75%, at least about 85%, at least about 90%) of the polynucleotides present in the sample that entered processing region 220. Liquid of the sample and inhibitors present in the sample exit the processing region 220 via outlet 267 and enter waste chamber 232. Processing region 220 is typically at a temperature of about 50° C. or less (e.g., 30° C. or less) during introduction of the sample.

Processing continues by washing retention member 216 with liquid of reservoir 279 to separate remaining inhibitors from polynucleotides retained by retention member 216. To wash retention member 216, valve 206 is closed and gates 242, 246 of first reservoir 240 are opened. Actuator 244 is actuated and moves wash liquid within reservoir 279 along channels 257, 261, and 214, through processing region 220, and into waste reservoir 232. The wash liquid moves sample that may have remained within channels 204, 257, 261, and 214 through the processing region and into waste chamber 232. Once the trailing edge of the wash liquid reaches vent 212, the gas pressure generated by actuator 244 is vented and further motion of the liquid is stopped.

The volume of wash liquid moved by actuator 244 through processing region 220 is typically at least about 2 times the void volume of processing region 220 (e.g., at least about 3 times the void volume) and can be about 10 times the void volume or less (e.g., about 5 times the void volume or less). Processing region is typically at a temperature of about 50° C. or less (e.g., 30° C. or less) during washing. Exemplary wash fluids include liquids discussed with respect to reservoirs 279 and 281.

Processing continues by releasing polynucleotides from retention member 216. Typically, wash liquid from reservoir 279 is replaced with release liquid (e.g., an hydroxide solution) from reservoir 281 before releasing the polynucleotides. Valve 208 is closed and gates 250, 252 are opened. Actuator 248 is actuated thereby moving release liquid within reservoir 281 along channels 261, 214 and into processing region 220 and in contact with retention member 216. When the trailing edge of release liquid from reservoir 281 reaches hydrophobic vent 212, pressure generated by actuator 248 is vented stopping the further motion of the liquid. The volume of liquid moved by actuator 248 through processing region 220 is typically at least about equal to the void volume of the processing region 220 (e.g., at least about 2 times the void volume) and can be about 10 times the void volume or less (e.g., about 5 times the void volume or less).

Once retention member 216 with retained polynucleotides has been contacted with liquid from reservoir 281, a releasing step is typically performed. Typically, the releasing step includes heating release liquid present within processing region 216. Generally, the liquid is heated to a temperature insufficient to boil liquid in the presence of the retention member. In some embodiments, the temperature is 100° C. or less (e.g., less than 100° C., about 97° C. or less). In some embodiments, the temperature is about 65° C. or more (e.g., about 75° C. or more, about 80° C. or more, about 90° C. or more). In some embodiments, the temperature maintained for about 1 minute or more (e.g., about 2 minutes or more, about 5 minutes or more, about 10 minutes or more). In some embodiments, the temperature is maintained for about 30 minutes (e.g., about 15 minutes or less, about 10 minutes or less, about 5 minutes or less). In an exemplary embodiment, processing region 220 is heated to between about 65 and 90° C. (e.g., to about 70° C.) for between about 1 and 7 minutes (e.g., for about 2 minutes).

The polynucleotides are released into the liquid present in the processing region 220 (e.g., the polynucleotides are typically released into an amount of release liquid having a volume about the same as the void volume of the processing region 220). Typically, the polynucleotides are released into about 10 microliters or less (e.g., about 5 microliters or less, about 2.5 microliters or less) of liquid.

In certain embodiments, the ratio of the volume of original sample moved through the processing region 220 to the volume of liquid into which the polynucleotides are released is at least about 10 (e.g., at least about 50, at least about 100, at least about 250, at least about 500, at least about 1000). In some embodiments, polynucleotides from a sample having a volume of about 2 ml can be retained within the processing region, and released into about 4 microliters or less (e.g., about 3 microliters or less, about 2 microliters or less, about 1 microliter or less) of liquid.

The liquid into which the polynucleotides are released typically includes at least about 50% (e.g., at least about 75%, at least about 85%, at least about 90%) of the polynucleotides present in the sample that entered processing region 220. The concentration of polynucleotides present in the release liquid may be higher than in the original sample because the volume of release liquid is typically less than the volume of the original liquid sample moved through the processing region. For example the concentration of polynucleotides in the release liquid may be at least about 10 times greater (e.g., at least about 25 times greater, at least about 100 times greater) than the concentration of polynucleotides in the sample introduced to device 200. The concentration of inhibitors present in the liquid into which the polynucleotides are released is generally less than concentration of inhibitors in the original fluidic sample by an amount sufficient to increase the amplification efficiency for the polynucleotides.

The time interval between introducing the polynucleotide containing sample to processing region 220 and releasing the polynucleotides into the release liquid is typically about 15 minutes or less (e.g., about 10 minutes or less, about 5 minutes or less).

Liquid including the released polynucleotides may be removed from the processing region 220 as follows. Valves 210 and 234 are closed. Gates 238 and 258 are opened. Actuator 254 is actuated to generate pressure that moves liquid and polynucleotides from processing region 220, into channel 230, and toward outlet 236. The liquid with polynucleotides can be removed using, for example, a syringe or automated sampling device. Depending upon the liquid in contact with retention member 216 during polynucleotide release, the solution with released polynucleotide may be neutralized with an amount of buffer (e.g., an equal volume of 25-50 mM Tris-HCl buffer pH 8.0).

While releasing the polynucleotides has been described as including a heating step, the polynucleotides may be released without heating. For example, in some embodiments, the liquid of reservoir 281 has an ionic strength, pH, surfactant concentration, composition, or combination thereof that releases the polynucleotides from the retention member.

While the polynucleotides have been described as being released into a single volume of liquid present within processing region 220, other configurations can be used. For example, polynucleotides may be released with the concomitant (stepwise or continuous) introduction of fluid into and/or through processing region 220. In such embodiments, the polynucleotides may be released into liquid having a volume of about 10 times or less (e.g., about 7.5 times or less, about 5 times or less, about 2.5 times or less, about 2 times or less) than the void volume of the processing region 220.

While reservoirs 279, 281 have been described as holding liquids between first and second gates, other configurations can be used. For example, liquid for each reservoir may be held within a pouch (e.g., a blister pack) isolated from network 201 by a generally impermeable membrane. The pouch is configured so that a user can rupture the membrane driving liquid into reservoirs 279, 281 where actuators 244, 248 can move the liquid during use.

While processing regions have been described as having microliter scale dimensions, other dimensions can be used. For example, processing regions with surfaces (e.g., particles) configured to preferentially retain polynucleotides as opposed to inhibitors may have large volumes (e.g., many tens of microliters or more, at least about 1 milliliter or more). In some embodiments, the processing region has a bench-top scale.

While processing region 220 has been described as having a retention member formed of multiple surface-modified particles, other configurations can be used. For example, in some embodiments, processing region 220 includes a retention member configured as a porous member (e.g., a filter, a porous membrane, or a gel matrix) having multiple openings (e.g., pores and/or channels) through which polynucleotides pass. Surfaces of the porous member are modified to preferentially retain polynucleotides. Filter membranes available from, for example, Osmonics, are formed of polymers that may be surface-modified and used to retain polynucleotides within processing region 220. In some embodiments, processing region 220 includes a retention member configured as a plurality of surfaces (e.g., walls or baffles) through which a sample passes. The walls or baffles are modified to preferentially retain polynucleotides.

While processing region 220 has been described as a component of a microfluidic network, other configurations can be used. For example, in some embodiments, the retention member can be removed from a processing region for processing elsewhere. For example, the retention member may be contacted with a mixture comprising polynucleotides and inhibitors in one location and then moved to another location at which the polynucleotides are removed from the retention member.

While reservoirs 275 have been shown as dispersed within a carrier, other configurations may be used. For example, reservoirs 275 can be encased within a flexible enclosure (e.g., a membrane, for example, an enclosure such as a sack). In some embodiments, reservoirs are loose within chamber 272. In such embodiments, actuator 244 may include a porous member having pores too small to permit passage of reservoirs 275 but large enough to permit gas to exit chamber 272.

Microfluidic devices with various components are described in U.S. provisional application No. 60/553,553 filed Mar. 17, 2004 by Parunak et al., which application is incorporated herein by reference.

Figure 4:
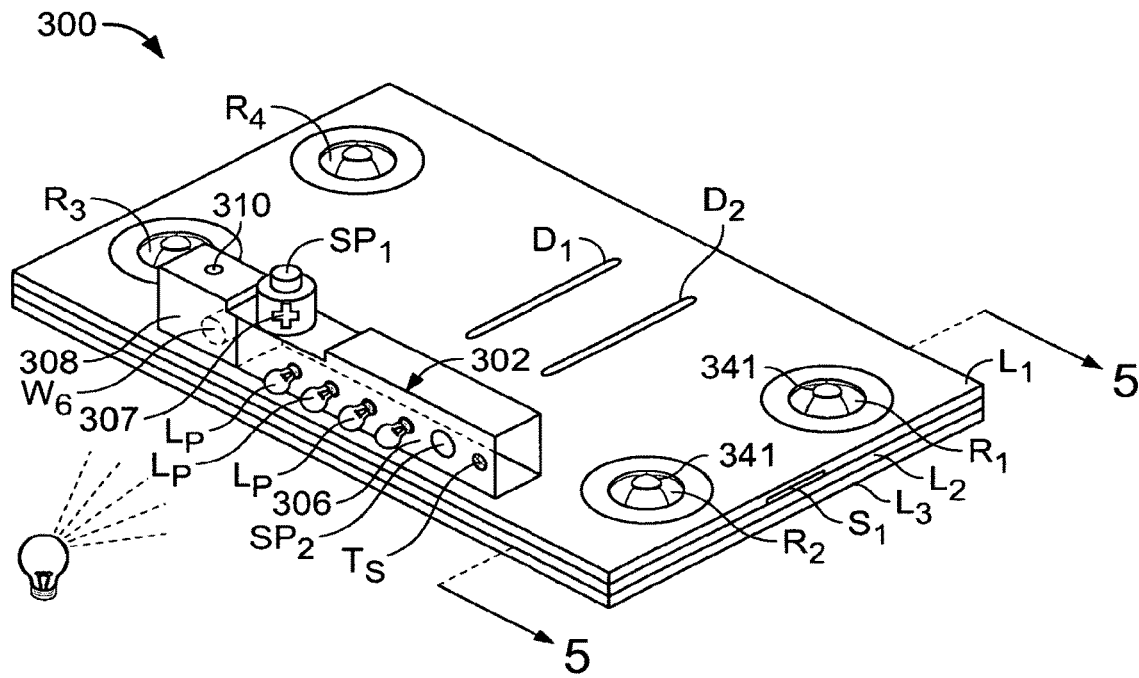
FIG. 4 is a perspective view of a microfluidic device.

While microfluidic device 300 has been described as configured to receive polynucleotides already released from cells, microfluidic devices can be configured to release polynucleotides from cells (e.g., by lysing the cells). For example, referring to FIGS. 4, 5, 6A, and 6B, a microfluidic device 300 includes a sample lysing chamber 302 in which cells are lysed to release polynucleotides therein. Microfluidic device 300 further includes substrate layers L1-L3, a microfluidic network 304 (only portions of which are seen in FIG. 4), and liquid reagent reservoirs R1-R4. Liquid reagent reservoirs R1-R4 hold liquid reagents (e.g., for processing sample material) and are connected to network 304 by reagent ports RP1-RP4.

Network 304 is substantially defined between layers L2 and L3 but extends in part between all three layers L1-L3. Microfluidic network 304 includes multiple components including channels Ci, valves Vi, double valves V'i, gates Gi, mixing gates MGi, vents Hi, gas actuators (e.g., pumps) Pi, a first processing region B1, a second processing region B2, detection zones Di, air vents AVi, and waste zones Wi.

Figure 7:
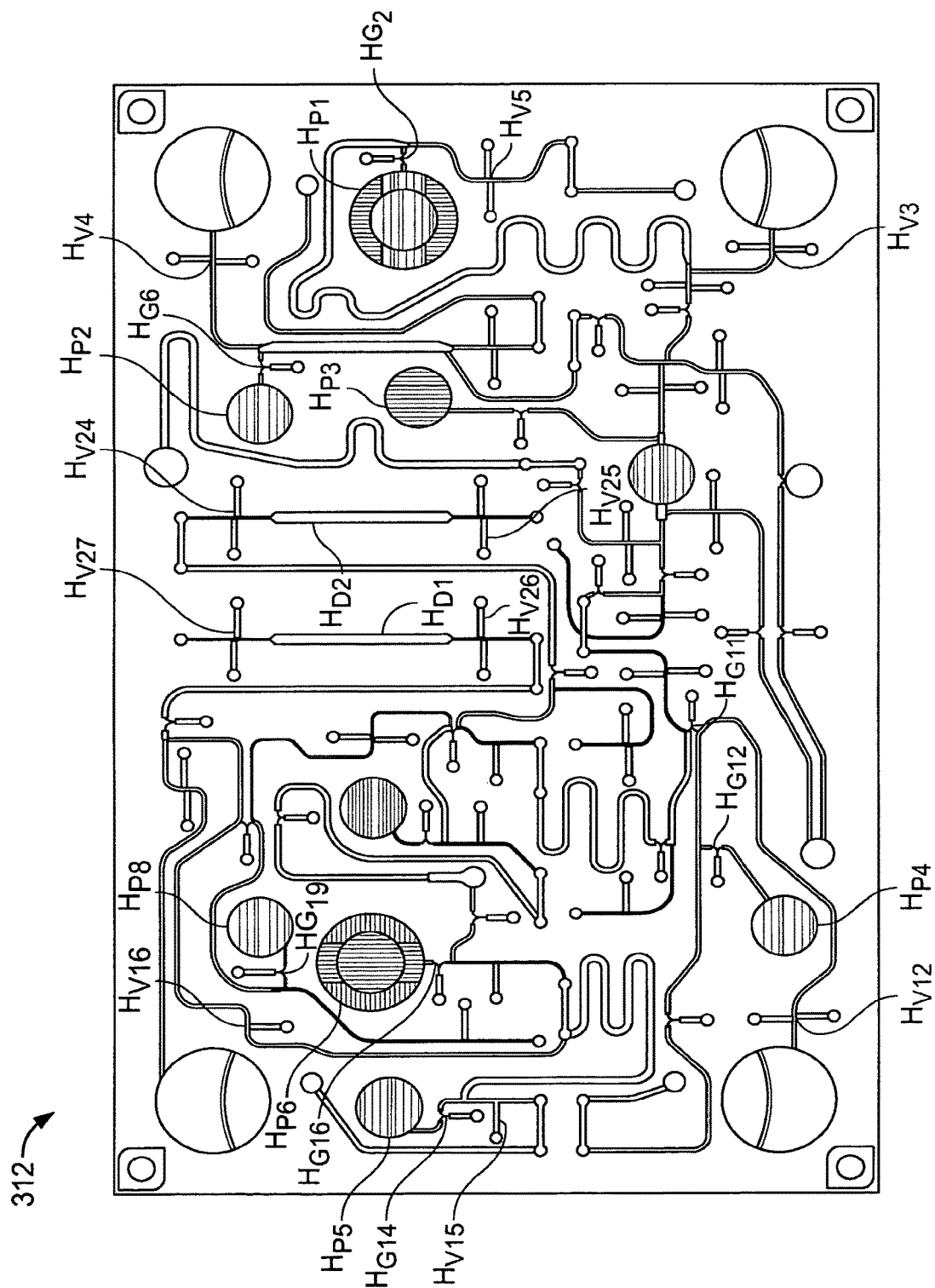
FIG. 7 illustrates an array of heat sources for operating components of the microfluidic device of FIG. 4.

Components of network 304 are typically thermally actuated. As seen in FIG. 7, a heat source network 312 includes heat sources (e.g., resistive heat sources) having locations that correspond to components of microfluidic network 304. For example, the locations of heat sources HPi correspond to the locations of actuators Pi, the locations of heat sources HGi correspond to locations of gates Gi and mixing gates MGi, the locations of heat sources HVi correspond to the locations of valves Vi and double valves V'i, and the locations of heat sources HDi correspond to the locations of processing chambers Di of network 304. In use, the components of device 300 are disposed in thermal contact with corresponding heat sources of network 312, which is typically operated using a processor as described above for device 200. Heat source network 312 can be integral with or separate from device 300 as described for device 200.

We next discuss components of microfluidic device 300.

Air vents AVi are components that allow gas (e.g., air) displaced by the movement of liquids within network 304 to be vented so that pressure buildup does not inhibit desired movement of the liquids. For example, air vent AV2 permits liquid to move along channel C14 and into channel C16 by venting gas downstream of the liquid through vent AV2.

Valves Vi are components that have a normally open state allowing material to pass along a channel from a position on one side of the valve (e.g., upstream of the valve) to a position on the other side of the valve (e.g., downstream of the valve). The valves Vi can have the same structure as valves of microfluidic device 200.

Figure 8:
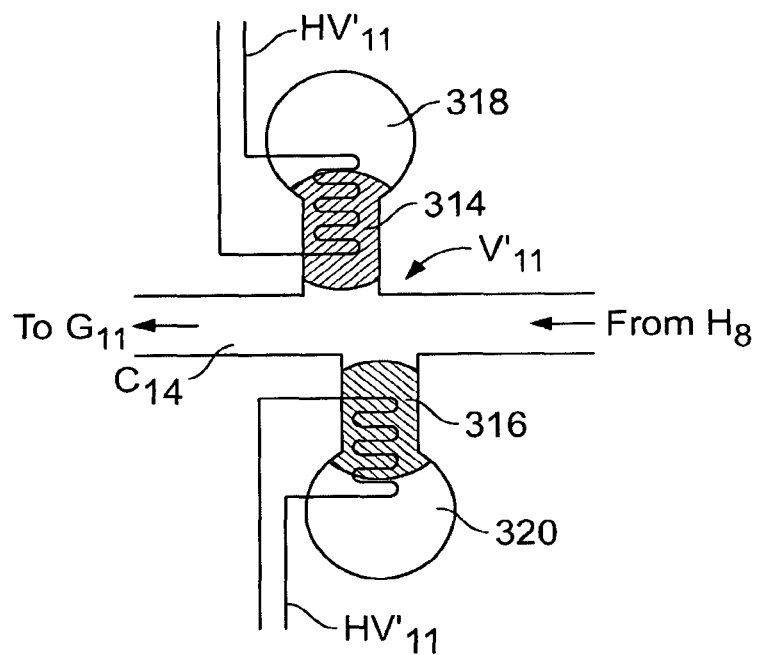
FIGS. 8 and 9 illustrate a valve in the open and closed states respectively.
Figure 9:
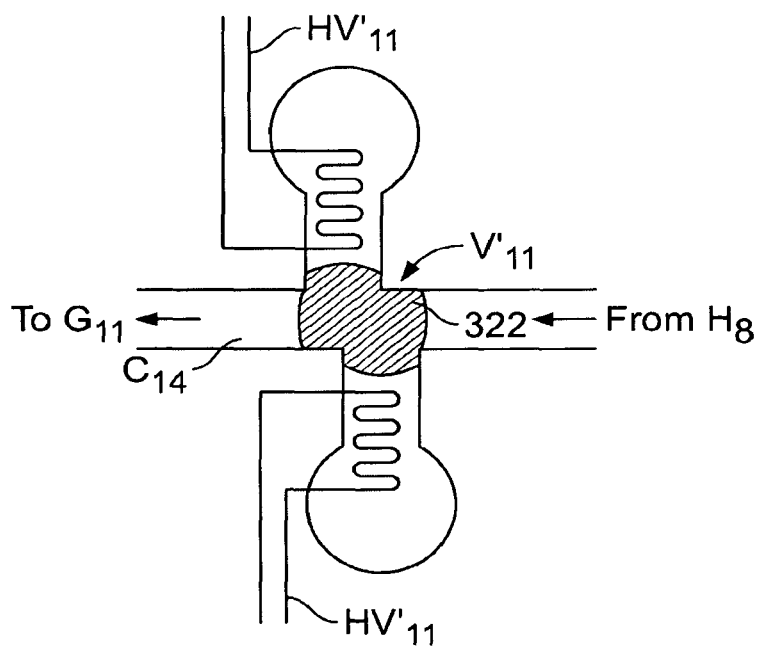

As seen in FIGS. 8 and 9, double valves V'i are also components that have a normally open state allowing material to pass along a channel from a position on one side of the valve (e.g., upstream of the valve) to a position on the other side of the valve (e.g., downstream of the valve). Taking double valve V11' of FIGS. 8 and 9 as an example, double valves Vi' include first and second masses 314, 316 of a TRS (e.g., a eutectic alloy or wax) spaced apart from one another on either side of a channel (e.g., channel C14). Typically, the TRS masses 314,316 are offset from one another (e.g., by a distance of about 50% of a width of the TRS masses or less). Material moving through the open valve passes between the first and second TRS masses 314,316. Each TRS mass 314, 316 is associated with a respective chamber 318, 320, which typically includes a gas (e.g., air).

The TRS masses 314, 316 and chambers 318, 320 of double valve Vi' are in thermal contact with a corresponding heat source HV11' of heat source network 312. Actuating heat source HV11' causes TRS masses 314, 316 to transition to a more mobile second state (e.g., a partially melted state) and increases the pressure of gas within chambers 318, 320. The gas pressure drives TRS masses 314,316 across channel C11 and closes valve HV11' (FIG. 9). Typically, masses 314, 316 at least partially combine to form a mass 322 that obstructs channel C11.

Returning to FIGS. 6A,6B, gates Gi are components that have a normally closed state that does not allow material to pass along a channel from a position on one side of the gate to another side of the gate. Gates Gi can have the same structure as described for gates of device 200.

As seen in FIG. 10A-10D, mixing gates MGi are components that allow two volumes of liquid to be combined (e.g., mixed) within network 304. Mixing gates MGi are discussed further below.

Actuators Pi are components that provide a gas pressure to move material (e.g., sample material and/or reagent material) between one location of network 304 and another location. Actuators Pi can be the same as actuators of device 200. For example, each actuator Pi includes a chamber with a mass 273 of TEM that can be heated to pressurize gas within the chamber. Each actuator Pi includes a corresponding gate Gi (e.g., gate G2 of actuator P1) that prevents liquid from entering the chamber of the actuator. The gate is typically actuated (e.g., opened) to allow pressure created in the chamber of the actuator to enter the microfluidic network.

Waste chambers Wi are components that can receive waste (e.g., overflow) liquid resulting from the manipulation (e.g., movement and/or mixing) of liquids within network 304. Typically, each waste chamber Wi has an associated air vent that allows gas displaced by liquid entering the chamber to be vented.

First processing region B1 is a component that allows polynucleotides to be concentrated and/or separated from inhibitors of a sample. Processing region B1 can be configured and operated as processing region 220 of device 200. In some embodiments, first processing region B1 includes a retention member (e.g., multiple particles (e.g., microspheres or beads), a porous member, multiple walls) having at least one surface modified with one or more ligands as described for processing region 220. For example, the ligand can include one or more polyamides (e.g., poly-cationic polyamides such as poly-L-lysine, poly-D-lysine, poly-DL-ornithine), or polyethyleneimine. In some embodiments, particles of the retention member are disposed in lysing chamber 302 and are moved into processing region B1 along with sample material.

Second processing region B2 is a component that allows material (e.g., sample material) to be combined with compounds (e.g., reagents) for determining the presence of one or more polynucleotides. In some embodiments, the compounds include one or more PCR reagents (e.g., primers, control plasmids, and polymerase enzymes). Typically, the compounds are stored within processing region as one or more lyophilized particles (e.g., pellets). The particles generally have a room temperature (e.g., about 20° C.) shelf-life of at least about 6 months (e.g., at least about 12 months). Liquid entering the second processing region B2 dissolves (e.g., reconstitutes) the lyophilized compounds.

Typically, the lyophilized particle(s) of processing region B2 have an average volume of about 5 microliters or less (e.g., about 4 microliters or less, about 3 microliters or less, about 2 microliters or less). In some embodiments, the lyophilized particle(s) of processing region B2 have an average diameter of about 4 mm or less (e.g., about 3 mm or less, about 2 mm or less) In an exemplary embodiment the lyophilized particle(s) have an average volume of about 2 microliters and an average diameter of about 1.35 mm.

Lyophilized particles for determining the presence of one or more polynucleotides typically include multiple compounds. In some embodiments, the lyophilized particles include one or more compounds used in a reaction for determining the presence of a polynucleotide and/or for increasing the concentration of the polynucleotide. For example, lyophilized particles can include one or more enzymes for amplifying the polynucleotide as by PCR.

We next discuss exemplary lyophilized particles that include exemplary reagents for the amplification of polynucleotides associated with group B *Streptococcus* (GBS) bacteria. In some embodiments, the lyophilized particles include one or more of a cryoprotectant, one or more salts, one or more primers (e.g., GBS Primer F and/or GBS Primer R), one or more probes (e.g., GBS Probe-FAM), one or more internal control plasmids, one or more specificity controls (e.g., *Streptococcus pneumoniae* DNA as a control for PCR of GBS), one or more PCR reagents (e.g., dNTPs and/or dUTPs), one or more blocking or bulking agents (e.g., non-specific proteins (e.g., bovine serum albumin (BSA), RNAseA, or gelatin), and a polymerase (e.g., glycerol-free Taq Polymerase). Of course, other components (e.g., other primers and/or specificity controls) can be used for amplification of other polynucleotides.

Cryoprotectants generally help increase the stability of the lyophilized particles and help prevent damage to other compounds of the particles (e.g., by preventing denaturation of enzymes during preparation and/or storage of the particles). In some embodiments, the cryoprotectant includes one or more sugars (e.g., one or more disaccharides (e.g., trehalose, melezitose, raffinose)) and/or one or more polyalcohols (e.g., mannitol, sorbitol).

Lyophilized particles can be prepared as desired. Typically, compounds of the lyophilized particles are combined with a solvent (e.g., water) to make a solution, which is then placed (e.g., in discrete aliquots (e.g., drops) such as by pipette) onto a chilled hydrophobic surface (e.g., a diamond film or a polytetrafluorethylene surface). In general, the temperature of the surface is reduced to near the temperature of liquid nitrogen (e.g., about −150° F. or less, about −200° F. or less, about −275° F. or less), such as by use of a cooling bath of a cryogenic agent directly underneath. It is to be noted that the solution is dispensed without contacting the cryogenic agent. The solution freezes as discrete particles. The frozen particles are subjected to a vacuum while still frozen for a pressure and time sufficient to remove the solvent (e.g., by sublimation) from the pellets.

In general, the concentrations of the compounds in the solution from which the particles are made is higher than when reconstituted in the microfluidic device. Typically, the ratio of the solution concentration to the reconstituted concentration is at least about 3 (e.g., at least about 4.5). In some embodiments, the ratio is about 6.

An exemplary solution for preparing lyophilized pellets for use in the amplification of polynucleotides indicative of the presence of GBS can be made by combining a cryoprotectant (e.g., 120 mg of trehalose as dry powder), a buffer solution (e.g., 48 microliters of a solution of 1M Tris at pH 8.4, 2.5M KCl, and 200 mM MgCl2), a first primer (e.g., 1.92 microliters of 500 micromolar GBS Primer F (Invitrogen)), a second primer (e.g., 1.92 microliters of 500 micromolar GBS Primer R (Invitrogen)), a probe (e.g., 1.92 microliters of 250 micromolar GBS Probe-FAM (IDT/Biosearch Technologies)), an control probe (e.g., 1.92 microliters of 250 micromolar Cal Orange 560 (Biosearch Technologies)), a template plasmid (e.g., 0.6 microliters of a solution of 105 copies plasmid per microliter), a specificity control (e.g., 1.2 microliters of a solution of 10 nanograms per microliter (e.g., about 5,000,000 copies per microliter) *Streptococcus pneumoniae* DNA (ATCC)), PCR reagents (e.g., 4.8 microliters of a 100 millimolar solution of dNTPs (Epicenter) and 4 microliters of a 20 millimolar solution of dUTPs (Epicenter)), a bulking agent (e.g., 24 microliters of a 50 milligram per milliliter solution of BSA (Invitrogen)), a polymerase (e.g., 60 microliters of a 5 U per microliter solution of glycerol-free Taq Polymerase (Invitrogen/Eppendorf)) and a solvent (e.g., water) to make about 400 microliters of solution. About 200 aliquots of about 2 microliters each of this solution are frozen and desolvated as described above to make 200 pellets. When reconstituted, the 200 particles make a PCR reagent solution having a total volume of about 2.4 milliliters.

Figure 5:
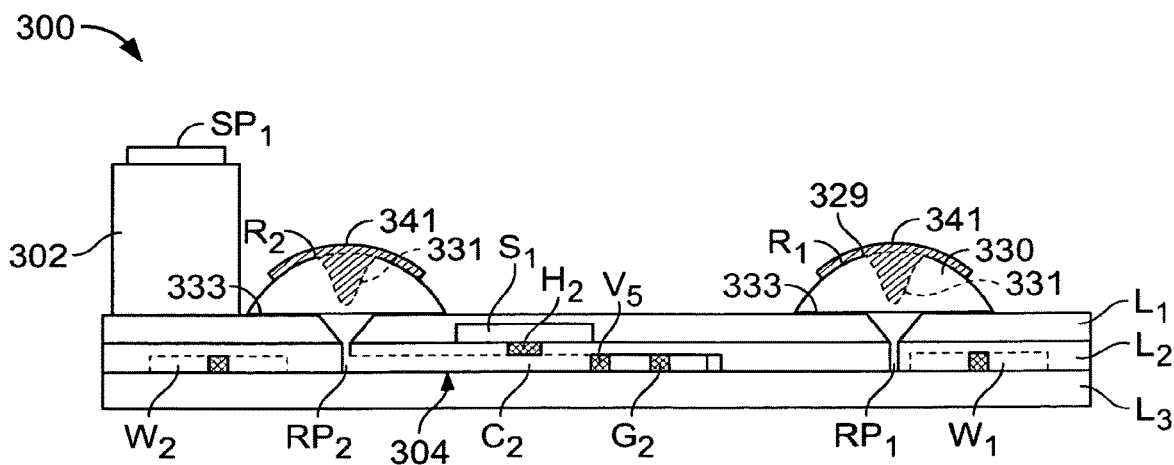
FIG. 5 is a side cross-sectional view of the microfluidic device of FIG. 4.
Figure 6A:
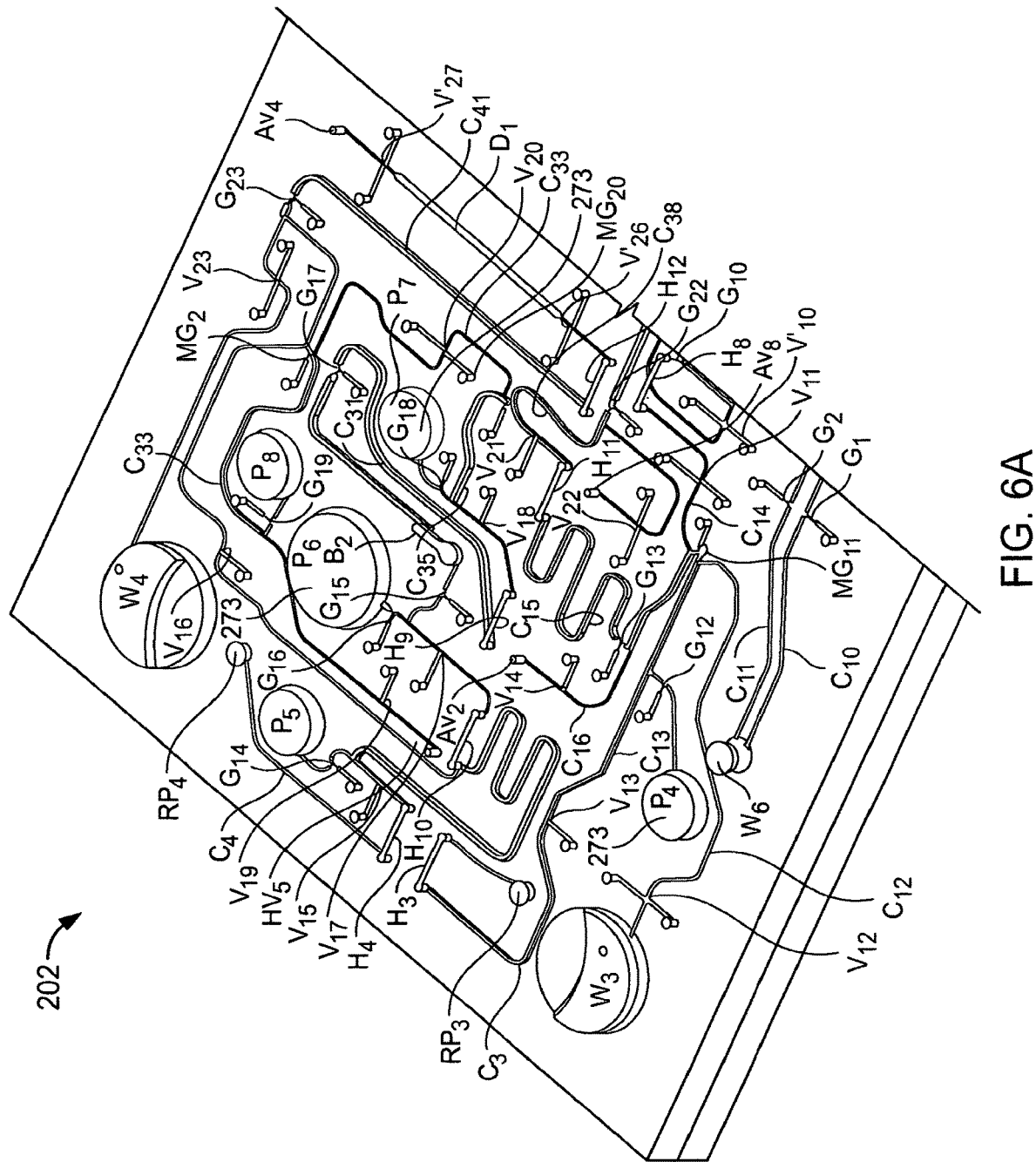
FIGS. 6A and 6B, taken together, illustrate a perspective view of a microfluidic network of the microfluidic device of FIG. 4.
Figure 6B:
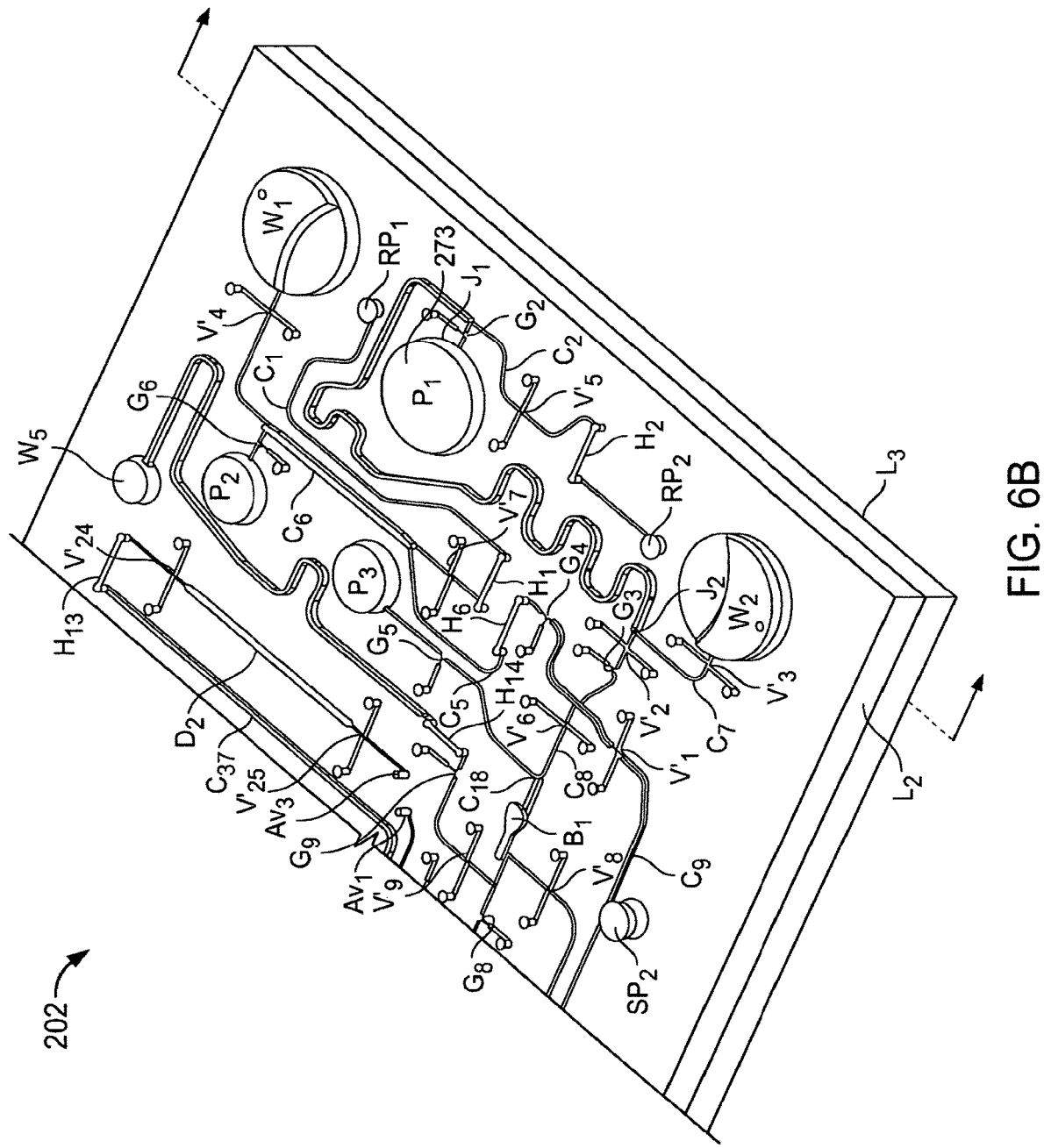

As seen in FIG. 5, reagent reservoirs Ri are configured to hold liquid reagents (e.g., water, buffer solution, hydroxide solution) separated from network 304 until ready for use. Reservoirs R1 include an enclosure 329 that defines a sealed space 330 for holding liquids. Each space 330 is separated from reagent port RPi and network 304 by a lower wall 333 of enclosure 329. A capping material 341 (e.g., a laminate, adhesive, or polymer layer) may overlie an upper wall of the enclosure.

A portion of enclosure 329 is formed as an actuation mechanism (e.g., a piercing member 331) oriented toward the lower wall 333 of each enclosure. When device 300 is to be used, reagent reservoirs Ri are actuated by depressing piercing member 331 to puncture wall 333. Piercing member 331 can be depressed by a user (e.g., with a thumb) or by the operating system used to operate device 300.

Wall 333 is typically formed of a material having a low vapor transmission rate (e.g., Aclar, a metallized (e.g. aluminum) laminate, a plastic, or a foil laminate) that can be ruptured or pierced. Reservoir 330 holds an amount of liquid suited for device 300. For example, the reservoir may hold up to about 200 microliters. The piercing member 331 may account for a portion (e.g., up to about 25%) of that volume.

In general, reservoirs Ri can be formed and filled as desired. For example, the upper wall of the enclosure can be sealed to the lower wall 333 (e.g., by adhesive and/or thermal sealing). Liquid can be introduced into the reservoir by, for example, an opening at the lower end of the piercing member 331. After filling, the opening can be sealed (e.g., by heat sealing through the localized application of heat or by the application of a sealing material (e.g., capping material 341)).

When wall 333 is punctured, fluid from the reservoir enters network 333. For example, as seen in FIGS. 5 and 6, liquid from reservoir R2 enters network 304 by port RP2 and travels along a channel C2. Gate G3 prevents the liquid from passing along channel C8. Excess liquid passes along channel C7 and into waste chamber W2. When the trailing edge of liquid from reservoir R2 passes hydrophobic vent H2, pressure created within the reservoir is vented stopping further motion of the liquid. Consequently, network 304 receives an aliquot of liquid reagent having a volume defined by the volume of channel C2 between a junction J1 and a junction J2. When actuator P1 is actuated, this aliquot of reagent is moved further within network 304. Reagent reservoirs R1, R3, and R4 are associated with corresponding channels, hydrophobic vents, and actuators.

In the configuration shown, reagent reservoir R1 typically holds a release liquid (e.g., a hydroxide solution as discussed above for device 200) for releasing polynucleotides retained within processing region B1. Reagent reservoir R2 typically holds a wash liquid (e.g., a buffer solution as discussed above for device 200) for removing un-retained compounds (e.g., inhibitors) from processing region B1 prior to releasing the polynucleotides. Reagent reservoir R3 typically holds a neutralization buffer (e.g., 25-50 mM Tris-HCl buffer at pH 8.0). Reagent reservoir R4 typically holds deionized water.

Lysing chamber 302 is divided into a primary lysing chamber 306 and a waste chamber 308. Material cannot pass from one of chambers 306, 308 into the other chamber without passing through at least a portion of network 304. Primary lysing chamber 306 includes a sample input port SP1 for introducing sample to chamber 306, a sample output port SP2 connecting chamber 306 to network 304, and lyophilized reagent LP that interact with sample material within chamber 306 as discussed below. Input port SP1 includes a one way valve that permits material (e.g., sample material and gas) to enter chamber 306 but limits (e.g., prevents) material from exiting chamber 308 by port SP1. Typically, port SP1 includes a fitting (e.g., a Luer fitting) configured to mate with a sample input device (e.g., a syringe) to form a gas-tight seal. Primary chamber 306 typically has a volume of about 5 milliliters or less (e.g., about 4 milliliters or less). Prior to use, primary chamber 306 is typically filled with a gas (e.g., air).

Waste chamber 308 includes a waste portion W6 by which liquid can enter chamber 308 from network 304 and a vent 310 by which gas displaced by liquid entering chamber 308 can exit.

Lyophilized reagent particles LP of lysing chamber 302 include one or more compounds (e.g., reagents) configured to release polynucleotides from cells (e.g., by lysing the cells). For example, particles LP can include one or more enzymes configured to reduce (e.g., denature) proteins (e.g., proteinases, proteases (e.g., pronase), trypsin, proteinase K, phage lytic enzymes (e.g., PlyGBS)), lysozymes (e.g., a modified lysozyme such as ReadyLyse), cell specific enzymes (e.g., mutanolysin for lysing group B streptococci)).

In some embodiments, particles LP alternatively or additionally include components for retaining polynucleotides as compared to inhibitors. For example, particles LP can include multiple particles 218 surface modified with ligands as discussed above for device 200. Particles LP can include enzymes that reduce polynucleotides that might compete with a polynucleotide to be determined for binding sites on the surface modified particles. For example, to reduce RNA that might compete with DNA to be determined, particles LP may include an enzyme such as an RNAase (e.g., RNAseA ISC BioExpress (Amresco)).

In an exemplary embodiment, particles LP cells include a cryoprotectant, particles modified with ligands configured to retain polynucleotides as compared to inhibitors, and one or more enzymes.

Typically, particles LP have an average volume of about 35 microliters or less (e.g., about 27.5 microliters or less, about 25 microliters or less, about 20 microliters or less). In some embodiments, the particles LP have an average diameter of about 8 mm or less (e.g., about 5 mm or less, about 4 mm or less) In an exemplary embodiment the lyophilized particle(s) have an average volume of about 20 microliters and an average diameter of about 3.5 mm.

Particles LP can be prepared as desired. Typically, the particles are prepared using a cryoprotectant and chilled hydrophobic surface as described above. For example, a solution for preparing particles LP can be prepared by combining a cryoprotectant (e.g., 6 grams of trehalose), a plurality of particles modified with ligands (e.g., about 2 milliliters of a suspension of carboxylate modified particles with poly-D-lysine ligands), a protease (e.g., 400 milligrams of pronase), an RNAase (e.g., 30 milligrams of RNAseA (activity of 120 U per milligram), an enzyme that digests peptidoglycan (e.g., ReadyLyse (e.g., 160 microliters of a 30000 U per microliter solution of ReadyLyse)), a cell specific enzyme (e.g., mutanolysin (e.g., 200 microliters of a 50 U per microliter solution of mutanolysin), and a solvent (e.g., water) to make about 20 milliliters. About 1000 aliquots of about 20 microliters each of this solution are frozen and desolvated as described above to make 1000 pellets. When reconstituted, the pellets are typically used to make a total of about 200 milliliters of solution.

In use, device 300 can be operated as follows. Valves Vi and Vi' of network 304 are configured in the open state. Gates Gi and mixing gates MGi of network 304 are configured in the closed state. Reagent ports R1-R4 are depressed to introduce liquid reagents into network 304 as discussed above. A sample is introduced to lysing chamber 302 via port SP1 and combined with lyophilized particles LP within primary lysing chamber 306. Typically, the sample includes a combination of particles (e.g., cells) and a buffer solution. For example, an exemplary sample includes about 2 parts whole blood to 3 about parts buffer solution (e.g., a solution of 20 mM Tris at pH 8.0, 1 mM EDTA, and 1% SDS). Another exemplary sample includes group B streptococci and a buffer solution (e.g., a solution of 20 mM Tris at pH 8.0, 1 mM EDTA, and 1% Triton X-100).

In general, the volume of sample introduced is smaller than the total volume of primary lysing chamber 306. For example, the volume of sample may be about 50% or less (e.g., about 35% or less, about 30% or less) of the total volume of chamber 306. A typical sample has a volume of about 3 milliliters or less (e.g., about 1.5 milliliters or less). A volume of gas (e.g., air) is generally introduced to primary chamber 306 along with the sample. Typically, the volume of gas introduced is about 50% or less (e.g., about 35% or less, about 30% or less) of the total volume of chamber 306. The volume of sample and gas combine to pressurize the gas already present within chamber 306. Valve 307 of port SP1 prevents gas from exiting chamber 306. Because gates G3, G4, G8, and G10 are in the closed state, the pressurized sample is prevented from entering network 304 via port SP2.

The sample dissolves particles LP in chamber 306. Reconstituted lysing reagents (e.g., ReadyLyse, mutanolysin) begin to lyse cells of the sample releasing polynucleotides. Other reagents (e.g., protease enzymes such as pronase) begin to reduce or denature inhibitors (e.g., proteins) within the sample. Polynucleotides from the sample begin to associate with (e.g., bind to) ligands of particles 218 released from particles LP. Typically, the sample within chamber 306 is heated (e.g., to at least about 50° C., to at least about 60° C.) for a period of time (e.g., for about 15 minutes or less, about 10 minutes or less, about 7 minutes or less) while lysing occurs. In some embodiments, optical energy is used at least in part to heat contents of lysing chamber 306. For example, the operating system used to operate device 300 can include a light source (e.g., a lamp primarily emitting light in the infrared) disposed in thermal and optical contact with chamber 306. Chamber 306 includes a temperature sensor TS used to monitor the temperature of the sample within chamber 306. The lamp output is increased or decreased based on the temperature determined with sensor TS.

Continuing with the operation of device 300, G2 is actuated (e.g., opened) providing a path between port SP2 of primary lysing chamber 306 and port W6 of lysing waste chamber 308. The path extends along channel C9, channel C8, through processing region B1, and channel C11. Pressure within chamber 306 drives the lysed sample material (containing lysate, polynucleotides bound to particles 218, and other sample components) along the pathway. Particles 218 (with polynucleotides) are retained within processing region B1 (e.g., by a filter) while the liquid and other components of the sample flow into waste chamber 308. After a period of time (e.g., between about 2 and about 5 minutes), the pressure in lysing chamber 306 is vented by opening gate G1 to create a second pathway between ports SP2 and W6. Double valves V1' and V8' are closed to isolate lysing chamber 302 from network 304.

Operation of device 300 continues by actuating pump P1 and opening gates G2, G3 and G9. Pump P1 drives wash liquid in channel C2 downstream of junction J1 through processing region B1 and into waste chamber W5. The wash liquid removes inhibitors and other compounds not retained by particles 218 from processing region B1. When the trailing edge of the wash liquid (e.g., the upstream interface) passes hydrophobic vent H14, the pressure from actuator P1 vents from network 304, stopping further motion of the liquid. Double valves V2' and V9' are closed.

Operation continues by actuating pump P2 and opening gates G6, G4 and G8 to move release liquid from reagent reservoir R1 into processing region B1 and into contact with particles 218. Air vent AV1 vents pressure ahead of the moving release liquid. Hydrophobic vent H6 vents pressure behind the trailing edge of the release liquid stopping further motion of the release liquid. Double valves V6' and V10' are closed.

Operation continues by heating processing region B1 (e.g., by heating particles 218) to release the polynucleotides from particles 218. The particles can be heated as described above for device 200. Typically, the release liquid includes about 15 mM hydroxide (e.g., NaOH solution) and the particles are heated to about 70° C. for about 2 minutes to release the polynucleotides from the particles 218.

Operation continues by actuating pump P3 and opening gates G5 and G10 to move release liquid from process region B1 downstream. Air vent AV2 vents gas pressure downstream of the release liquid allowing the liquid to move into channel C16. Hydrophobic vent H8 vents pressure from upstream of the release liquid stopping further movement. Double valve V11' and valve V14 are closed.

Figure 10A:
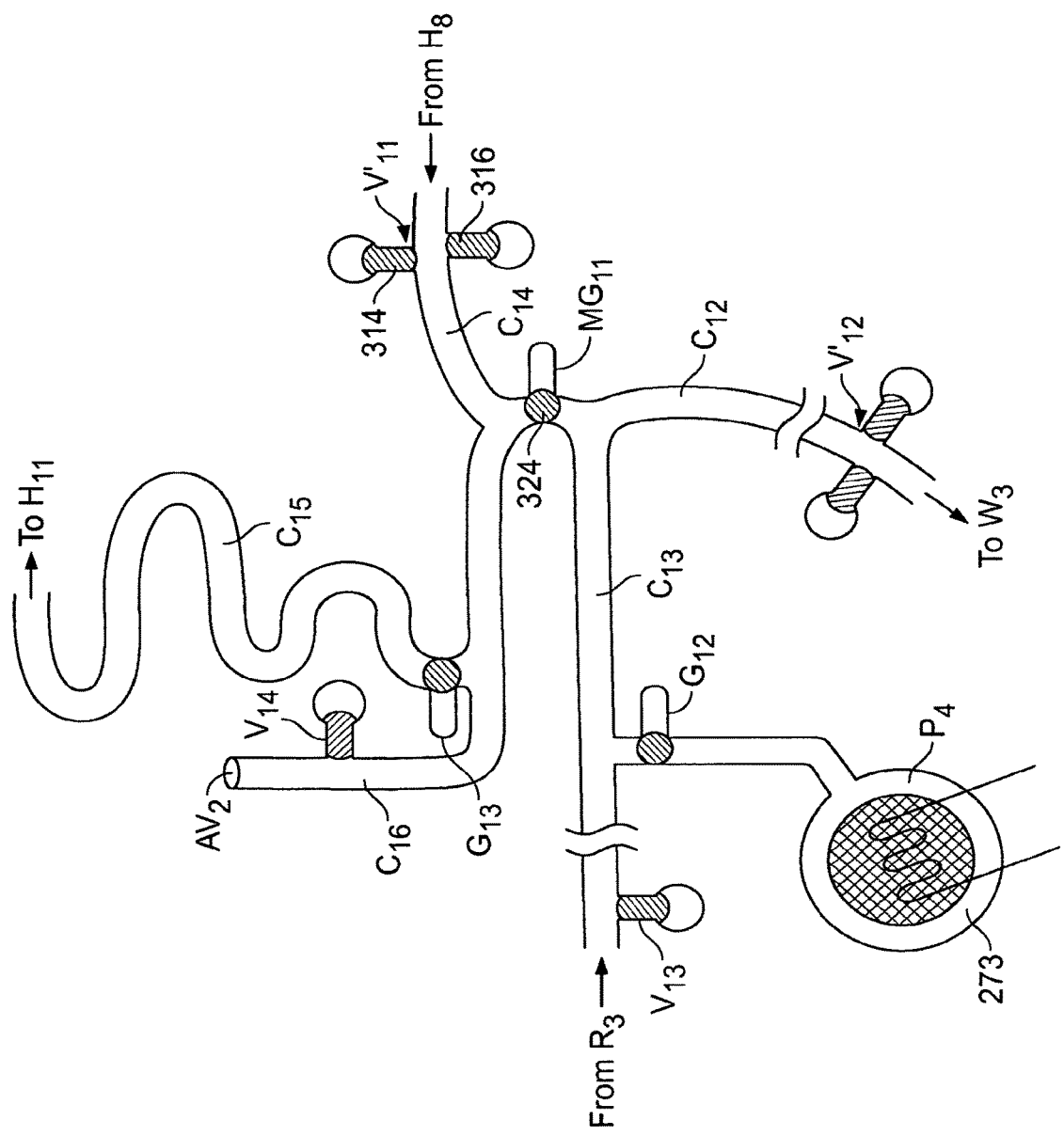
FIG. 10A-10D illustrate a mixing gate of the microfluidic network of FIGS. 6A and 6B and adjacent regions of the network.
Figure 10B:
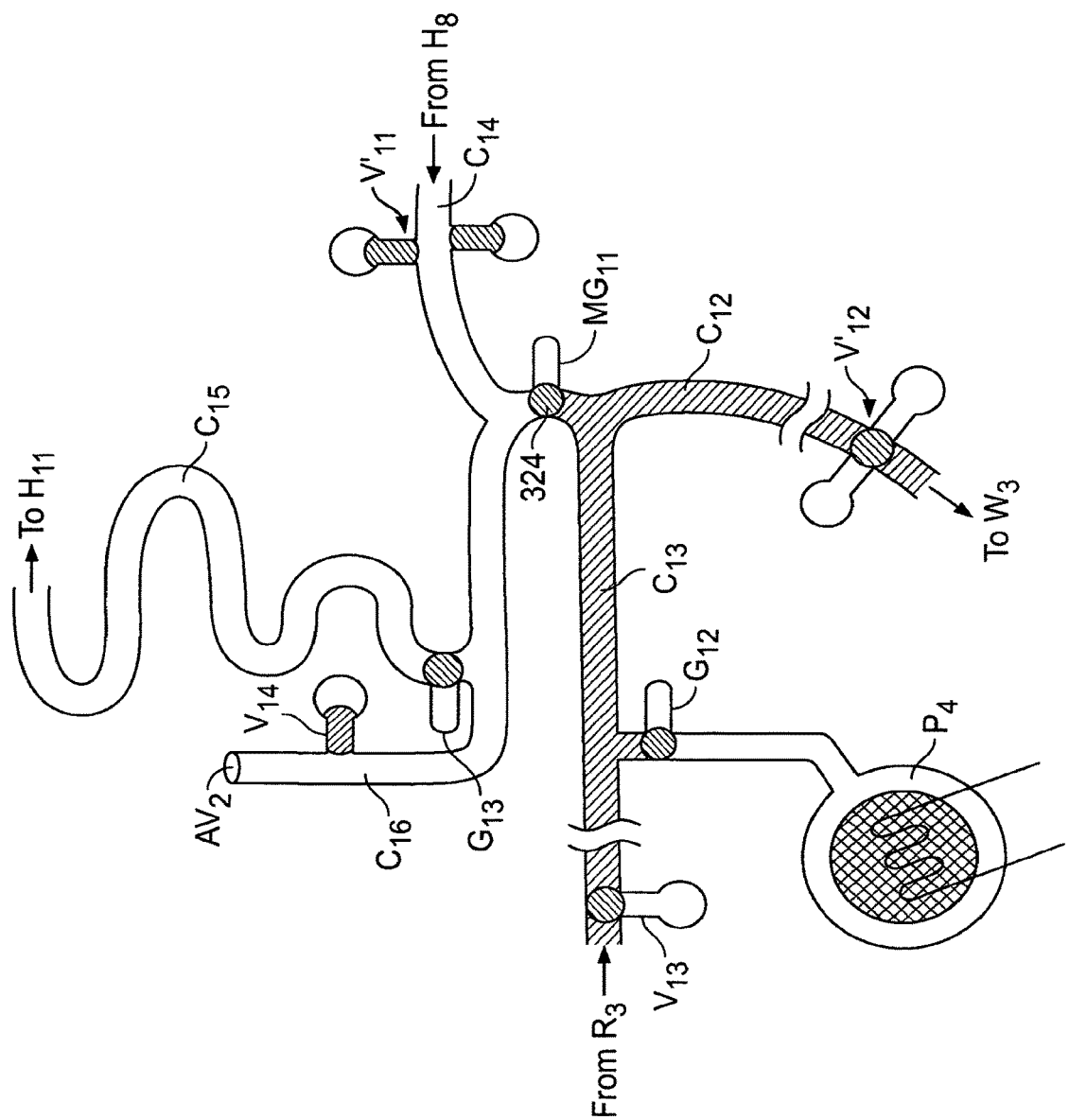

Referring to FIG. 10A-10D, mixing gate MG11 is used to mix a portion of release liquid including polynucleotides released from particles 218 and neutralization buffer from reagent reservoir R3. FIG. 10A shows the mixing gate MG11 region prior to depressing reagent reservoir R3 to introduce the neutralization buffer into network 304. FIG. 10B shows the mixing gate MG11 region, after the neutralization buffer has been introduced into channels C13 and C12. Double valve V13' is closed to isolate network 304 from reagent reservoir R3. Double valve V12' is closed to isolate network 304 from waste chamber W3. The neutralization buffer contacts one side of a mass 324 of TRS of gate MG11.

Figure 10C:
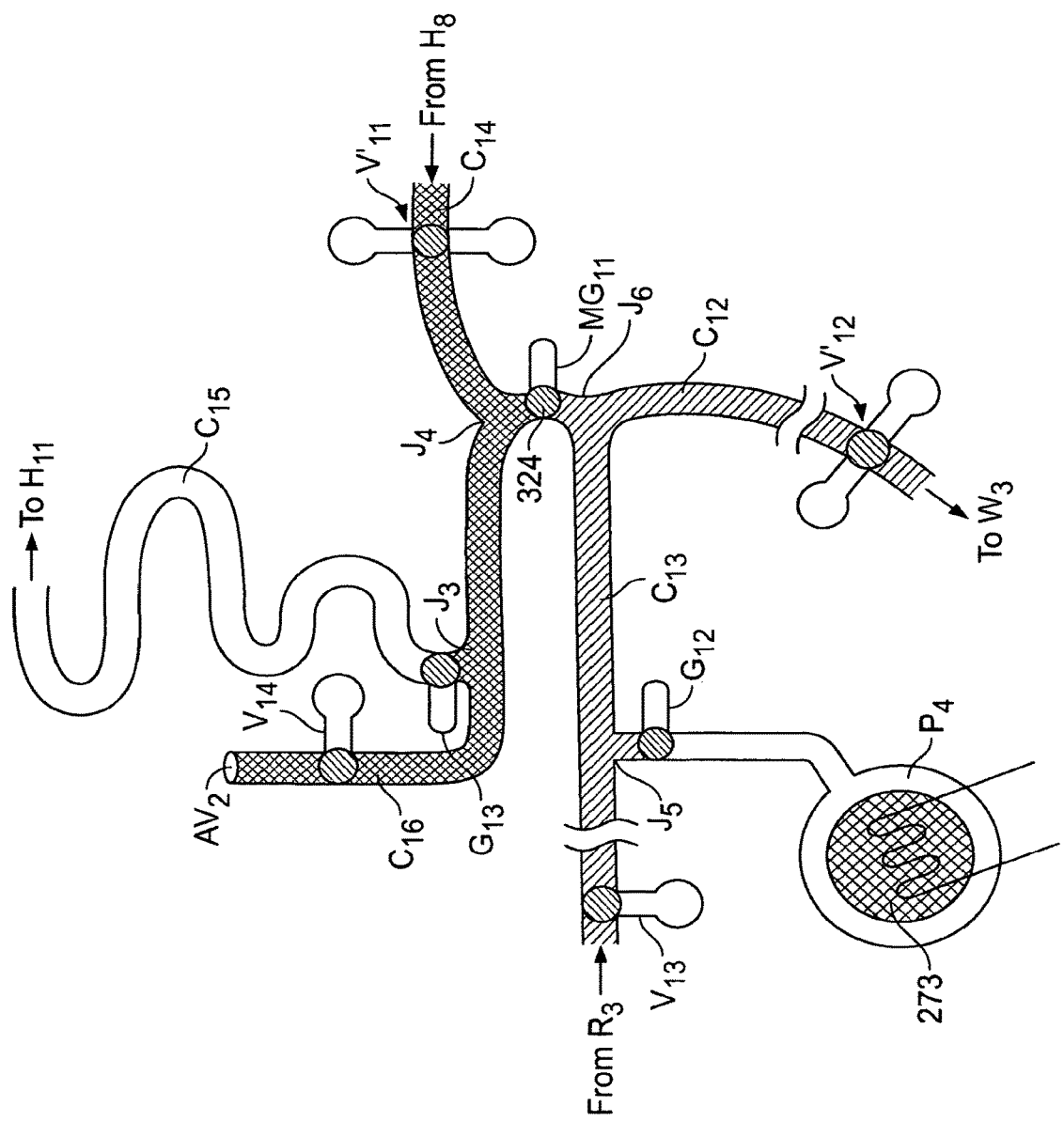

FIG. 10c shows the mixing gate MG11 region after release liquid has been moved into channel C16. The dimensions of microfluidic network 304 (e.g., the channel dimensions and the position of hydrophobic vent H8) are configured so that the portion of release liquid positioned between junctions J3 and J4 of channels C16 and C14 corresponds approximately to the volume of liquid in contact with particles 218 during the release step. In some embodiments, the volume of liquid positioned between junctions J3 and J4 is less than about 5 microliters (e.g., about 4 microliters or less, about 2.5 microliters or less). In an exemplary embodiment the volume of release liquid between junctions J3 and J4 is about 1.75 microliters. Typically, the liquid between junctions J3 and J4 includes at least about 50% of polynucleotides (at least about 75%, at least about 85%, at least about 90%) of the polynucleotides present in the sample that entered processing region B1. Valve V14 is closed to isolate network 304 from air vent AV2.

Figure 10D:
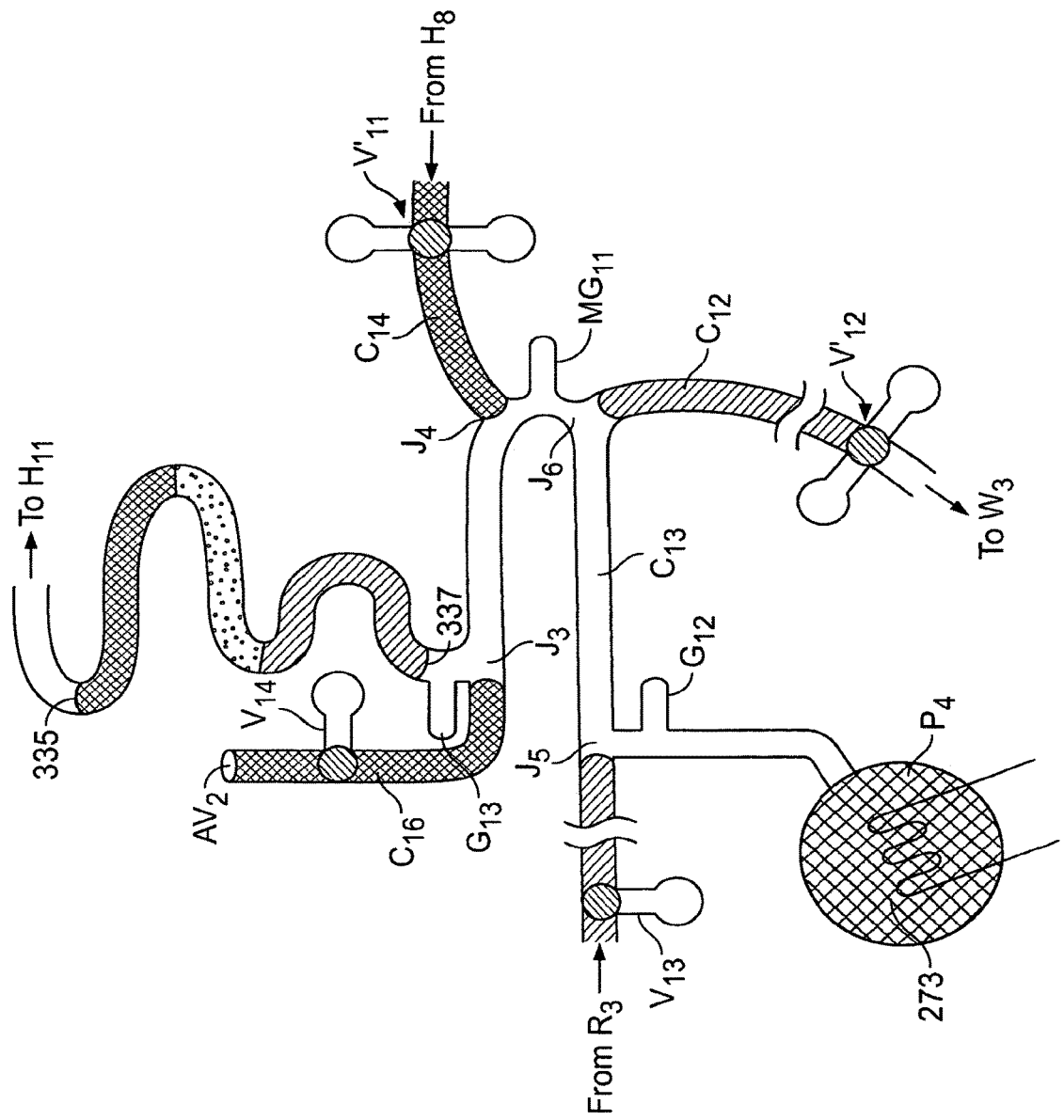

Before actuating mixing gate MG11, the release liquid at junction J4 and the neutralization buffer at a junction J6 between channels C13 and C12 are separated only by mass 324 of TRS (e.g., the liquids are not spaced apart by a volume of gas). To combine the release liquid and neutralization buffer, pump P4 and gates G12, G13, and MG11 are actuated. Pump P4 drives the volume of neutralization liquid between junctions J5 and J6 and the volume of release liquid between junctions J4 and J3 into mixing channel C15 (FIG. 10D). Mass 324 of TRS typically disperses and/or melts allowing the two liquids to combine. The combined liquids include a downstream interface 335 (formed by junction J3) and an upstream interface (formed by junction J5). The presence of these interfaces allows more efficient mixing (e.g., recirculation of the combined liquid) than if the interfaces were not present. As seen in FIG. 10D, mixing typically begins near the interface between the two liquids. Mixing channel C15 is typically at least about as long (e.g., at least about twice as long) as a total length of the combined liquids within the channel.

The volume of neutralization buffer combined with the release liquid is determined by the channel dimensions between junction J5 and J6. Typically, the volume of combined neutralization liquid is about the same as the volume of combined release liquid. In some embodiments, the volume of liquid positioned between junctions J5 and J6 is less than about 5 microliters (e.g., about 4 microliters or less, about 2.5 microliters or less). In an exemplary embodiment the volume of release liquid between junctions J5 and J6 is about 2.25 microliters (e.g., the total volume of release liquid and neutralization buffer is about 4 microliters).

Returning to FIGS. 6A, 6B, the combined release liquid and neutralization buffer move along mixing channel C15 and into channel C32 (vented downstream by air vent AV8). Motion continues until the upstream interface of the combined liquids passes hydrophobic vent H11, which vents pressure from actuator P4 stopping further motion of the combined liquids.

Continuing with operation of device 300, actuator P5 and gates G14, G15 and G17 are actuated to dissolve the lyophilized PCR particle present in second processing region B2 in water from reagent reservoir R4. Hydrophobic vent H10 vents pressure from actuator P5 upstream of the water stopping further motion. Dissolution of a PCR-reagent pellet typically occurs in about 2 minutes or less (e.g., in about 1 minute or less). Valve V17 is closed.

Continuing with operation of device 300, actuator P6 and gate G16 are actuated to drive the dissolved compounds of the lyophilized particle from processing region B2 into channel C31, where the dissolved reagents mix to form a homogenous dissolved lyophilized particle solution. Actuator P6 moves the solution into channels C35 and C33 (vented downstream by air vent AV5). Hydrophobic vent H9 vents pressure generated by actuator P6 upstream of the solution stopping further motion. Valves V18, V19, V20', and V22' are closed.

Continuing with operation of device 300, actuator P7 and gates G18, MG20 and G22 are actuated to combine (e.g., mix) a portion of neutralized release liquid in channel 32 between gate MG20 and gate G22 and a portion of the dissolved lyophilized particle solution in channel C35 between gate G18 and MG20. The combined liquids travel along a mixing channel C37 and into detection region D2. An air vent AV3 vents gas pressure downstream of the combined liquids. When the upstream interface of the combined liquids passes hydrophobic vent H13, the pressure from actuator P7 is vented and the combined liquids are positioned within detection region D2.

Actuator P8 and gates MG2, G23, and G19 are actuated to combine a portion of water from reagent reservoir R4 between MG2 and gate G23 with a second portion of the dissolved lyophilized particle solution in channel C33 between gate G19 and MG2. The combined liquids travel along a mixing channel C41 and into detection region D1. An air vent AV4 vents gas pressure downstream of the combined liquids. When the upstream interface of the combined liquids passes hydrophobic vent H12, the pressure from actuator P8 is vented and the combined liquids are positioned within detection region D1.

Continuing with operation of device 300, double valves V26' and V27' are closed to isolate detection region D1 from network 304 and double valves V24' and V25' are closed to isolate detection region D2 from network 304. The contents of each detection region (neutralized release liquid with sample polynucleotides in detection region D2 with PCR reagents from dissolved lyophilized particle solution and deionized water with PCR reagents from dissolved lyophilized particle solution in detection region D1) are subjecting to heating and cooling steps to amplify polynucleotides (if present in detection region D2). The double valves of each detection region prevent evaporation of the detection region contents during heating. The amplified polynucleotides are typically detected using fluorescence detection.

While reservoirs have been shown as having a piercing member formed of a wall of the reservoir, other configurations are possible. For example, in some embodiments, the reservoir includes a needle-like piercing member that extends through an upper wall of the reservoir into the sealed space toward a lower wall of the reservoir. The upper wall of the reservoir may be sealed at the needle-like piercing member (e.g., with an adhesive, an epoxy). In use, the upper wall is depressed driving the piercing member through the lower wall forcing liquid in the sealed space to enter a microfluidic network.

While reservoirs have been described as including an actuation mechanism (e.g., a piercing member), other configurations are possible. For example, in some embodiments, a lower wall of the sealed space of the reservoir includes a weakened portion that overlies an opening to a microfluidic network. The lower wall material (e.g., laminate, polymer film, or foil) that overlies the opening is thick enough to prevent loss of the liquid within the sealed space but thin enough to rupture upon the application of pressure to the liquid therein. Typically, the material overlying the opening is thinner than the adjacent material. Alternatively, or in addition, the weakened material can be formed by leaving this material relatively unsupported as compared to the surrounding material of the lower wall.

Figure 11A:
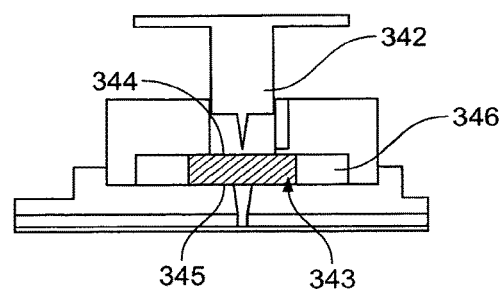
FIGS. 11A-11C illustrate a reservoir with actuation mechanism.

While reservoirs have been described as having a sealed spaced formed in part by a wall of the sealed space, other configurations are possible. For example, referring to FIG. 11A, a reservoir includes a plunger-like actuation mechanism (e.g., a piercing member 342) and a gasket-like sealed space 343 having upper and lower layers 344, 345 respectively (e.g., upper and lower laminate layers). Liquid is sealed between the upper and lower layers. The sealed space can be surrounded by a supporting structure 346 (e.g., a toroidal gasket) that supports the sealed space at its upper and lower peripheral surfaces.

Figure 11B:
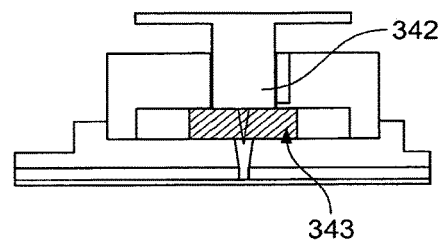

Referring to FIG. 11B, piercing member 342 is shown as being depressed until the piercing member 342 has pierced both the upper and lower layers bringing the liquid into communication with the microfluidic network. A vent 346 adjacent the plunger allows gas trapped between the piercing member and the upper layer of the sealed space to escape without being forced into the microfluidic network.

Figure 11C:
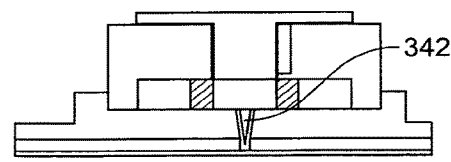

Referring to FIG. 11C, piercing member 342 is shown as fully actuated. A portion of the piercing member has displaced a corresponding volume of liquid from the sealed space and introduced the predetermined volume of liquid into the microfluidic device.

Figure 12A:
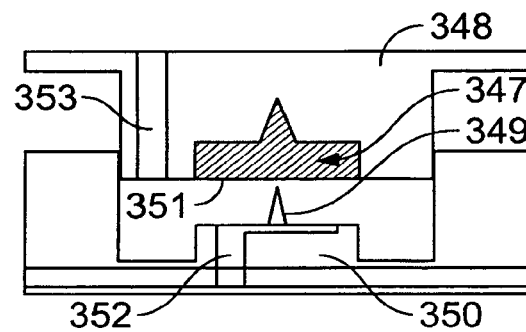
FIGS. 12A-12C illustrate a reservoir with actuation mechanism.

While the reservoirs have been described as having a sealed space that may be stationary with respect to a piercing member, other configurations are possible. For example, FIG. 12A illustrates a reservoir having a sealed space 347 that is secured with (e.g., integral with) respect to an actuation mechanism having a movable member 348 (e.g., a plunger) and a piercing member 349 supported by a piercing member support 350 that are stationary with respect to the sealed space. Typically, the sealed space is defined by a cavity within the movable member and a lower wall 351 that seals liquid within the sealed space. Piercing member is configured to rupture the lower wall when the movable member is depressed. Piercing member support has a shape generally complementary to the cavity of the movable member. Piercing member support includes a channel 352 connected to a microfluidic network to allow fluid released from the enclosed space to enter the microfluidic network.

Figure 12B:
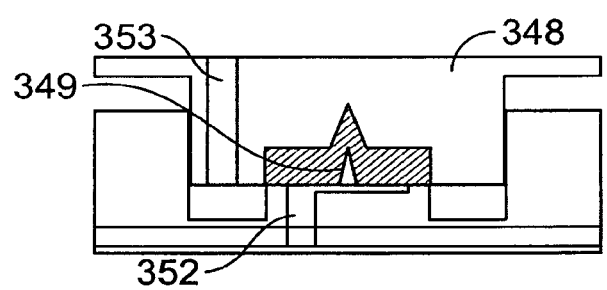
Figure 12C:
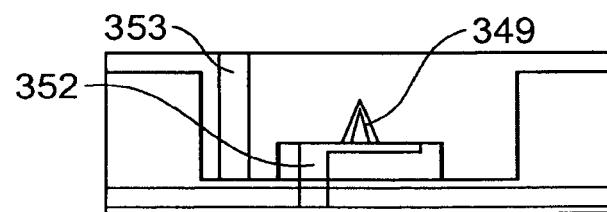

Referring to FIG. 12B, the movable member has been depressed so that the piercing member has just ruptured the lower layer of the sealed space. Referring to FIG. 12C, the reservoir has been fully depressed onto the piercing member and piercing member support. The volume of fluid displaced from the reservoir generally corresponds to the volume of the piercing member support that enters the enclosed space. A channel 353 allows air displaced by the moveable member to exit.

Figure 13:
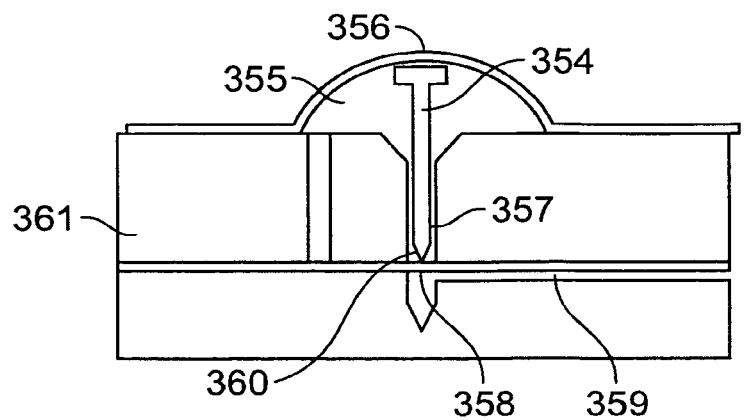
FIG. 13 illustrates a reservoir with actuation mechanism.

While reservoirs have been described as having a piercing member that is secured with respect to some portion of the reservoir, other configurations are possible. For example, referring to FIG. 13, a reservoir includes an actuation mechanism 354 (e.g., a piercing member such as a needle-like piercing member) that is unsecured with respect to the reservoir. A sealed space 355 of the reservoir is defined by an upper wall 356 and includes a channel 357 extending through a portion of a substrate 361 in which a microfluidic network is defined. A lower wall 358 of the sealed space separates the sealed space from a channel 359 of the microfluidic network. The piercing member occupies the channel 357 of the sealed space so that the piercing tip 360 of the piercing member rests against the lower wall 358. Depressing the upper wall 356 of the reservoir drives the piercing member 354 through the lower wall and forces liquid within the sealed space into the microfluidic network.

Figure 14A:
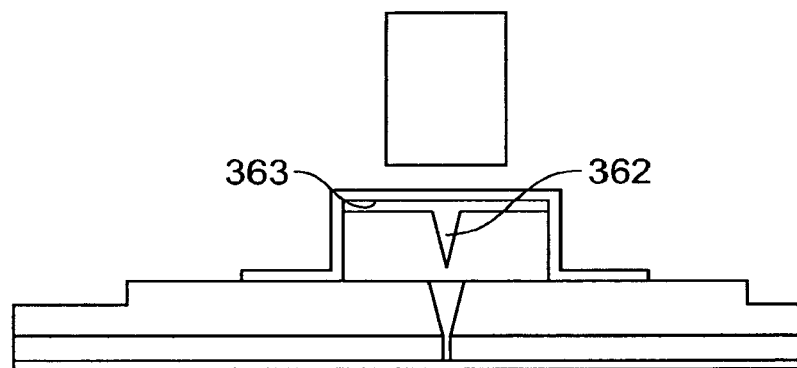
FIGS. 14A-14B illustrate a reservoir with actuation mechanism.
Figure 14B:
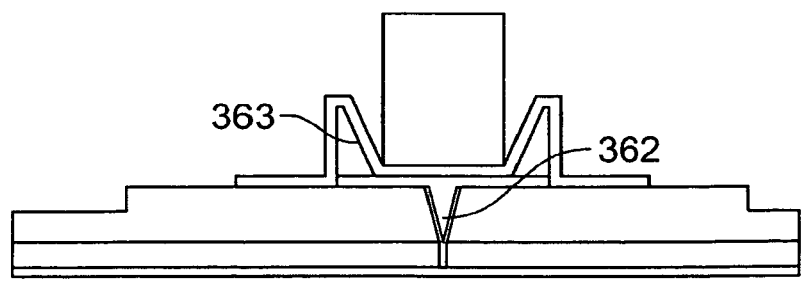

As another example, FIGS. 14A and 14B illustrate a reservoir including an actuation mechanism (e.g., a piercing member) that is initially secured to an interior of an upper wall of the reservoir but separates at least partially from the upper wall upon actuation of the reservoir.

Figure 15A:
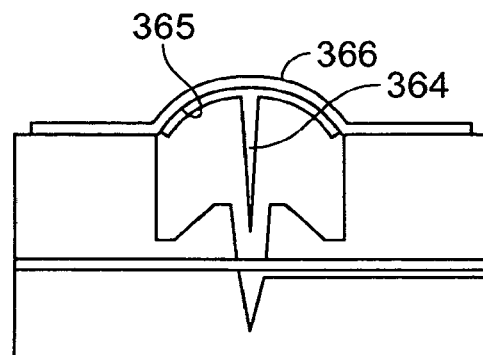
FIGS. 15A-15B illustrate a reservoir with actuation mechanism.
Figure 15B:
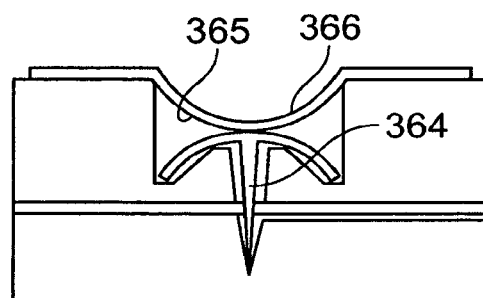

As yet another example, FIGS. 15A and 15B illustrate a reservoir including a piercing member 364 that is initially secured to an interior 365 of an upper wall 366 of the reservoir but substantially separates (e.g., completely separates) from the upper wall upon actuation of the reservoir.

Figure 16:
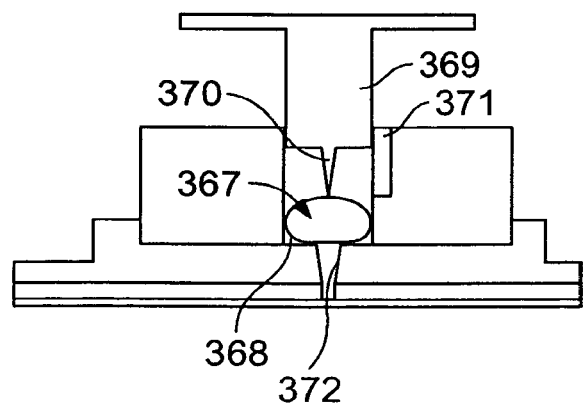
FIG. 16 illustrates a reservoir with actuation mechanism.

While reservoirs have been described as having an enclosed space that is fixed or otherwise integral with a portion of the reservoir, other configurations are possible. For example, referring to FIG. 16, a reservoir includes a capsule-like enclosed space 367 defined by an outer wall 368. The outer wall is generally formed of a material having a low vapor transmission rate. Reservoir also includes an actuation mechanism having a moveable member 369 with a piercing member 370 that pierces the enclosed space to release liquid therein. The liquid passes along a channel 372 leading to a microfluidic network. A channel 371 allows gas (e.g., air) otherwise trapped by the movable member to exit.

Figure 17:
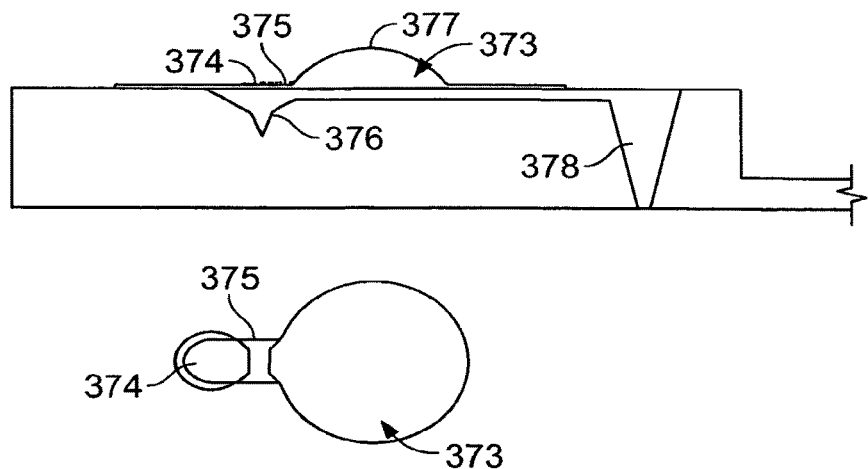
FIG. 17 illustrates a reservoir with actuation mechanism.

While reservoirs have been described as generally overlying an inlet to a microfluidic network, other configurations are possible. For example, referring to FIG. 17, a reservoir includes an enclosed space 373 in which liquid is stored and a connecting portion 374 connected to an inlet 376 of a microfluidic network. The enclosed space 373 and connecting portion 374 are separated by a rupturable seal 375 (e.g., a weak seal). In general, the rupturable seal 375 prevents liquid or vapor from exiting the enclosed space. However, upon the application of pressure to the liquid (e.g., by depressing a wall 377 of the enclosed space), the rupturable seal 375 ruptures allowing the liquid to pass through the weak seal to the connecting portion and into the microfluidic network 378.

Figure 27A:
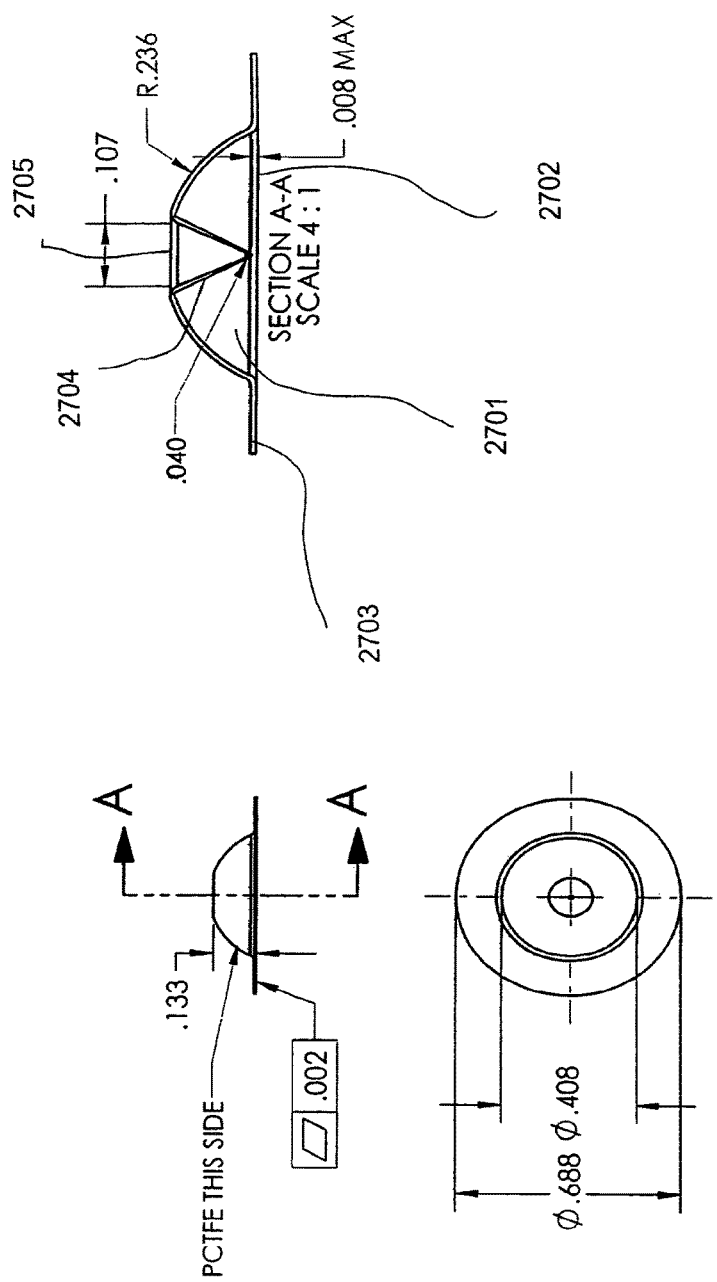
FIGS. 27A and 27B show, respectively, two embodiments of a reservoir with a piercing member.

A still further embodiment of a reservoir with a piercing member is shown in FIG. 27A, which shows a reservoir 2701 having an outer shell 2703 and a piercing element 2704 that are both made of the same piece of material. Such a combined shell and piercing element can be formed from many processes known to one of ordinary skill in the art. Especially preferred processes are vacuum thermo-forming and injection moulding. Piercing element 2704 is generally conical in shape, with the apex adjacent to a membrane 2702; its apex preferably does not exceed 0.040". The piercing element will puncture membrane 2702 and release liquid from reservoir 2701 when the outer shell is depressed. Representative dimensions are shown on FIG. 27A. The reservoir may be constructed so that the upper surface is level, with a flat protective piece 2705 covering the base of the conical shape of piercing element 2704.

Figure 27B:
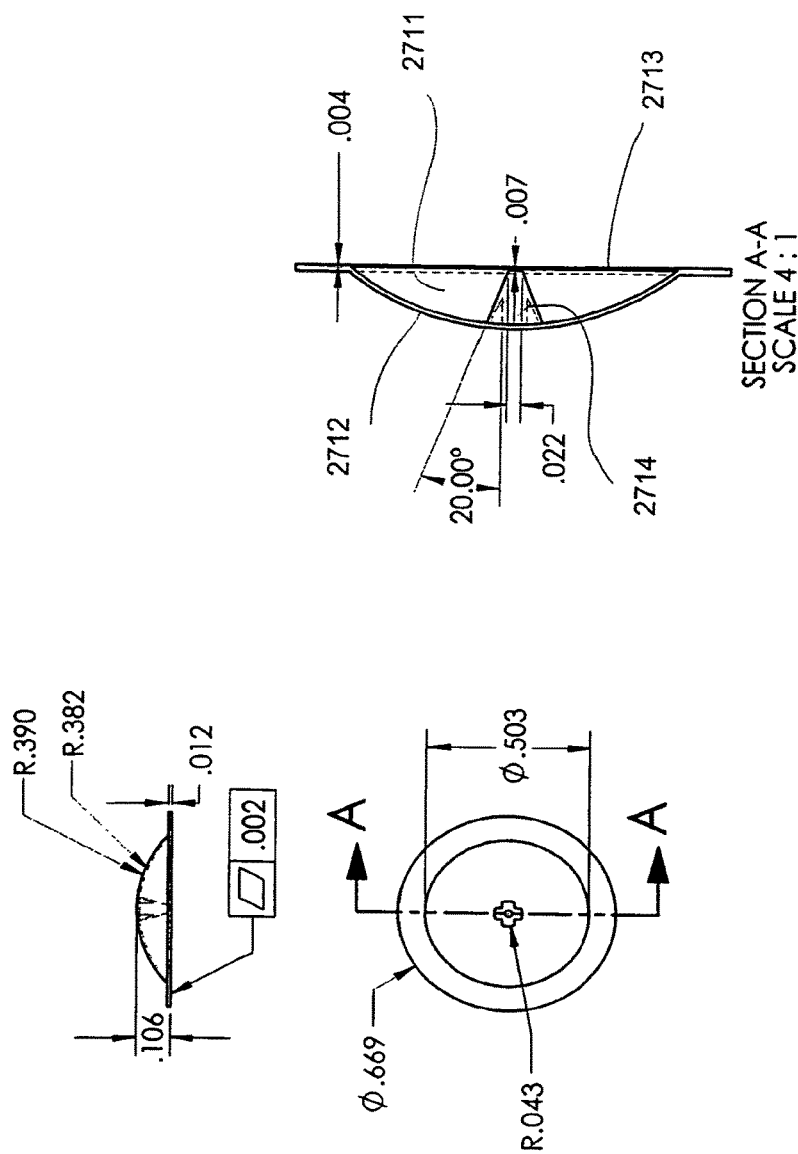

Yet another embodiment of a reservoir with a piercing member is shown in FIG. 27B, showing a reservoir 2711 having a single-piece outer shell 2712 and piercing element 2714. Such a combined shell and piercing element can be formed from many processes known to one of ordinary skill in the art. Especially preferred processes are vacuum thermo-forming and injection moulding. Piercing element 2714 can be frustoconical in shape, with its narrower side adjacent to membrane 2713. Alternatively, piercing element 2714 can comprise several separate piercing elements, arranged within a conical space. Preferably there are four such piercing elements where multiple elements are present.

It is to be understood that the dimensions of the reservoir, piercing element, shell and moulding shown in FIGS. 27A and 27B as decimal quantities in inches are exemplary. In particular, the dimensions are such that the shell does not collapse under its own weight and is not so as strong to prohibit depression of the piercing member when required during operation of the device.

Furthermore, the materials of the various embodiments are also chosen so that the device has a shelf-life of about a year. By this it is meant that the thickness of the various materials are such that they resist loss, through means such as diffusion, of 10% of the liquid volume contained therein over a desired shelf-life period.

Preferably the volume of the reservoir is around 150 μl before a shell is depressed. Upon depression of a shell, the volume is preferably deformed to around half its original volume.

While devices for processing samples have been described as having a generally planar configuration, other configurations can be used. For example, referring to FIG. 18, a device 700 configured to process a polynucleotide-containing sample, such as to prepare the sample for amplification of the polynucleotides, has a generally tube-like or vial-like configuration. Device 700 includes a sample reservoir 704, a reagent reservoir 706, a gas pressure generator 708, a closure (e.g., a cap 710), and a processing region 702 including a retention member 704 having a plurality of particles (e.g. carboxylate beads 705 surface-modified with a ligand, e.g., poly-L-lysine and/or poly-D-lysine, or polyethyleneimine). Retention member 705 and beads 705 may share any or all properties of retention member 216 and surface-modified particles 218. Device 700 also includes an opening 716 and a valve, e.g., a thermally actuated valve 714 for opening and closing opening 716.

In use, a polynucleotide-containing sample is added to sample reservoir 704. Typical sample amounts range from about 100 μL to about 2 mL, although greater or smaller amounts may be used.

Reagent reservoir 706 may be provided to users of device 700 with pre-loaded reagent. Alternatively, device 700 may be configured so that users add reagent to device 700. In any event, the reagents may include, e.g., NaOH solutions and/or buffer solutions such as any of such solutions discussed herein.

Once sample and, if necessary, reagent have been added to device 700, cap 710 is closed to prevent evaporation of sample and reagent materials.

Figures 18, 19:
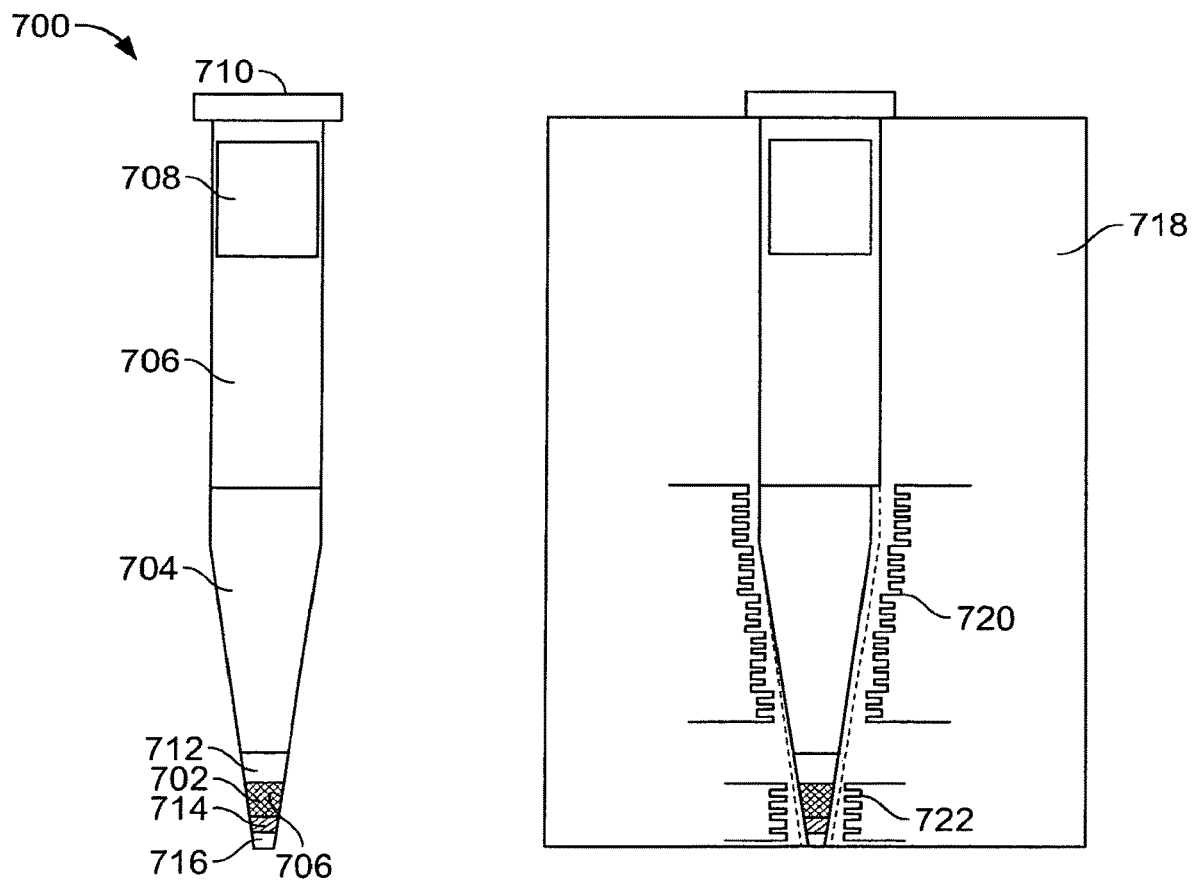
FIG. 18 illustrates a device for separating polynucleotides and inhibitors.
FIG. 19 illustrates the device of FIG. 18 and a device for operation thereof.

Referring also to FIG. 19, an operator 718 is configured to operate device 700. Operator 718 includes a first heat source 720 and a second heat source 722. First heat source 720 heats sample present within sample reservoir 704, such as to lyse cells of the polynucleotide-containing sample to prepare free polynucleotides.

Device 700 may also include an enzyme reservoir 712 comprising an enzyme, e.g., a protease such as pronase, configured to cleave peptide bonds of polypeptides present in the polynucleotide-containing sample. Enzyme reservoir 712 may be provided to users of device 700 with pre-loaded enzyme. Alternatively, device 700 may be configured so that users add enzyme to device 700.

Device 700 may be used to reduce the amount of inhibitors present relative to the amount of polynucleotides to be determined. Thus, the sample is eluted through processing region 702 to contact constituents of the sample with beads 705. Beads 705 retain polynucleotides of the sample as compared to inhibitors as described elsewhere herein. With valve 714 in the open state, sample constituents not retained in processing region 702 exit device 700 via the opening.

Once the polynucleotide-containing sample has eluted through processing region 702, an amount of reagent, e.g., a wash solution, e.g., a buffer such as Tris-EDTA pH 8.0 with 1% Triton X 100 is eluted through processing region 702. The wash solution is generally stored in reagent reservoir 706, which may include a valve configured to release an amount of wash solution. The wash solution elutes remaining polynucleotide-containing sample and inhibitors without eluting retained polynucleotides.

Once inhibitors have been separated from retained polynucleotides, the polynucleotides are released from beads 705. In some embodiments, polynucleotides are released by contacting the beads 705 with a release solution, e.g., a NaOH solution or buffer solution having a pH different from that of the wash solution. Alternatively, or in combination, beads 705 with retained polynucleotides are heated, such as by using second heat source 722 of operator 718. When heat is used to release the polynucleotides, the release solution may be identical with the wash solution.

Gas pressure generator 708 may be used to expel an amount of release solution with released polynucleotides from device 700. Gas pressure generator and/or operator 718 may include a heat source to heat gas present within generator 708. The heated gas expands and provides the gas pressure to expel sample. In some embodiments, and whether or not thermally generated gas pressure is used, gas pressure generator 708 is configured to expel a predetermined volume of material. Typically, the amount of expelled solution is less than about 500 µL, less than about 250 µL, less than about 100 µL, less than about 50 µL, e.g., less than about 25 µL.

EXAMPLES

The following Examples are illustrative and are not intended to be limiting.

Example 1 Preparing Retention Member

Carboxylate surface magnetic beads (Sera-Mag Magnetic Carboxylate modified, Part #3008050250, Seradyn) at a concentration of about 1011 mL−1 were activated for 30 minutes using N-hydroxylsuccinimide (NHS) and 1-ethyl-3-(3-dimethylaminopropyl) carbodiimide (EDAC) in a pH 6.1 500 mM 2-(N-Morpholinio)-ethanesulfonic acid (MES) buffer solution. Activated beads were incubated with 3000 Da or 300,000 Da average molecular weight poly-L-lysine (PLL). After 2 washes to remove unbound PLL, beads were ready for use.

Example 2 Microfluidic Device

Figure 20:
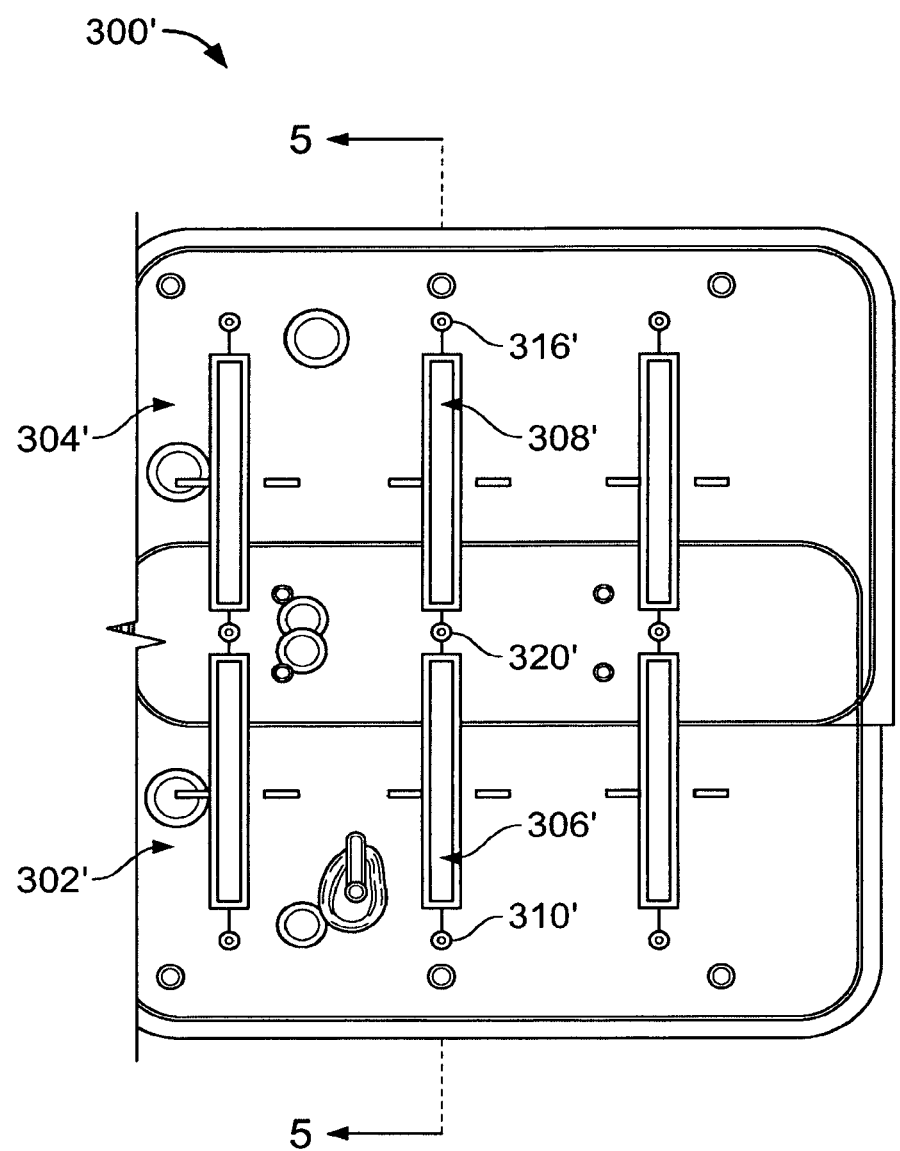
FIG. 20 illustrates a microfluidic device.
Figure 21:
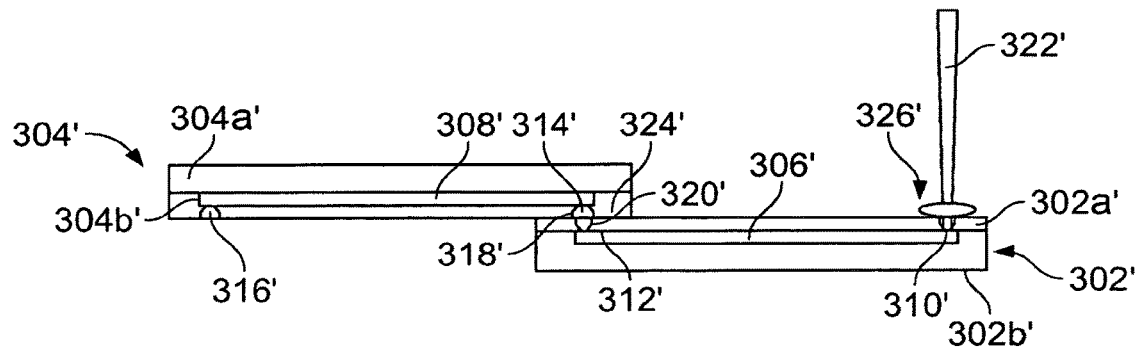
FIG. 21 is a cross-section of the microfluidic device of FIG. 20 taken along 5.

Referring to FIGS. 20 and 21, a microfluidic device 300 was fabricated to demonstrate separation of polynucleotides from inhibitors. Device 300 comprises first and second substrate portions 302', 304', which respectively comprise first and second layers 302 $a'$, 302 $b'$ and 304 $a'$, 304 $b'$. First and second layers 302 $a'$, 302 $b'$ define a channel 306' comprising an inlet 310' and an outlet 312'. First and second layers 304 $a'$, 304 $b'$ define a channel 308' comprising an inlet 314' and an outlet 316'. First and second substrate portions 302', 304' were mated using adhesive 324' so that outlet 312' communicated with inlet 314' with a filter 318' positioned therebetween. A portion of outlet 312' was filed with the activated beads prepared above to provide a processing region 320' comprising a retention member (the beads). A pipette 322' (FIG. 22) secured by adhesive 326' facilitated sample introduction.

In use, sample introduced via inlet 310' passed along channel and through processing region 320'. Excess sample material passed along channel 308' and exited device 300' via outlet 316'. Polynucleotides were preferentially retained by the beads as compared to inhibitors. Once sample had been introduced, additional liquids, e.g., a wash liquid and/or a liquid for use in releasing the retained polynucleotides were introduced via inlet 326'.

Example 3 Retention of DNA

Retention of polynucleotides by the poly-L-lysine modified beads of device 300' was demonstrated by preparing respective devices comprising processing regions having a volume of about 1 µL including about 1000 beads. The beads were modified with poly-L-lysine of between about 15,000 and 30,000 Da. Each processing region was filled with a liquid comprising herring sperm DNA (about 20 µL of sample with a concentration of about 20 mg/mL) thereby placing the beads and liquid in contact. After the liquid and beads had been in contact for 10 minutes, the liquid was removed from each processing region and subjected to quantitative real-time PCR to determine the amount of herring sperm DNA present in the liquid.

Two controls were performed. First, an otherwise identical processing region was packed with unmodified beads, i.e., beads that were identical with the poly-L-lysine beads except for the activation and poly-L-lysine incubation steps. The liquid comprising herring sperm DNA was contacted with these beads, allowed to stand for 10 minutes, removed, and subjected to quantitative real-time PCR. Second, the liquid comprising the herring sperm DNA ("the unprocessed liquid") was subjected to quantitative real-time PCR.

Figure 22:
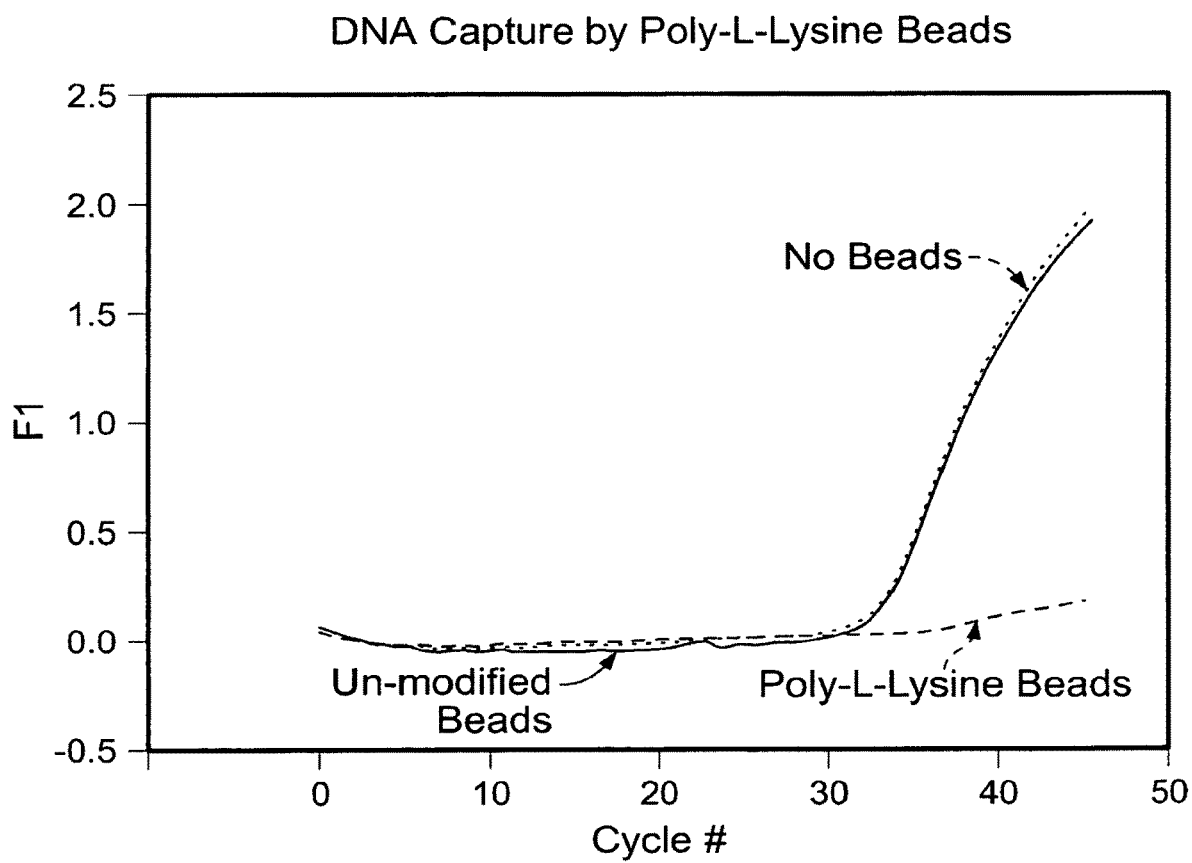
FIG. 22 illustrates the retention of herring sperm DNA.

Referring to FIG. 22, the first and second controls exhibited essentially identical responses indicating the presence of herring sperm DNA in the liquid contacted with the unmodified beads and in the unprocessed liquid. The liquid that had contacted the 3,000 poly-L-lysine beads exhibited a lower response indicating that the modified beads had retained substantially all of the herring sperm DNA. The PCR response of the liquid that had contacted the 300,000 Da poly-L-lysine beads exhibited an amplification response that was at least about 50% greater than for the 3,000 Da beads indicating that the lower molecular weight surface modification was more efficient at retaining the herring sperm DNA.

Example 4 Releasing DNA from Poly-L-Lysine Modified Beads

Devices having processing regions were packed with 3,000 Da poly-L-lysine modified beads. Liquid comprising polynucleotides obtained from group B streptococci (GBS) was contacted with the beads and incubated for 10 minutes as above for the herring sperm DNA. This liquid had been obtained by subjecting about 10,000 GBS bacteria in 10 µl of 20 mM Tris pH 8, 1 mM EDTA, 1% Triton X-100 buffer to thermal lysing at 97° C. for 3 min.

After 10 minutes, the liquid in contact with the beads was removed by flowing about 10 µl of wash solution (Tris-EDTA pH 8.0 with 1% Triton X 100) through the processing region. Subsequently, about 1 µl of 5 mM NaOH solution was added to the processing region. This process left the packed processing region filled with the NaOH solution in contact with the beads. The solution in contact with the beads was heated to 95° C. After 5 minutes of heating at 95° C., the solution in contact with the beads was removed by eluting the processing region with a volume of solution equal to three times the void volume of the processing region.

Figure 23:
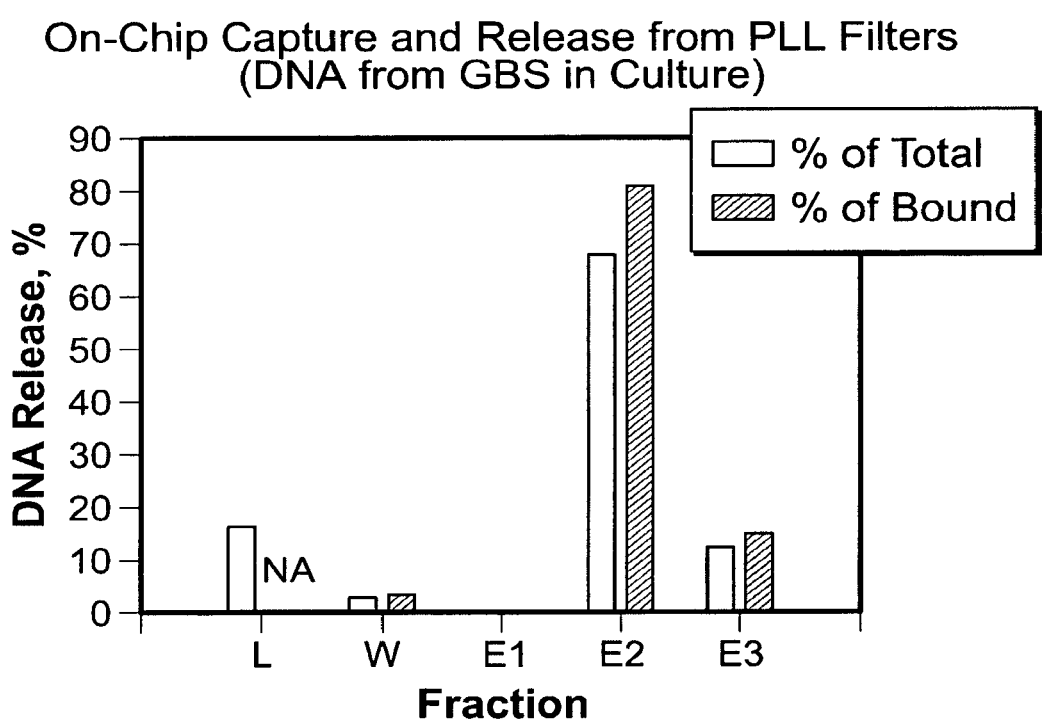
FIG. 23 illustrates the retention and release of DNA from group B streptococci.

Referring to FIG. 23, five aliquots of solution were subjected to quantitative real-time PCR amplification. Aliquots E1, E2, and E3 each contained about 1 µl of liquid. Aliquot L was corresponds to liquid of the original sample that had passed through the processing region. Aliquot W was liquid obtained from wash solution without heating. Aliquot E1 corresponds to the dead volume of device 300, about equal to the volume of channel 308. Thus, liquid of aliquot E1 was present in channel 308 and not in contact with the beads during heating. This liquid had passed through the processing region prior to heating. Aliquot E2 comprises liquid that was present within the processing region and in contact with the beads during heating. Aliquot E3 comprises liquid used to remove aliquot E2 from the processing region.

As seen in FIG. 23, more than 65% of the GBS DNA present in the initial sample was retained by and released from the beads (Aliquot E2). Aliquot E2 also demonstrates the release of more than 80% of the DNA that had been retained by the beads. Less than about 18% of the GBS DNA passed through the processing region without being captured. The wash solution without heating comprised less than 5% of the GBS DNA (Aliquot W).

Example 5 Separation of Polynucleotides and Inhibitors

Buccal cells from the lining of the cheeks provide a source of human genetic material (DNA) that may be used for single nucleotide polymorphism (SNP) detection. A sample comprising buccal cells was subjected to thermal lysing to release DNA from within the cells. Device 300 was used to separate the DNA from concomitant inhibitors as described above. A cleaned-up sample corresponding to aliquot E2 of FIG. 23 was subjected to polymerase chain reaction. A control or crude sample as obtained from the thermal lysing was also amplified.

Figure 24:
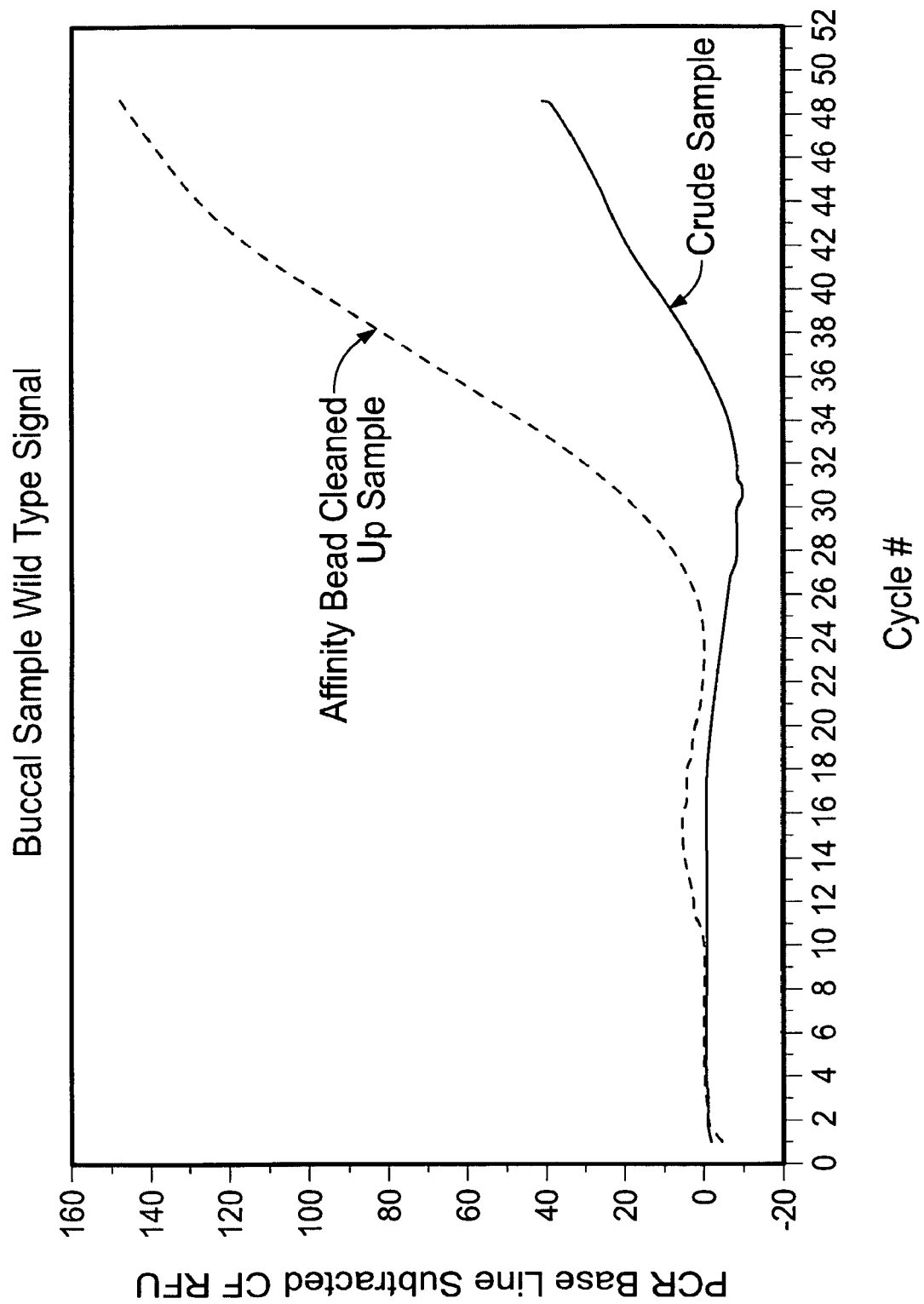
FIG. 24 illustrates the PCR response of a sample from which inhibitors had been removed and of a sample from which inhibitors had not been removed.

Referring to FIG. 24, the cleaned-up sample exhibited substantially higher PCR response in fewer cycles than did the control sample. For example, the clean-up sample exceeded a response of 20 within 32 cycles whereas the control sample required about 45 cycles to achieve the same response.

Blood acts as a sample matrix in variety of diagnostic tests including detection of infectious disease agents, cancer markers and other genetic markers. Hemoglobin present in blood samples is a documented potent inhibitor of PCR. Two 5 ml blood samples were lysed in 20 mM Tris pH 8, 1 mM EDTA, 1% SDS buffer and introduced to respective devices 300, which were operated as described above to prepare two clean-up samples. A third 5 ml blood sample was lysed and prepared using a commercial DNA extraction method Puregene, Gentra Systems, MN. The respective cleaned-up samples and sample subjected to the commercial extraction method were used for a Allelic discrimination analysis (CYP2D6*4 reagents, Applied Biosystems, CA). Each sample contained an amount of DNA corresponding to about 1 ml of blood.

Figure 25:
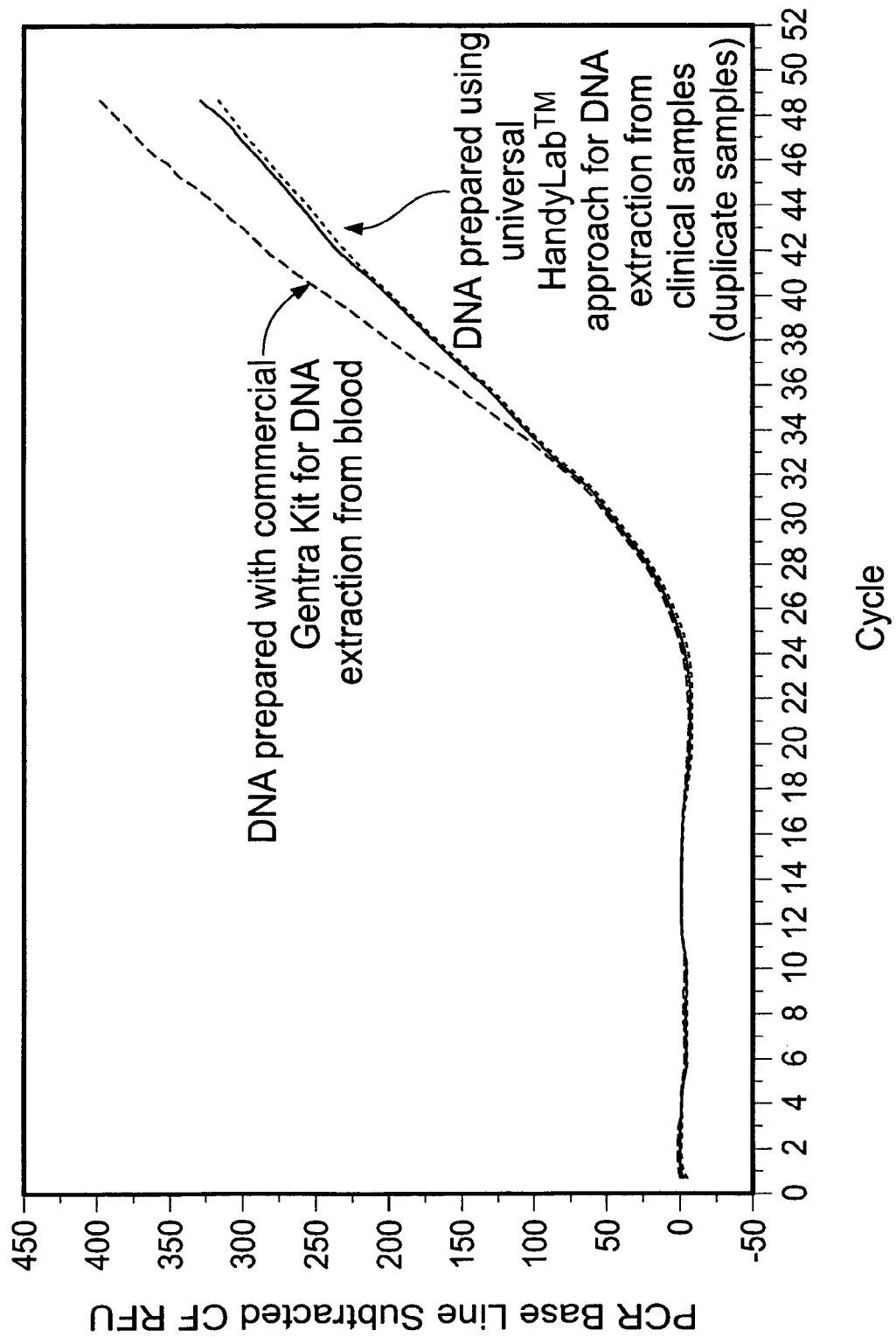
FIG. 25 illustrates the PCR response of a sample prepared in accord with the invention and a sample prepared using a commercial DNA extraction method.

Referring to FIG. 25, the cleaned-up and commercially extracted samples exhibited similar PCR response demonstrating that the processing region of device 300' efficiently removed inhibitors from the blood samples.

Example 6 Protease Resistant Retention Member

The preparation of polynucleotide samples for further processing often includes subjecting the samples to protease treatment in which a protease cleaves peptide bonds of proteins in the sample. An exemplary protease is pronase, a mixture of endo- and exo-proteases. Pronase cleaves most peptide bonds. Certain ligands, such as poly-L-lysine are susceptible to rupture by pronase and other proteases. Thus, if samples are generally not subjected to protease treatment in the presence of the retention member if the ligands bound thereto are susceptible to the proteases.

Poly-D-lysine, the dextro enantiomer of poly-lysine resists cleavage by pronase and other proteases. The ability of a retention member comprising bound poly-D-lysine to retain DNA even when subjected to a protease treatment was studied.

Eight (8) samples were prepared. A first group of 4 samples contained 1000 GBS cells in 10 µl buffer. A second group of 4 samples contained 100 GBS cells in 10 µl buffer. Each of the 8 samples was heated to 97° C. for 3 min to lyse the GBS cells. Four (4) sample sets were created from the heated samples. Each sample set contained 1 sample from each of the first and second groups. The samples of each sample sets were treated as follows.

Figure 26A:
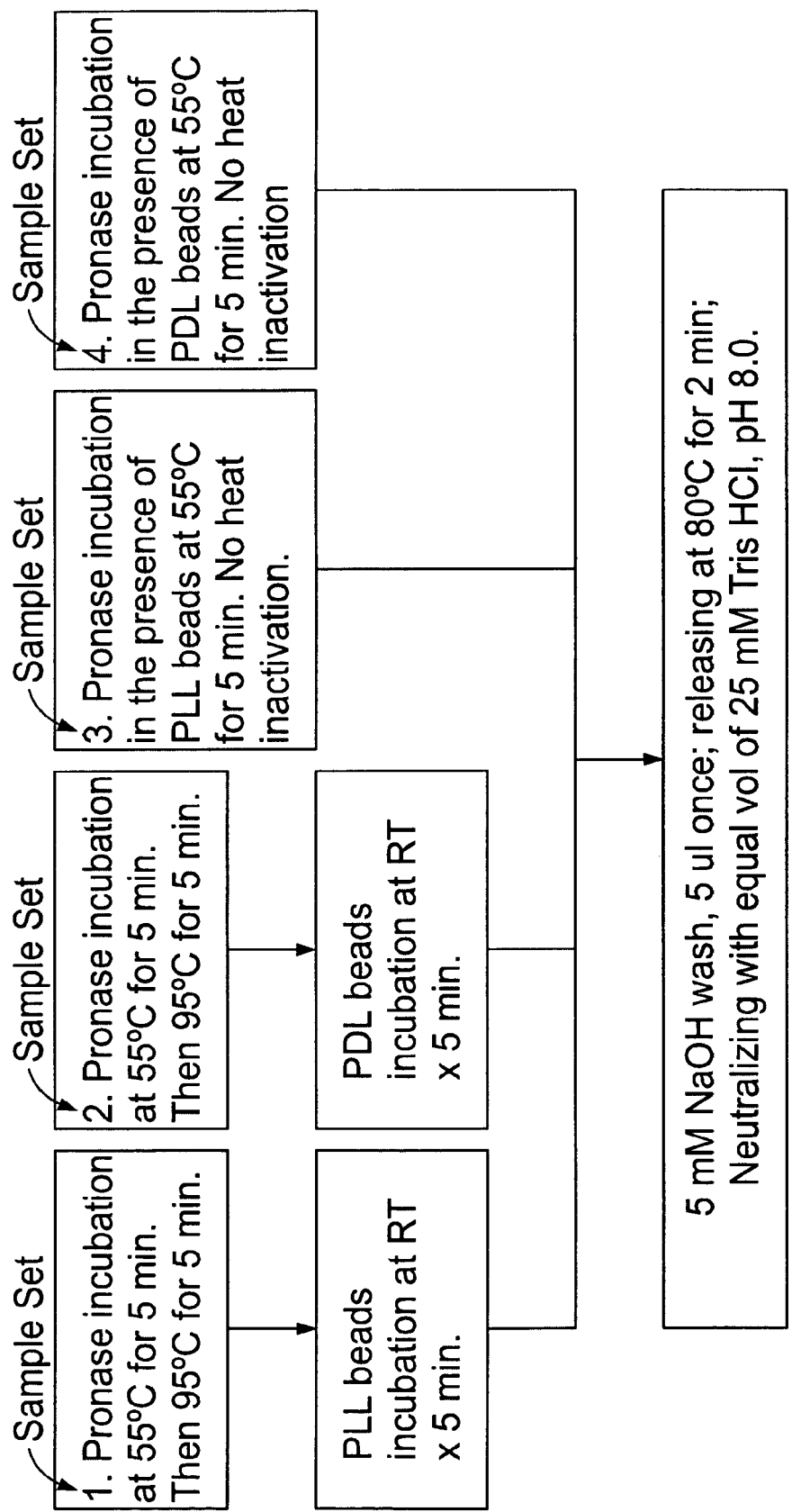
FIG. 26A illustrates a flow chart showing steps performed during a method for separating polynucleotides and inhibitors.

Referring to FIG. 26A, the samples of sample set 1 were subjected to pronase incubation to prepare respective protein cleaved samples, which were then heated to inactivate the proteases. The protein-cleaved, heated samples were contacted with respective retention members each comprising a set of poly-L-lysine modified beads. After 5 minutes, the respective sets of beads were washed with 5 microliters of a 5 mM NaOH solution to separate inhibitors and products of protein cleavage from the bound DNA. The respective sets of beads were each contacted with a second aliquot of NaOH solution and heated to 80 (eighty)° C. for 2 minutes to release the DNA. The solutions with released DNA were neutralized with an equal volume of buffer. The neutralized solutions were analyzed to determine the efficiency of DNA recovery. The results were averaged and shown in FIG. 26B.

The samples of sample set 2 were subjected to pronase incubation to prepare respective protein cleaved samples, which were then heated to inactivate the proteases. The protein-cleaved, heated samples were contacted with respective retention members each comprising a set of poly-D-lysine modified beads. After 5 minutes, the respective sets of beads were washed with 5 microliters of a 5 mM NaOH solution to separate inhibitors and products of protein cleavage from the bound DNA. The respective sets of beads were each contacted with a second aliquot of NaOH solution and heated to 80 (eighty)° C. for 2 minutes to release the DNA. The solutions with released DNA were neutralized with an equal volume of buffer. The neutralized solutions were analyzed to determine the efficiency of DNA recovery. The results were averaged and shown in FIG. 26B.

The samples of sample set 3 were subjected to pronase incubation to prepare respective protein cleaved samples. The proteases were not deactivated either thermally or chemically. The protein-cleaved samples were contacted with respective retention members each comprising a set of poly-L-lysine modified beads. After 5 minutes, the respective sets of beads were washed with 5 microliters of a 5 mM NaOH solution to separate inhibitors and products of protein cleavage from the bound DNA. The respective sets of beads were each contacted with a second aliquot of NaOH solution and heated to 80 (eighty)° C. for 2 minutes to release the DNA. The solutions with released polynucleotides were each neutralized with an equal volume of buffer. The neutralized solutions were analyzed to determine the efficiency of DNA recovery. The results were averaged and shown in FIG. 26B.

The samples of sample set 4 were subjected to pronase incubation to prepare respective protein cleaved samples. The proteases were not deactivated either thermally or chemically. The protein-cleaved samples were contacted with respective retention members each comprising a set of poly-D-lysine modified beads. After 5 minutes, the respective sets of beads were washed with 5 microliters of a 5 mM NaOH solution to separate inhibitors and products of protein cleavage from the bound DNA. The respective sets of beads were each contacted with a second aliquot of NaOH solution and heated to 80 (eighty)° C. for 2 minutes to release the DNA. The solutions with released polynucleotides were each neutralized with an equal volume of buffer. The neutralized solutions were analyzed to determine the efficiency of DNA recovery. The results were averaged and shown in FIG. 26B.

Figure 26B:
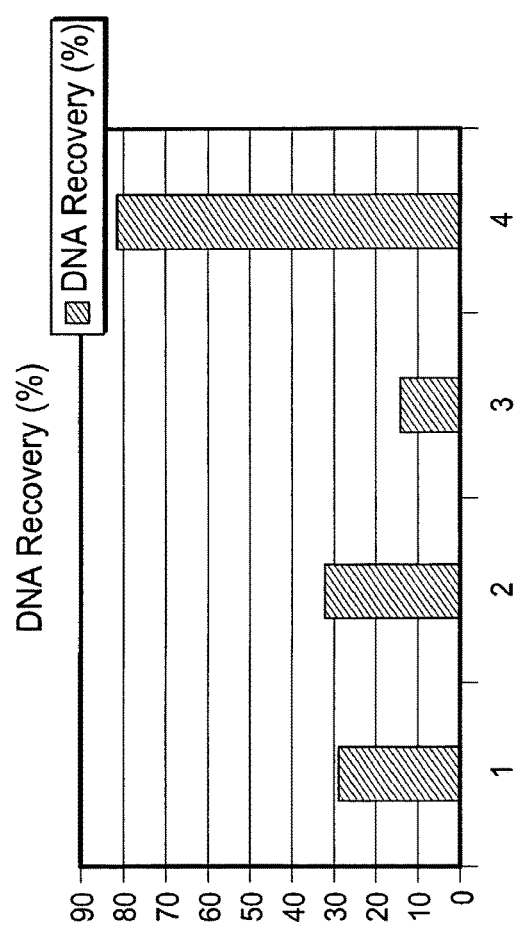
FIG. 26B illustrates DNA from samples subjected to the method of FIG. 26A.

As seen in FIG. 26B, an average of more than 80% of DNA from the GBS cells was recovered using sample set 4 in which the samples were contacted with poly-D-lysine modified beads and subjected to pronase incubation in the presence of the beads without protease inactivation. The recovery efficiency for sample set 4 is more than twice as high as for any of the other samples. Specifically, the recovery efficiencies for sample sets 1, 2, 3, and 4, were 29%, 32%, 14%, and 81.5%, respectively. The efficiencies demonstrate that high recovery efficiencies can be obtained for samples subjected to protease incubation in the presence of a retention member that retains DNA.

Other embodiments are within the claims.

What is claimed is:

1. A system comprising:
   a tubular vessel comprising an opened end and an opening, the opening opposite the opened end of the tubular vessel;
   a valve for opening and closing the opening;
   a closure configured to close the opened end;
   a gas pressure generator disposed within the tubular vessel; and
   a region disposed within the tubular vessel and positioned between the gas pressure generator and the opening,
   wherein the tubular vessel is configured to receive a polynucleotide-containing sample through the opened end and into the region, wherein the polynucleotide-containing sample is configured to be heated within the region once the opened end is closed with the closure, and
   wherein the gas pressure generator is configured to expel a solution with released polynucleotides from the tubular vessel through the opening.

2. The system of claim 1, wherein the valve is a thermally actuated valve for opening and closing the opening.

3. The system of claim 1, wherein the tubular vessel comprises a pre-loaded reagent positioned within the tubular vessel.

4. The system of claim 1, wherein the closure is configured to prevent evaporation of the polynucleotide-containing sample.

5. The system of claim 1, further comprising an external heat source, wherein the tubular vessel is configured to be heated by the external heat source.

6. The system of claim 1, further comprising an operator comprising a first heat source, wherein the first heat source is configured to apply heat to the region disposed within the tubular vessel.

7. The system of claim 6, wherein the operator further comprises a second heat source, wherein the second heat source is configured to apply heat to another region disposed within the tubular vessel.

8. The system of claim 7, wherein the first heat source and the second heat source are spaced apart.

9. The system of claim 7, wherein the first heat source and the second heat source have a different length.

10. The system of claim 7, wherein the first heat source is configured to apply heat to a larger region than the second heat source.

11. The system of claim 1, wherein the tubular vessel comprises a pre-loaded enzyme positioned within the tubular vessel.

12. The system of claim 1, wherein the gas pressure generator comprises a heat source to heat gas present within the gas pressure generator.

13. The system of claim 12, wherein the heated gas is configured to expand and provide the gas pressure to expel the solution.

14. The system of claim 1, wherein the gas pressure generator is configured to expel a predetermined volume.

15. The system of claim 14, wherein the predetermined volume is less than 500 microliters.

16. The system of claim 14, wherein the predetermined volume is less than 50 microliters.

17. The system of claim 1, wherein the region is tapered.

18. The system of claim 1, wherein the tubular vessel is tapered toward the opening.

19. The system of claim 1, wherein the closure has a larger diameter than the tubular vessel.

20. The system of claim 1, wherein the tubular vessel comprises a wash solution valve configured to release an amount of wash solution within the tubular vessel.

* * * * *